(12) United States Patent
Salahieh et al.

(10) Patent No.: US 10,722,631 B2
(45) Date of Patent: Jul. 28, 2020

(54) INTRAVASCULAR BLOOD PUMPS AND METHODS OF USE AND MANUFACTURE

(71) Applicant: Shifamed Holdings, LLC, Campbell, CA (US)

(72) Inventors: Amr Salahieh, Saratoga, CA (US); Tom Saul, Moss Beach, CA (US); Brady Esch, San Jose, CA (US); Anna Kerlo, Milpitas, CA (US); Daniel Hildebrand, Santa Cruz, CA (US); Daniel Varghai, Campbell, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 16/265,828

(22) Filed: Feb. 1, 2019

(65) Prior Publication Data
US 2019/0328948 A1    Oct. 31, 2019

Related U.S. Application Data

(60) Provisional application No. 62/625,312, filed on Feb. 1, 2018.

(51) Int. Cl.
*A61M 1/12* (2006.01)
*A61M 1/10* (2006.01)

(52) U.S. Cl.
CPC .......... *A61M 1/125* (2014.02); *A61M 1/1024* (2014.02); *A61M 1/1034* (2014.02); *A61M 1/122* (2014.02)

(58) Field of Classification Search
CPC .... A61M 1/125; A61M 1/122; A61M 1/1034; A61M 1/1024; A61M 1/12
See application file for complete search history.

(56) References Cited

U.S. PATENT DOCUMENTS

| | | | |
|---|---|---|---|
| 1,061,107 | A | 5/1913 | Nordmark |
| 1,596,933 | A | 8/1926 | Kister |
| 3,175,555 | A | 3/1965 | Ling |
| 3,178,833 | A | 4/1965 | Gulbransen, Jr. |
| 3,208,448 | A | 9/1965 | Woodward |
| 3,233,609 | A | 2/1966 | Leucci |
| 3,421,497 | A | 1/1969 | Chesnut |
| 3,502,412 | A | 3/1970 | Burns |
| 3,504,662 | A | 4/1970 | Jones |

(Continued)

FOREIGN PATENT DOCUMENTS

| | | |
|---|---|---|
| CA | 2739899 C | 5/2017 |
| CN | 1040073 A | 2/1990 |

(Continued)

OTHER PUBLICATIONS

Park et al.; Biologically Inspired, Open, Helicoid Impeller Design for Mechanical Circulatory Assist; ASAIO Journal (American Society for Artificial Internal Organs); DOI: 10.1097/MAT. 0000000000001090: Oct. 23, 2019.

(Continued)

*Primary Examiner* — Mark Bockelman
(74) *Attorney, Agent, or Firm* — Shay Glenn LLP

(57) ABSTRACT

Devices for moving blood within a patient, and methods of doing so. The devices can include a pump portion that includes an impeller and a housing around the impeller, as well as a fluid lumen. The impeller can be activated to cause rotation of the impeller and thereby move fluid within the fluid lumen.

46 Claims, 9 Drawing Sheets

(56) References Cited

U.S. PATENT DOCUMENTS

| | | |
|---|---|---|
| 3,505,987 A | 4/1970 | Heilman |
| 3,568,659 A | 3/1971 | Karnegis |
| 3,693,612 A | 9/1972 | Donahoe et al. |
| 3,734,648 A | 5/1973 | Nielson |
| 3,774,243 A | 11/1973 | Ng et al. |
| 3,837,922 A | 9/1974 | Ng et al. |
| 3,841,837 A | 10/1974 | Kitrilakis et al. |
| 3,860,968 A | 1/1975 | Shapiro |
| 3,919,722 A | 11/1975 | Harmison |
| 4,015,590 A | 4/1977 | Normann |
| 4,037,984 A | 7/1977 | Rafferty et al. |
| 4,046,137 A | 9/1977 | Curless et al. |
| 4,058,857 A | 11/1977 | Runge et al. |
| 4,093,726 A | 6/1978 | Winn et al. |
| 4,135,253 A | 1/1979 | Reich et al. |
| 4,142,845 A | 3/1979 | Lepp et al. |
| 4,173,796 A | 11/1979 | Jarvik |
| 4,190,047 A | 2/1980 | Jacobsen et al. |
| 4,255,821 A | 3/1981 | Carol et al. |
| 4,289,141 A | 9/1981 | Cormier |
| 4,310,930 A | 1/1982 | Goldowsky |
| 4,311,133 A | 1/1982 | Robinson |
| 4,328,806 A | 5/1982 | Cooper |
| 4,370,983 A | 2/1983 | Lichtenstein |
| 4,381,005 A | 4/1983 | Bujan |
| 4,381,567 A | 5/1983 | Robinson et al. |
| 4,382,199 A | 5/1983 | Isaacson |
| 4,389,737 A | 6/1983 | Robinson et al. |
| 4,397,049 A | 8/1983 | Robinson et al. |
| 4,407,304 A | 10/1983 | Lieber et al. |
| 4,506,658 A | 3/1985 | Casile |
| 4,515,589 A | 5/1985 | Austin et al. |
| 4,522,195 A | 6/1985 | Schiff |
| 4,524,466 A | 6/1985 | Hall et al. |
| 4,551,073 A | 11/1985 | Schwab |
| 4,576,606 A | 3/1986 | Pol et al. |
| 4,585,004 A | 4/1986 | Brownlee |
| 4,585,007 A | 4/1986 | Uchigaki et al. |
| 4,599,081 A | 7/1986 | Cohen |
| 4,600,405 A | 7/1986 | Zibelin |
| 4,623,350 A | 11/1986 | Lapeyre et al. |
| 4,625,712 A | 12/1986 | Wampler |
| 4,652,265 A | 3/1987 | McDougall |
| 4,662,358 A | 5/1987 | Farrar et al. |
| 4,675,361 A | 6/1987 | Ward |
| 4,685,910 A | 8/1987 | Schweizer |
| 4,726,379 A | 2/1988 | Altman et al. |
| 4,753,221 A | 6/1988 | Kensey et al. |
| 4,767,289 A | 8/1988 | Parrott et al. |
| 4,771,777 A | 9/1988 | Horzewski et al. |
| 4,779,614 A | 10/1988 | Moise |
| 4,782,817 A | 11/1988 | Singh et al. |
| 4,785,795 A | 11/1988 | Singh |
| 4,802,650 A | 2/1989 | Stricker |
| 4,826,481 A | 5/1989 | Sacks et al. |
| 4,846,831 A | 7/1989 | Skillin |
| 4,850,957 A | 7/1989 | Summers |
| 4,888,009 A | 12/1989 | Lederman et al. |
| 4,888,011 A | 12/1989 | Kung et al. |
| 4,902,272 A | 2/1990 | Milder et al. |
| 4,907,592 A | 3/1990 | Harper |
| 4,908,012 A | 3/1990 | Moise et al. |
| 4,919,647 A | 4/1990 | Nash |
| 4,936,759 A | 6/1990 | Clausen et al. |
| 4,976,683 A | 12/1990 | Gauthier et al. |
| 4,995,857 A | 2/1991 | Arnold |
| 5,026,367 A | 6/1991 | Leckrone et al. |
| D318,113 S | 7/1991 | Moutafis et al. |
| 5,045,051 A | 9/1991 | Milder et al. |
| 5,046,503 A | 9/1991 | Schneiderman |
| 5,047,147 A | 9/1991 | Chevallet et al. |
| 5,049,134 A | 9/1991 | Golding et al. |
| 5,084,064 A | 1/1992 | Barak et al. |
| 5,089,016 A | 2/1992 | Millner et al. |
| 5,090,957 A | 2/1992 | Moutafis et al. |
| 5,092,844 A | 3/1992 | Schwartz et al. |
| 5,092,879 A | 3/1992 | Jarvik |
| 5,112,200 A | 5/1992 | Isaacson et al. |
| 5,112,292 A | 5/1992 | Hwang et al. |
| 5,114,399 A | 5/1992 | Kovalcheck |
| 5,116,305 A | 5/1992 | Milder et al. |
| 5,139,517 A | 8/1992 | Corral |
| 5,145,333 A | 9/1992 | Smith |
| 5,147,281 A | 9/1992 | Thornton et al. |
| 5,171,264 A | 12/1992 | Merrill |
| 5,180,378 A | 1/1993 | Kung et al. |
| 5,192,314 A | 3/1993 | Daskalakis |
| 5,200,050 A | 4/1993 | Ivory et al. |
| 5,205,721 A | 4/1993 | Isaacson |
| 5,211,546 A | 5/1993 | Isaacson et al. |
| 5,261,411 A | 11/1993 | Hughes |
| 5,270,005 A | 12/1993 | Raible |
| 5,300,111 A | 4/1994 | Panton et al. |
| 5,300,112 A | 4/1994 | Barr |
| 5,322,413 A | 6/1994 | Vescovini et al. |
| 5,326,344 A | 7/1994 | Bramm et al. |
| 5,363,856 A | 11/1994 | Hughes et al. |
| 5,397,349 A | 3/1995 | Kolff et al. |
| 5,399,074 A | 3/1995 | Nose et al. |
| 5,405,251 A | 4/1995 | Sipin |
| 5,443,504 A | 8/1995 | Hill |
| 5,486,192 A | 1/1996 | Walinsky et al. |
| 5,487,727 A | 1/1996 | Snider et al. |
| 5,507,629 A | 4/1996 | Jarvik |
| 5,507,795 A | 4/1996 | Chiang et al. |
| 5,510,267 A | 4/1996 | Marshall |
| 5,512,042 A | 4/1996 | Montoya et al. |
| 5,531,789 A | 7/1996 | Yamazaki et al. |
| 5,630,835 A | 5/1997 | Brownlee |
| 5,643,172 A | 7/1997 | Kung et al. |
| 5,643,215 A | 7/1997 | Fuhrman et al. |
| 5,653,696 A | 8/1997 | Shiber |
| 5,662,643 A | 9/1997 | Kung et al. |
| 5,676,526 A | 10/1997 | Kuwana et al. |
| 5,683,231 A | 11/1997 | Nakazawa et al. |
| 5,702,365 A | 12/1997 | King |
| 5,713,730 A | 2/1998 | Nose et al. |
| 5,749,839 A | 5/1998 | Kovacs |
| 5,751,125 A | 5/1998 | Weiss |
| 5,759,148 A | 6/1998 | Sipin |
| 5,766,207 A | 6/1998 | Potter et al. |
| 5,800,138 A | 9/1998 | Merce Vives |
| 5,800,457 A | 9/1998 | Gelbfish |
| 5,803,720 A | 9/1998 | Ohara et al. |
| 5,814,076 A | 9/1998 | Brownlee |
| 5,814,102 A | 9/1998 | Guldner et al. |
| 5,851,174 A | 12/1998 | Jarvik et al. |
| 5,888,241 A | 3/1999 | Jarvik |
| 5,906,579 A | 5/1999 | Vander Salm et al. |
| 5,910,124 A | 6/1999 | Rubin |
| 5,919,369 A | 7/1999 | Ash |
| 5,941,813 A | 8/1999 | Sievers et al. |
| 5,964,694 A | 10/1999 | Siess et al. |
| 5,984,893 A | 11/1999 | Ward |
| 6,013,058 A | 1/2000 | Prosl et al. |
| 6,022,363 A | 2/2000 | Walker et al. |
| 6,030,336 A | 2/2000 | Franchi |
| 6,042,347 A | 3/2000 | Scholl et al. |
| 6,066,085 A | 5/2000 | Heilman et al. |
| 6,066,152 A | 5/2000 | Strauss et al. |
| 6,068,588 A | 5/2000 | Goldowsky |
| 6,071,093 A | 6/2000 | Hart |
| 6,071,258 A | 6/2000 | Dalke et al. |
| 6,082,105 A | 7/2000 | Miyata |
| 6,101,406 A | 8/2000 | Hacker et al. |
| 6,106,509 A | 8/2000 | Loubser |
| 6,113,536 A | 9/2000 | Aboul Hosn et al. |
| 6,117,130 A | 9/2000 | Kung |
| 6,117,390 A | 9/2000 | Corey |
| 6,120,537 A | 9/2000 | Wampler |
| 6,123,726 A | 9/2000 | Mori et al. |
| 6,129,660 A | 10/2000 | Nakazeki et al. |
| 6,139,487 A | 10/2000 | Siess |
| 6,142,752 A | 11/2000 | Akamatsu et al. |

(56) References Cited

U.S. PATENT DOCUMENTS

| | | |
|---|---|---|
| 6,146,771 A | 11/2000 | Wirt et al. |
| 6,149,683 A | 11/2000 | Lancisi et al. |
| 6,152,704 A | 11/2000 | Aboul Hosn et al. |
| 6,155,969 A | 12/2000 | Schima et al. |
| 6,180,058 B1 | 1/2001 | Lindsay |
| 6,197,055 B1 | 3/2001 | Matthews |
| 6,197,289 B1 | 3/2001 | Wirt et al. |
| 6,210,133 B1 | 4/2001 | About Hosn et al. |
| 6,210,318 B1 | 4/2001 | Lederman |
| 6,228,023 B1 | 5/2001 | Zaslaysky et al. |
| 6,236,883 B1 | 5/2001 | Ciaccio et al. |
| 6,254,359 B1 | 7/2001 | Aber |
| 6,270,831 B2 | 8/2001 | Kumar et al. |
| 6,273,861 B1 | 8/2001 | Bates et al. |
| 6,283,949 B1 | 9/2001 | Roorda |
| 6,287,319 B1 | 9/2001 | Aboul Hosn et al. |
| 6,290,685 B1 | 9/2001 | Insley et al. |
| 6,314,322 B1 | 11/2001 | Rosenberg |
| 6,319,231 B1 | 11/2001 | Andrulitis |
| 6,361,292 B1 | 3/2002 | Chang et al. |
| 6,361,501 B1 | 3/2002 | Amano et al. |
| 6,364,833 B1 | 4/2002 | Valerio et al. |
| 6,398,715 B1 | 6/2002 | Magovern et al. |
| 6,400,991 B1 | 6/2002 | Kung |
| 6,406,267 B1 | 6/2002 | Mondiere |
| 6,406,422 B1 | 6/2002 | Landesberg |
| 6,419,657 B1 | 7/2002 | Pacetti |
| 6,422,990 B1 | 7/2002 | Prem |
| 6,432,136 B1 | 8/2002 | Weiss et al. |
| 6,443,944 B1 | 9/2002 | Doshi et al. |
| 6,443,983 B1 | 9/2002 | Nagyszalanczy et al. |
| 6,445,956 B1 | 9/2002 | Laird et al. |
| 6,447,265 B1 | 9/2002 | Antaki et al. |
| 6,447,266 B2 | 9/2002 | Antaki et al. |
| 6,447,441 B1 | 9/2002 | Yu et al. |
| 6,497,680 B1 | 12/2002 | Holst et al. |
| 6,503,224 B1 | 1/2003 | Forman et al. |
| 6,503,450 B1 | 1/2003 | Afzal et al. |
| 6,508,787 B2 | 1/2003 | Erbel et al. |
| 6,508,806 B1 | 1/2003 | Hoste |
| 6,527,699 B1 | 3/2003 | Goldowsky |
| 6,533,716 B1 | 3/2003 | Schmitz-Rode et al. |
| 6,533,724 B2 | 3/2003 | McNair |
| 6,537,315 B2 | 3/2003 | Yamazaki et al. |
| 6,540,658 B1 | 4/2003 | Fasciano et al. |
| 6,540,659 B1 | 4/2003 | Milbocker |
| 6,544,543 B1 | 4/2003 | Mandrusov et al. |
| 6,547,716 B1 | 4/2003 | Milbocker |
| 6,562,022 B2 | 5/2003 | Hoste et al. |
| 6,572,529 B2 | 6/2003 | Wilk |
| 6,572,534 B1 | 6/2003 | Milbocker et al. |
| 6,602,182 B1 | 8/2003 | Milbocker |
| 6,616,596 B1 | 9/2003 | Milbocker |
| 6,620,120 B2 | 9/2003 | Landry et al. |
| 6,623,420 B2 | 9/2003 | Reich et al. |
| 6,626,821 B1 | 9/2003 | Kung et al. |
| 6,626,889 B1 | 9/2003 | Simpson et al. |
| 6,626,935 B1 | 9/2003 | Ainsworth et al. |
| 6,632,215 B1 | 10/2003 | Lemelson |
| 6,635,083 B1 | 10/2003 | Cheng et al. |
| 6,656,220 B1 | 12/2003 | Gomez et al. |
| 6,669,624 B2 | 12/2003 | Frazier |
| 6,669,662 B1 | 12/2003 | Webler |
| 6,676,679 B1 | 1/2004 | Mueller et al. |
| 6,688,869 B1 | 2/2004 | Simonds |
| 6,699,231 B1 | 3/2004 | Sterman et al. |
| 6,709,382 B1 | 3/2004 | Horner |
| 6,730,102 B1 | 5/2004 | Burdulis et al. |
| 6,746,416 B2 | 6/2004 | Hubbard et al. |
| 6,749,615 B2 | 6/2004 | Burdulis et al. |
| 6,769,871 B2 | 8/2004 | Yamazaki |
| 6,790,171 B1 | 9/2004 | Gründeman et al. |
| 6,811,749 B2 | 11/2004 | Lindsay |
| 6,821,295 B1 | 11/2004 | Farrar |
| 6,837,890 B1 | 1/2005 | Chludzinski et al. |
| 6,846,296 B1 | 1/2005 | Milbocker et al. |
| 6,866,650 B2 | 3/2005 | Stevens et al. |
| 6,879,126 B2 | 4/2005 | Paden et al. |
| 6,884,210 B2 | 4/2005 | Nose et al. |
| 6,908,280 B2 | 6/2005 | Yamazaki |
| 6,908,435 B1 | 6/2005 | Mueller et al. |
| 6,929,632 B2 | 8/2005 | Nita et al. |
| 6,929,660 B1 | 8/2005 | Ainsworth et al. |
| 6,942,672 B2 | 9/2005 | Heilman et al. |
| 6,945,978 B1 | 9/2005 | Hyde |
| 6,949,066 B2 | 9/2005 | Bearnson et al. |
| 6,969,345 B2 | 11/2005 | Jassawalla et al. |
| 6,981,942 B2 | 1/2006 | Khaw et al. |
| 7,022,100 B1 | 4/2006 | Aboul Hosn et al. |
| 7,025,742 B2 | 4/2006 | Rubenstein et al. |
| 7,027,875 B2 | 4/2006 | Siess et al. |
| 7,029,483 B2 | 4/2006 | Schwartz |
| 7,037,253 B2 | 5/2006 | French et al. |
| 7,048,747 B2 | 5/2006 | Arcia et al. |
| 7,074,018 B2 | 7/2006 | Chang |
| 7,108,652 B2 | 9/2006 | Stenberg et al. |
| 7,118,525 B2 | 10/2006 | Coleman et al. |
| 7,122,151 B2 | 10/2006 | Reeder et al. |
| 7,125,376 B2 | 10/2006 | Viole et al. |
| 7,126,310 B1 | 10/2006 | Barron |
| 7,150,711 B2 | 12/2006 | Nüsser et al. |
| 7,155,291 B2 | 12/2006 | Zarinetchi et al. |
| 7,172,551 B2 | 2/2007 | Leasure |
| 7,189,260 B2 | 3/2007 | Horvath et al. |
| 7,229,258 B2 | 6/2007 | Wood et al. |
| 7,229,402 B2 | 6/2007 | Diaz et al. |
| 7,238,151 B2 | 7/2007 | Frazier |
| 7,244,224 B2 | 7/2007 | Tsukahara et al. |
| 7,247,166 B2 | 7/2007 | Pienknagura |
| 7,303,581 B2 | 12/2007 | Peralta |
| 7,331,972 B1 | 2/2008 | Cox |
| 7,331,987 B1 | 2/2008 | Cox |
| 7,361,726 B2 | 4/2008 | Pacetti et al. |
| 7,377,927 B2 | 5/2008 | Burdulis et al. |
| 7,392,077 B2 | 6/2008 | Mueller et al. |
| 7,393,181 B2 | 7/2008 | McBride et al. |
| 7,396,327 B2 | 7/2008 | Morello |
| 7,479,102 B2 | 1/2009 | Jarvik |
| 7,520,850 B2 | 4/2009 | Brockway |
| 7,524,277 B1 | 4/2009 | Wang et al. |
| 7,541,000 B2 | 6/2009 | Stringer et al. |
| 7,544,160 B2 | 6/2009 | Gross |
| 7,547,391 B2 | 6/2009 | Petrie |
| 7,585,322 B2 | 9/2009 | Azzolina |
| 7,588,530 B2 | 9/2009 | Heilman et al. |
| 7,588,549 B2 | 9/2009 | Eccleston |
| 7,591,199 B2 | 9/2009 | Weldon et al. |
| 7,611,478 B2 | 11/2009 | Lucke et al. |
| 7,628,756 B2 | 12/2009 | Hacker et al. |
| 7,713,259 B2 | 5/2010 | Gosiengfiao et al. |
| RE41,394 E | 6/2010 | Bugge et al. |
| 7,736,296 B2 | 6/2010 | Siess et al. |
| 7,736,375 B2 | 6/2010 | Crow |
| 7,758,492 B2 | 7/2010 | Weatherbee |
| 7,776,991 B2 | 8/2010 | Pacetti et al. |
| 7,780,628 B1 | 8/2010 | Keren et al. |
| 7,794,419 B2 | 9/2010 | Paolini et al. |
| 7,794,743 B2 | 9/2010 | Simhambhatla et al. |
| 7,819,834 B2 | 10/2010 | Paul |
| 7,828,710 B2 | 11/2010 | Shifflette |
| 7,833,239 B2 | 11/2010 | Nash |
| 7,841,976 B2 | 11/2010 | McBride et al. |
| 7,850,594 B2 | 12/2010 | Sutton et al. |
| 7,862,501 B2 | 1/2011 | Woodard |
| 7,878,967 B1 | 2/2011 | Khanal |
| 7,914,436 B1 | 3/2011 | Kung |
| 7,922,657 B2 | 4/2011 | Gillinov et al. |
| 7,942,804 B2 | 5/2011 | Khaw |
| 7,963,905 B2 | 6/2011 | Salmonsen et al. |
| 7,972,122 B2 | 7/2011 | LaRose et al. |
| 7,972,291 B2 | 7/2011 | Ibragimov |
| 7,985,442 B2 | 7/2011 | Gong |
| 7,988,728 B2 | 8/2011 | Ayre |
| 7,993,259 B2 | 8/2011 | Kang et al. |

(56) References Cited

U.S. PATENT DOCUMENTS

| | | |
|---|---|---|
| 7,993,260 B2 | 8/2011 | Bolling |
| 7,993,358 B2 | 8/2011 | O'Brien |
| 7,998,054 B2 | 8/2011 | Bolling |
| 7,998,190 B2 | 8/2011 | Gharib et al. |
| 8,012,079 B2 | 9/2011 | Delgado |
| 8,012,508 B2 | 9/2011 | Ludwig |
| 8,029,728 B2 | 10/2011 | Lindsay |
| 8,034,098 B1 | 10/2011 | Callas et al. |
| 8,048,442 B1 | 11/2011 | Hossainy et al. |
| 8,052,749 B2 | 11/2011 | Salahieh et al. |
| 8,070,742 B2 | 12/2011 | Woo |
| 8,070,804 B2 | 12/2011 | Hyde et al. |
| 8,075,472 B2 | 12/2011 | Zilbershlag et al. |
| 8,079,948 B2 | 12/2011 | Shifflette |
| 8,083,726 B1 | 12/2011 | Wang |
| 8,123,669 B2 | 2/2012 | Siess et al. |
| 8,133,272 B2 | 3/2012 | Hyde |
| RE43,299 E | 4/2012 | Siess |
| 8,152,035 B2 | 4/2012 | Earl |
| 8,152,845 B2 | 4/2012 | Bourque |
| 8,153,083 B2 | 4/2012 | Briggs |
| 8,157,719 B1 | 4/2012 | Ainsworth et al. |
| 8,157,721 B2 | 4/2012 | Sugiura |
| 8,157,758 B2 | 4/2012 | Pecor et al. |
| 8,158,062 B2 | 4/2012 | Dykes et al. |
| 8,162,021 B2 | 4/2012 | Tomasetti et al. |
| 8,167,589 B2 | 5/2012 | Hidaka et al. |
| 8,172,783 B1 | 5/2012 | Ray |
| 8,177,750 B2 | 5/2012 | Steinbach et al. |
| 8,187,324 B2 | 5/2012 | Webler et al. |
| 8,197,463 B2 | 6/2012 | Intoccia |
| 8,210,829 B2 | 7/2012 | Horvath et al. |
| 8,241,199 B2 | 8/2012 | Maschke |
| 8,257,258 B2 | 9/2012 | Zocchi |
| 8,257,375 B2 | 9/2012 | Maschke |
| 8,266,943 B2 | 9/2012 | Miyakoshi et al. |
| D669,585 S | 10/2012 | Bourque |
| 8,277,476 B2 | 10/2012 | Taylor et al. |
| 8,282,359 B2 | 10/2012 | Ayre et al. |
| 8,292,908 B2 | 10/2012 | Nieman et al. |
| D671,646 S | 11/2012 | Bourque et al. |
| 8,303,482 B2 | 11/2012 | Schima et al. |
| 8,323,173 B2 | 12/2012 | Benkowski et al. |
| 8,328,750 B2 | 12/2012 | Peters et al. |
| 8,329,114 B2 | 12/2012 | Temple |
| 8,329,158 B2 | 12/2012 | Hossainy et al. |
| 8,366,599 B2 | 2/2013 | Tansley et al. |
| 8,372,137 B2 | 2/2013 | Pienknagura |
| 8,377,033 B2 | 2/2013 | Basu et al. |
| 8,377,083 B2 | 2/2013 | Mauch et al. |
| 8,382,695 B1 | 2/2013 | Patel |
| 8,388,649 B2 | 3/2013 | Woodard et al. |
| 8,419,609 B2 | 4/2013 | Shambaugh et al. |
| 8,419,944 B2 | 4/2013 | Alkanhal |
| 8,439,909 B2 | 5/2013 | Wang et al. |
| 8,449,444 B2 | 5/2013 | Poirier |
| 8,454,683 B2 | 6/2013 | Rafiee et al. |
| 8,485,961 B2 | 7/2013 | Campbell et al. |
| 8,496,874 B2 | 7/2013 | Gellman et al. |
| 8,500,620 B2 | 8/2013 | Lu et al. |
| 8,506,471 B2 | 8/2013 | Bourque |
| 8,535,211 B2 | 9/2013 | Campbell et al. |
| 8,535,212 B2 | 9/2013 | Robert |
| 8,538,515 B2 | 9/2013 | Atanasoska et al. |
| 8,545,382 B2 | 10/2013 | Suzuki et al. |
| 8,545,447 B2 | 10/2013 | Demarais et al. |
| 8,562,509 B2 | 10/2013 | Bates |
| 8,568,289 B2 | 10/2013 | Mazur |
| 8,579,858 B2 | 11/2013 | Reitan et al. |
| 8,579,967 B2 | 11/2013 | Webler et al. |
| 8,585,572 B2 | 11/2013 | Mehmanesh |
| 8,586,527 B2 | 11/2013 | Singh |
| 8,591,393 B2 | 11/2013 | Walters et al. |
| 8,591,394 B2 | 11/2013 | Peters et al. |
| 8,591,449 B2 | 11/2013 | Hudson |
| 8,591,538 B2 | 11/2013 | Gellman |
| 8,591,539 B2 | 11/2013 | Gellman |
| D696,769 S | 12/2013 | Schenck et al. |
| 8,597,170 B2 | 12/2013 | Walters et al. |
| 8,608,661 B1 | 12/2013 | Mandrusov et al. |
| 8,613,777 B2 | 12/2013 | Siess et al. |
| 8,613,892 B2 | 12/2013 | Stafford |
| 8,617,239 B2 | 12/2013 | Reitan |
| 8,631,680 B2 | 1/2014 | Fleischli et al. |
| 8,632,449 B2 | 1/2014 | Masuzawa et al. |
| 8,641,594 B2 | 2/2014 | LaRose et al. |
| 8,657,871 B2 | 2/2014 | Limon |
| 8,657,875 B2 | 2/2014 | Kung et al. |
| 8,668,473 B2 | 3/2014 | LaRose et al. |
| 8,684,903 B2 | 4/2014 | Nour |
| 8,690,749 B1 | 4/2014 | Nunez |
| 8,690,823 B2 | 4/2014 | Yribarren et al. |
| 8,697,058 B2 | 4/2014 | Basu et al. |
| 8,708,948 B2 | 4/2014 | Consigny et al. |
| 8,715,151 B2 | 5/2014 | Poirier |
| 8,715,156 B2 | 5/2014 | Jayaraman |
| 8,715,707 B2 | 5/2014 | Hossainy et al. |
| 8,721,516 B2 | 5/2014 | Scheckel |
| 8,721,517 B2 | 5/2014 | Zeng et al. |
| 8,734,331 B2 | 5/2014 | Evans et al. |
| 8,734,508 B2 | 5/2014 | Hastings et al. |
| 8,739,727 B2 | 6/2014 | Austin et al. |
| 8,740,920 B2 | 6/2014 | Goldfarb et al. |
| 8,741,287 B2 | 6/2014 | Brophy et al. |
| 8,758,388 B2 | 6/2014 | Pah |
| 8,766,788 B2 | 7/2014 | D'Ambrosio |
| 8,777,832 B1 | 7/2014 | Wang et al. |
| 8,790,399 B2 | 7/2014 | Frazier et al. |
| 8,795,576 B2 | 8/2014 | Tao et al. |
| 8,814,543 B2 | 8/2014 | Liebing |
| 8,814,776 B2 | 8/2014 | Hastie et al. |
| 8,814,933 B2 | 8/2014 | Siess |
| 8,815,274 B2 | 8/2014 | DesNoyer et al. |
| 8,821,366 B2 | 9/2014 | Farnan et al. |
| 8,837,096 B2 | 9/2014 | Seebruch |
| 8,840,539 B2 | 9/2014 | Zilbershlag |
| 8,840,566 B2 | 9/2014 | Seibel et al. |
| 8,849,398 B2 | 9/2014 | Evans |
| 8,862,232 B2 | 10/2014 | Zarinetchi et al. |
| 8,864,642 B2 | 10/2014 | Scheckel |
| 8,876,685 B2 | 11/2014 | Crosby et al. |
| 8,882,744 B2 | 11/2014 | Dormanen et al. |
| 8,888,675 B2 | 11/2014 | Stankus et al. |
| 8,894,387 B2 | 11/2014 | White |
| 8,894,561 B2 | 11/2014 | Callaway et al. |
| 8,897,873 B2 | 11/2014 | Schima et al. |
| 8,900,060 B2 | 12/2014 | Liebing |
| 8,905,910 B2 | 12/2014 | Reichenbach et al. |
| 8,927,700 B2 | 1/2015 | McCauley et al. |
| 8,932,141 B2 | 1/2015 | Liebing |
| 8,932,197 B2 | 1/2015 | Gregoric et al. |
| 8,942,828 B1 | 1/2015 | Schecter |
| 8,944,748 B2 | 2/2015 | Liebing |
| 8,945,159 B2 | 2/2015 | Nussbaum |
| 8,956,402 B2 | 2/2015 | Cohn |
| 8,961,387 B2 | 2/2015 | Duncan |
| 8,961,466 B2 | 2/2015 | Steinbach |
| 8,971,980 B2 | 3/2015 | Mace et al. |
| 8,974,519 B2 | 3/2015 | Gennrich et al. |
| 8,992,406 B2 | 3/2015 | Corbett |
| 8,997,349 B2 | 4/2015 | Mori et al. |
| 9,002,468 B2 | 4/2015 | Shea et al. |
| 9,023,010 B2 | 5/2015 | Chiu et al. |
| 9,028,216 B2 | 5/2015 | Schumacher et al. |
| 9,028,392 B2 | 5/2015 | Shifflette |
| 9,028,859 B2 | 5/2015 | Hossainy et al. |
| 9,033,863 B2 | 5/2015 | Jarvik |
| 9,033,909 B2 | 5/2015 | Aihara |
| 9,039,595 B2 | 5/2015 | Ayre et al. |
| 9,044,236 B2 | 6/2015 | Nguyen et al. |
| 9,056,159 B2 | 6/2015 | Medvedev et al. |
| 9,066,992 B2 | 6/2015 | Stankus et al. |
| 9,067,005 B2 | 6/2015 | Ozaki et al. |
| 9,067,006 B2 | 6/2015 | Toellner |

(56) References Cited

U.S. PATENT DOCUMENTS

| | | |
|---|---|---|
| 9,072,825 B2 | 7/2015 | Pfeffer et al. |
| 9,078,692 B2 | 7/2015 | Shturman et al. |
| 9,089,329 B2 | 7/2015 | Hoarau et al. |
| 9,089,634 B2 | 7/2015 | Schumacher et al. |
| 9,089,635 B2 | 7/2015 | Reichenbach et al. |
| 9,089,670 B2 | 7/2015 | Scheckel |
| 9,095,428 B2 | 8/2015 | Kabir et al. |
| 9,096,703 B2 | 8/2015 | Li et al. |
| 9,101,302 B2 | 8/2015 | Mace et al. |
| 9,125,977 B2 | 9/2015 | Nishimura et al. |
| 9,127,680 B2 | 9/2015 | Yanai et al. |
| 9,138,516 B2 | 9/2015 | Vischer et al. |
| 9,138,518 B2 | 9/2015 | Campbell et al. |
| 9,144,638 B2 | 9/2015 | Zimmermann et al. |
| 9,162,017 B2 | 10/2015 | Evans et al. |
| 9,168,361 B2 | 10/2015 | Ehrenreich et al. |
| 9,180,227 B2 | 11/2015 | Ludwig et al. |
| 9,180,235 B2 | 11/2015 | Forsell |
| 9,192,705 B2 | 11/2015 | Yanai et al. |
| 9,199,020 B2 | 12/2015 | Siess |
| 9,217,442 B2 | 12/2015 | Wiessler et al. |
| D746,975 S | 1/2016 | Schenck et al. |
| 9,227,002 B1 | 1/2016 | Giridharan et al. |
| 9,239,049 B2 | 1/2016 | Jarnagin et al. |
| 9,265,870 B2 | 2/2016 | Reichenbach et al. |
| 9,278,189 B2 | 3/2016 | Corbett |
| 9,283,314 B2 | 3/2016 | Prasad et al. |
| 9,291,591 B2 | 3/2016 | Simmons et al. |
| 9,295,550 B2 | 3/2016 | Nguyen et al. |
| 9,295,767 B2 | 3/2016 | Schmid et al. |
| 9,308,302 B2 | 4/2016 | Zeng |
| 9,308,304 B2 | 4/2016 | Peters et al. |
| 9,314,558 B2 | 4/2016 | Er |
| 9,314,559 B2 | 4/2016 | Smith et al. |
| 9,328,741 B2 | 5/2016 | Liebing |
| 9,333,284 B2 | 5/2016 | Thompson et al. |
| 9,339,596 B2 | 5/2016 | Roehn |
| 9,345,824 B2 | 5/2016 | Mohl et al. |
| 9,358,329 B2 | 6/2016 | Fitzgerald et al. |
| 9,358,330 B2 | 6/2016 | Schumacher |
| 9,364,255 B2 | 6/2016 | Weber |
| 9,364,592 B2 | 6/2016 | McBride et al. |
| 9,370,613 B2 | 6/2016 | Hsu et al. |
| 9,375,445 B2 | 6/2016 | Hossainy et al. |
| 9,381,285 B2 | 7/2016 | Ozaki et al. |
| 9,387,284 B2 | 7/2016 | Heilman et al. |
| 9,409,012 B2 | 8/2016 | Eidenschink et al. |
| 9,416,783 B2 | 8/2016 | Schumacher et al. |
| 9,416,791 B2 | 8/2016 | Toellner |
| 9,421,311 B2 | 8/2016 | Tanner et al. |
| 9,433,713 B2 | 9/2016 | Corbett et al. |
| 9,435,450 B2 | 9/2016 | Muennich |
| 9,446,179 B2 | 9/2016 | Keenan et al. |
| 9,452,249 B2 | 9/2016 | Kearsley et al. |
| 9,474,840 B2 | 10/2016 | Siess |
| 9,486,565 B2 | 11/2016 | Göllner et al. |
| 9,492,601 B2 | 11/2016 | Casas et al. |
| 9,504,491 B2 | 11/2016 | Callas et al. |
| 9,511,179 B2 | 12/2016 | Casas et al. |
| 9,522,257 B2 | 12/2016 | Webler |
| 9,526,818 B2 | 12/2016 | Kearsley et al. |
| 9,533,084 B2 | 1/2017 | Siess et al. |
| 9,533,085 B2 | 1/2017 | Hanna |
| 9,539,378 B2 | 1/2017 | Tuseth |
| 9,550,017 B2 | 1/2017 | Spanier et al. |
| 9,555,173 B2 | 1/2017 | Spanier |
| 9,555,175 B2 | 1/2017 | Bulent et al. |
| 9,555,177 B2 | 1/2017 | Curtis et al. |
| 9,556,873 B2 | 1/2017 | Yanai et al. |
| 9,561,309 B2 | 2/2017 | Glauser et al. |
| 9,561,313 B2 | 2/2017 | Taskin |
| 9,592,328 B2 | 3/2017 | Jeevanandam et al. |
| 9,603,983 B2 | 3/2017 | Roehn et al. |
| 9,603,984 B2 | 3/2017 | Romero et al. |
| 9,611,743 B2 | 4/2017 | Toellner et al. |
| 9,616,157 B2 | 4/2017 | Akdis |
| 9,616,159 B2 | 4/2017 | Anderson et al. |
| 9,623,163 B1 | 4/2017 | Fischi |
| 9,631,754 B2 | 4/2017 | Richardson et al. |
| 9,642,984 B2 | 5/2017 | Schumacher et al. |
| 9,656,010 B2 | 5/2017 | Burke |
| 9,656,030 B1 | 5/2017 | Webler et al. |
| 9,662,211 B2 | 5/2017 | Hodson et al. |
| 9,669,141 B2 | 6/2017 | Parker et al. |
| 9,669,142 B2 | 6/2017 | Spanier et al. |
| 9,669,143 B2 | 6/2017 | Guerrero |
| 9,675,450 B2 | 6/2017 | Straka et al. |
| 9,675,738 B2 | 6/2017 | Tanner et al. |
| 9,675,739 B2 | 6/2017 | Tanner et al. |
| 9,675,742 B2 | 6/2017 | Casas et al. |
| 9,687,596 B2 | 6/2017 | Poirier |
| 9,687,630 B2 | 6/2017 | Basu et al. |
| 9,700,659 B2 | 7/2017 | Kantrowitz et al. |
| 9,713,662 B2 | 7/2017 | Rosenberg et al. |
| 9,713,663 B2 | 7/2017 | Medvedev et al. |
| 9,715,839 B2 | 7/2017 | Pybus et al. |
| 9,717,615 B2 | 8/2017 | Grandt |
| 9,717,832 B2 | 8/2017 | Taskin et al. |
| 9,717,839 B2 | 8/2017 | Hashimoto |
| 9,726,195 B2 | 8/2017 | Cecere et al. |
| 9,731,058 B2 | 8/2017 | Siebenhaar et al. |
| 9,731,101 B2 | 8/2017 | Bertrand et al. |
| 9,737,361 B2 | 8/2017 | Magana et al. |
| 9,737,651 B2 | 8/2017 | Wampler |
| 9,744,280 B2 | 8/2017 | Schade et al. |
| 9,744,287 B2 | 8/2017 | Bulent et al. |
| 9,750,859 B2 | 9/2017 | Bulent et al. |
| 9,757,502 B2 | 9/2017 | Burke et al. |
| 9,770,202 B2 | 9/2017 | Ralston et al. |
| 9,770,543 B2 | 9/2017 | Tanner et al. |
| 9,771,801 B2 | 9/2017 | Schumacher et al. |
| 9,775,930 B2 | 10/2017 | Michal et al. |
| 9,782,279 B2 | 10/2017 | Kassab |
| 9,782,527 B2 | 10/2017 | Thomas et al. |
| 9,795,780 B2 | 10/2017 | Serna et al. |
| 9,801,987 B2 | 10/2017 | Farnan et al. |
| 9,801,992 B2 | 10/2017 | Giordano et al. |
| 9,821,098 B2 | 11/2017 | Horvath et al. |
| 9,821,146 B2 | 11/2017 | Tao et al. |
| 9,827,356 B2 | 11/2017 | Muller et al. |
| 9,833,314 B2 | 12/2017 | Corbett |
| 9,833,550 B2 | 12/2017 | Siess |
| 9,833,551 B2 | 12/2017 | Criscione et al. |
| 9,839,734 B1 | 12/2017 | Menon et al. |
| 9,844,618 B2 | 12/2017 | Muller-Spanka et al. |
| 9,850,906 B2 | 12/2017 | Ozaki et al. |
| 9,855,437 B2 | 1/2018 | Nguyen et al. |
| 9,861,504 B2 | 1/2018 | Abunassar et al. |
| 9,861,731 B2 | 1/2018 | Tamburino |
| 9,872,948 B2 | 1/2018 | Siess |
| 9,878,087 B2 | 1/2018 | Richardson et al. |
| 9,878,169 B2 | 1/2018 | Hossainy |
| 9,889,242 B2 | 2/2018 | Pfeffer et al. |
| 9,895,244 B2 | 2/2018 | Papp et al. |
| 9,895,475 B2 | 2/2018 | Toellner et al. |
| 9,907,890 B2 | 3/2018 | Muller |
| 9,907,892 B2 | 3/2018 | Broen et al. |
| 9,913,937 B2 | 3/2018 | Schwammenthal et al. |
| 9,918,822 B2 | 3/2018 | Abunassar et al. |
| 9,919,085 B2 | 3/2018 | Throckmorton et al. |
| 9,919,088 B2 | 3/2018 | Bonde et al. |
| 9,919,089 B2 | 3/2018 | Garrigue |
| 9,950,101 B2 | 4/2018 | Smith et al. |
| 9,956,410 B2 | 5/2018 | Deem et al. |
| 9,962,258 B2 | 5/2018 | Seguin et al. |
| 9,974,893 B2 | 5/2018 | Toellner |
| 9,974,894 B2 | 5/2018 | Morello |
| 9,981,078 B2 | 5/2018 | Jin et al. |
| 9,985,374 B2 | 5/2018 | Hodges |
| 9,987,407 B2 | 6/2018 | Grant et al. |
| 10,010,273 B2 | 7/2018 | Sloan et al. |
| 10,022,499 B2 | 7/2018 | Galasso |
| 10,028,835 B2 | 7/2018 | Kermode et al. |
| 10,029,037 B2 | 7/2018 | Muller et al. |

(56) References Cited

U.S. PATENT DOCUMENTS

| | | |
|---|---|---|
| 10,029,038 B2 | 7/2018 | Hodges |
| 10,029,039 B2 | 7/2018 | Dague et al. |
| 10,031,124 B2 | 7/2018 | Galasso |
| 10,034,972 B2 | 7/2018 | Wampler et al. |
| 10,039,873 B2 | 8/2018 | Siegenthaler |
| 10,046,146 B2 | 8/2018 | Manderfeld et al. |
| 10,058,349 B2 | 8/2018 | Gunderson et al. |
| 10,058,641 B2 | 8/2018 | Mollison et al. |
| 10,058,652 B2 | 8/2018 | Tsoukalis |
| 10,058,653 B2 | 8/2018 | Wang et al. |
| 10,077,777 B2 | 9/2018 | Horvath et al. |
| 10,080,828 B2 | 9/2018 | Wiesener et al. |
| 10,080,834 B2 | 9/2018 | Federspiel et al. |
| 10,080,871 B2 | 9/2018 | Schumacher et al. |
| 2001/0003802 A1 | 6/2001 | Vitale |
| 2001/0053928 A1 | 12/2001 | Edelman et al. |
| 2002/0057989 A1 | 5/2002 | Afzal et al. |
| 2002/0058971 A1 | 5/2002 | Zarinetchi et al. |
| 2002/0068848 A1 | 6/2002 | Zadini et al. |
| 2002/0128709 A1 | 9/2002 | Pless |
| 2002/0147495 A1 | 10/2002 | Petroff |
| 2003/0069465 A1 | 4/2003 | Benkowski et al. |
| 2003/0088151 A1 | 5/2003 | Kung et al. |
| 2003/0131995 A1 | 7/2003 | de Rouffignac et al. |
| 2003/0155111 A1 | 8/2003 | Vinegar et al. |
| 2003/0173081 A1 | 9/2003 | Vinegar et al. |
| 2003/0173082 A1 | 9/2003 | Vinegar et al. |
| 2003/0173085 A1 | 9/2003 | Vinegar et al. |
| 2003/0178191 A1 | 9/2003 | Maher et al. |
| 2003/0209348 A1 | 11/2003 | Ward et al. |
| 2004/0024285 A1 | 2/2004 | Muckter |
| 2004/0040715 A1 | 3/2004 | Wellington et al. |
| 2004/0097782 A1 | 5/2004 | Korakianitis et al. |
| 2004/0228724 A1 | 11/2004 | Capone et al. |
| 2004/0249363 A1 | 12/2004 | Burke et al. |
| 2005/0010077 A1 | 1/2005 | Calderon |
| 2005/0043805 A1 | 2/2005 | Chudik |
| 2005/0060036 A1 | 3/2005 | Schultz et al. |
| 2005/0113632 A1 | 5/2005 | Ortiz et al. |
| 2005/0119599 A1 | 6/2005 | Kanz et al. |
| 2005/0187616 A1 | 8/2005 | Realyvasquez |
| 2005/0209617 A1 | 9/2005 | Koven et al. |
| 2005/0220636 A1 | 10/2005 | Henein et al. |
| 2005/0254976 A1 | 11/2005 | Carrier et al. |
| 2005/0256540 A1 | 11/2005 | Silver et al. |
| 2006/0111641 A1 | 5/2006 | Manera et al. |
| 2006/0116700 A1 | 6/2006 | Crow |
| 2006/0129082 A1 | 6/2006 | Rozga |
| 2006/0155158 A1 | 7/2006 | Aboul Hosn |
| 2006/0177343 A1 | 8/2006 | Brian et al. |
| 2006/0195098 A1 | 8/2006 | Schumacher |
| 2006/0257355 A1 | 11/2006 | Stewart et al. |
| 2006/0293664 A1 | 12/2006 | Schumacher |
| 2007/0106274 A1 | 5/2007 | Ayre et al. |
| 2007/0167091 A1 | 7/2007 | Schumacher |
| 2007/0203453 A1 | 8/2007 | Mori et al. |
| 2007/0213690 A1 | 9/2007 | Phillips et al. |
| 2007/0299314 A1 | 12/2007 | Bertolero et al. |
| 2008/0045779 A1 | 2/2008 | Rinaldi et al. |
| 2008/0065014 A1 | 3/2008 | Von Oepen et al. |
| 2008/0076101 A1 | 3/2008 | Hyde et al. |
| 2008/0097273 A1 | 4/2008 | Levin et al. |
| 2008/0097562 A1 | 4/2008 | Tan |
| 2008/0119421 A1 | 5/2008 | Tuszynski et al. |
| 2008/0132748 A1 | 6/2008 | Shifflette |
| 2008/0132749 A1 | 6/2008 | Hegde et al. |
| 2008/0167711 A1 | 7/2008 | Roorda |
| 2008/0200750 A1 | 8/2008 | James |
| 2008/0208329 A1 | 8/2008 | Bishop et al. |
| 2008/0228026 A1 | 9/2008 | Manera et al. |
| 2008/0240947 A1 | 10/2008 | Allaire et al. |
| 2008/0243030 A1 | 10/2008 | Seibel et al. |
| 2008/0275295 A1 | 11/2008 | Gertner |
| 2008/0275354 A1 | 11/2008 | Thuramalla et al. |
| 2008/0296433 A1 | 12/2008 | Brenner et al. |
| 2008/0300677 A1 | 12/2008 | Schrayer |
| 2009/0063402 A1 | 3/2009 | Hayter |
| 2009/0093764 A1 | 4/2009 | Pfeffer et al. |
| 2009/0171448 A1 | 7/2009 | Eli |
| 2009/0177028 A1 | 7/2009 | White |
| 2009/0182307 A1 | 7/2009 | Yap et al. |
| 2009/0188964 A1 | 7/2009 | Orlov |
| 2009/0259089 A1 | 10/2009 | Gelbart et al. |
| 2010/0016703 A1 | 1/2010 | Batkin et al. |
| 2010/0022943 A1 | 1/2010 | Mauch et al. |
| 2010/0076380 A1 | 3/2010 | Hui |
| 2010/0084326 A1 | 4/2010 | Takesawa |
| 2010/0087742 A1 | 4/2010 | Bishop et al. |
| 2010/0105978 A1 | 4/2010 | Matsui et al. |
| 2010/0152523 A1 | 6/2010 | MacDonald et al. |
| 2010/0152525 A1 | 6/2010 | Weizman et al. |
| 2010/0152526 A1 | 6/2010 | Pacella et al. |
| 2010/0160751 A1 | 6/2010 | Hete et al. |
| 2010/0185220 A1 | 7/2010 | Naghavi et al. |
| 2010/0222635 A1 | 9/2010 | Poirier |
| 2010/0222878 A1 | 9/2010 | Poirier |
| 2010/0249489 A1 | 9/2010 | Jarvik |
| 2011/0098548 A1 | 4/2011 | Budiman et al. |
| 2011/0178596 A1 | 7/2011 | Hauck et al. |
| 2011/0224655 A1 | 9/2011 | Asirvatham et al. |
| 2011/0301625 A1 | 12/2011 | Mauch et al. |
| 2011/0304240 A1 | 12/2011 | Meitav et al. |
| 2012/0022316 A1 | 1/2012 | Aboul-Hosn et al. |
| 2012/0028908 A1 | 2/2012 | Viswanath et al. |
| 2012/0039711 A1 | 2/2012 | Roehn |
| 2012/0109060 A1 | 5/2012 | Kick et al. |
| 2012/0165641 A1 | 6/2012 | Burnett et al. |
| 2012/0179184 A1 | 7/2012 | Orlov |
| 2012/0184803 A1 | 7/2012 | Simon et al. |
| 2012/0190918 A1 | 7/2012 | Oepen et al. |
| 2012/0224970 A1 | 9/2012 | Schumacher et al. |
| 2012/0239139 A1 | 9/2012 | Wnendt et al. |
| 2012/0252709 A1 | 10/2012 | Felts et al. |
| 2012/0302458 A1 | 11/2012 | Adamczyk et al. |
| 2012/0330683 A1 | 12/2012 | Ledwidge et al. |
| 2013/0023373 A1 | 1/2013 | Janek |
| 2013/0040407 A1 | 2/2013 | Brophy et al. |
| 2013/0053693 A1 | 2/2013 | Breznock et al. |
| 2013/0060077 A1 | 3/2013 | Liebing |
| 2013/0144144 A1 | 6/2013 | Laster et al. |
| 2013/0204362 A1 | 8/2013 | Toellner et al. |
| 2013/0211489 A1 | 8/2013 | Makower et al. |
| 2013/0233798 A1 | 9/2013 | Wiktor et al. |
| 2013/0245360 A1 | 9/2013 | Schumacher |
| 2013/0281761 A1 | 10/2013 | Kapur |
| 2013/0303969 A1 | 11/2013 | Keenan et al. |
| 2013/0310845 A1 | 11/2013 | Thor et al. |
| 2013/0317604 A1 | 11/2013 | Min et al. |
| 2013/0344047 A1 | 12/2013 | Pacetti et al. |
| 2014/0017200 A1 | 1/2014 | Michal et al. |
| 2014/0039465 A1 | 2/2014 | Schulz et al. |
| 2014/0039603 A1 | 2/2014 | Wang |
| 2014/0058190 A1 | 2/2014 | Gohean et al. |
| 2014/0066693 A1 | 3/2014 | Goldfarb et al. |
| 2014/0128659 A1 | 5/2014 | Heuring et al. |
| 2014/0128795 A1 | 5/2014 | Keren et al. |
| 2014/0163664 A1 | 6/2014 | Goldsmith |
| 2014/0190523 A1 | 7/2014 | Garvey et al. |
| 2014/0194678 A1 | 7/2014 | Wildhirt et al. |
| 2014/0194717 A1 | 7/2014 | Wildhirt et al. |
| 2014/0199377 A1 | 7/2014 | Stankus et al. |
| 2014/0200655 A1 | 7/2014 | Webler et al. |
| 2014/0207232 A1 | 7/2014 | Garrigue |
| 2014/0228741 A1 | 8/2014 | Frankowski et al. |
| 2014/0243970 A1 | 8/2014 | Yanai |
| 2014/0255176 A1 | 9/2014 | Bredenbreuker et al. |
| 2014/0275721 A1 | 9/2014 | Yanai et al. |
| 2014/0275725 A1 | 9/2014 | Schenck et al. |
| 2014/0288354 A1 | 9/2014 | Timms et al. |
| 2014/0309481 A1 | 10/2014 | Medvedev et al. |
| 2014/0336444 A1 | 11/2014 | Bonde |
| 2014/0336486 A1 | 11/2014 | Ouyang et al. |
| 2014/0336747 A1 | 11/2014 | Rapoza et al. |
| 2014/0341726 A1 | 11/2014 | Wu et al. |

(56) References Cited

U.S. PATENT DOCUMENTS

| | | |
|---|---|---|
| 2014/0350328 A1 | 11/2014 | Mohl |
| 2014/0357938 A1 | 12/2014 | Pilla et al. |
| 2014/0370073 A1 | 12/2014 | Tang et al. |
| 2015/0005571 A1 | 1/2015 | Jeffery et al. |
| 2015/0018747 A1 | 1/2015 | Michal et al. |
| 2015/0031938 A1 | 1/2015 | Crosby et al. |
| 2015/0051437 A1 | 2/2015 | Miyakoshi et al. |
| 2015/0068069 A1 | 3/2015 | Tran et al. |
| 2015/0080639 A1 | 3/2015 | Radziemski et al. |
| 2015/0080743 A1 | 3/2015 | Siess |
| 2015/0087890 A1 | 3/2015 | Spanier et al. |
| 2015/0112210 A1 | 4/2015 | Webler |
| 2015/0120323 A1 | 4/2015 | Galasso et al. |
| 2015/0134048 A1 | 5/2015 | Ding |
| 2015/0152878 A1 | 6/2015 | McBride et al. |
| 2015/0159643 A1 | 6/2015 | Koob |
| 2015/0174060 A1 | 6/2015 | Heit et al. |
| 2015/0191607 A1 | 7/2015 | McDaniel |
| 2015/0207331 A1 | 7/2015 | Petersen |
| 2015/0216685 A1 | 8/2015 | Spence et al. |
| 2015/0222128 A1 | 8/2015 | Hansen |
| 2015/0222139 A1 | 8/2015 | Petersen et al. |
| 2015/0226691 A1 | 8/2015 | Wang et al. |
| 2015/0230709 A1 | 8/2015 | Milner et al. |
| 2015/0231317 A1 | 8/2015 | Schima et al. |
| 2015/0238671 A1 | 8/2015 | Mesallum |
| 2015/0265757 A1 | 9/2015 | Dowling et al. |
| 2015/0283027 A1 | 10/2015 | Lampe et al. |
| 2015/0285258 A1 | 10/2015 | Foster |
| 2015/0290370 A1 | 10/2015 | Crunkleton et al. |
| 2015/0290377 A1 | 10/2015 | Kearsley et al. |
| 2015/0306291 A1 | 10/2015 | Bonde et al. |
| 2015/0320926 A1 | 11/2015 | Fitzpatrick et al. |
| 2015/0328382 A1 | 11/2015 | Corbett et al. |
| 2015/0364861 A1 | 12/2015 | Lucke et al. |
| 2015/0367050 A1 | 12/2015 | Bulent et al. |
| 2015/0368335 A1 | 12/2015 | Banerjee et al. |
| 2015/0374892 A1 | 12/2015 | Yanai et al. |
| 2016/0022887 A1 | 1/2016 | Wampler |
| 2016/0030649 A1 | 2/2016 | Zeng |
| 2016/0038315 A1 | 2/2016 | Consigny et al. |
| 2016/0045098 A1 | 2/2016 | Tsubouchi |
| 2016/0045652 A1 | 2/2016 | Cornen |
| 2016/0045654 A1 | 2/2016 | Connor |
| 2016/0058434 A1 | 3/2016 | Delaloye et al. |
| 2016/0067395 A1 | 3/2016 | Jimenez et al. |
| 2016/0085714 A1 | 3/2016 | Goodnow et al. |
| 2016/0175044 A1 | 6/2016 | Abunassar et al. |
| 2016/0182158 A1 | 6/2016 | Lee et al. |
| 2016/0184499 A1 | 6/2016 | Ricci et al. |
| 2016/0199556 A1 | 7/2016 | Ayre et al. |
| 2016/0199557 A1 | 7/2016 | Bluvshtein et al. |
| 2016/0203275 A1 | 7/2016 | Benjamin et al. |
| 2016/0220269 A1 | 8/2016 | Labropoulos et al. |
| 2016/0220785 A1 | 8/2016 | Fabro |
| 2016/0222969 A1 | 8/2016 | Heide et al. |
| 2016/0250399 A1 | 9/2016 | Tiller et al. |
| 2016/0250400 A1 | 9/2016 | Schumacher |
| 2016/0251720 A1 | 9/2016 | Schulze et al. |
| 2016/0256620 A1 | 9/2016 | Scheckel et al. |
| 2016/0263299 A1 | 9/2016 | Xu et al. |
| 2016/0271161 A1 | 9/2016 | Dobson |
| 2016/0271309 A1 | 9/2016 | Throckmorton et al. |
| 2016/0279310 A1 | 9/2016 | Scheckel et al. |
| 2016/0303301 A1 | 10/2016 | Bluvshtein et al. |
| 2016/0308403 A1 | 10/2016 | Bluvshtein et al. |
| 2016/0317291 A1 | 11/2016 | Bishop et al. |
| 2016/0317333 A1 | 11/2016 | Ainsworth et al. |
| 2016/0325034 A1 | 11/2016 | Wiktor et al. |
| 2016/0348688 A1 | 12/2016 | Schumacher et al. |
| 2016/0354526 A1 | 12/2016 | Whisenant et al. |
| 2016/0375187 A1 | 12/2016 | Lee et al. |
| 2017/0000361 A1 | 1/2017 | Meyering et al. |
| 2017/0000935 A1 | 1/2017 | Vasilyev et al. |
| 2017/0007552 A1 | 1/2017 | Slepian |
| 2017/0007762 A1 | 1/2017 | Hayter et al. |
| 2017/0014401 A1 | 1/2017 | Dalton et al. |
| 2017/0021074 A1 | 1/2017 | Opfermann et al. |
| 2017/0028114 A1 | 2/2017 | Göllner et al. |
| 2017/0028115 A1 | 2/2017 | Muller |
| 2017/0035952 A1 | 2/2017 | Muller |
| 2017/0035954 A1 | 2/2017 | Muller et al. |
| 2017/0043076 A1 | 2/2017 | Wampler et al. |
| 2017/0063143 A1 | 3/2017 | Hoarau et al. |
| 2017/0080136 A1 | 3/2017 | Janeczek et al. |
| 2017/0100527 A1 | 4/2017 | Schwammenthal et al. |
| 2017/0112984 A1 | 4/2017 | Vargas Fonseca |
| 2017/0119946 A1 | 5/2017 | McChrystal et al. |
| 2017/0136165 A1 | 5/2017 | Hansen et al. |
| 2017/0136225 A1 | 5/2017 | Siess et al. |
| 2017/0143883 A1 | 5/2017 | Spence |
| 2017/0143952 A1 | 5/2017 | Siess et al. |
| 2017/0157309 A1 | 6/2017 | Begg et al. |
| 2017/0193184 A1 | 7/2017 | Hayter et al. |
| 2017/0196638 A1 | 7/2017 | Serna et al. |
| 2017/0202575 A1 | 7/2017 | Stanfield et al. |
| 2017/0215918 A1 | 8/2017 | Tao et al. |
| 2017/0224896 A1 | 8/2017 | Graham et al. |
| 2017/0232168 A1 | 8/2017 | Reichenbach et al. |
| 2017/0232169 A1 | 8/2017 | Muller |
| 2017/0232172 A1 | 8/2017 | Mesallum |
| 2017/0239407 A1 | 8/2017 | Hayward |
| 2017/0250575 A1 | 8/2017 | Wong et al. |
| 2017/0265994 A1 | 9/2017 | Krone |
| 2017/0274128 A1 | 9/2017 | Tamburino et al. |
| 2017/0281025 A9 | 10/2017 | Glover et al. |
| 2017/0281841 A1 | 10/2017 | Larose et al. |
| 2017/0281842 A1 | 10/2017 | Larose et al. |
| 2017/0290964 A1 | 10/2017 | Barry |
| 2017/0290965 A1 | 10/2017 | McBride et al. |
| 2017/0296227 A1 | 10/2017 | Osypka |
| 2017/0296725 A1 | 10/2017 | Peters et al. |
| 2017/0312106 A1 | 11/2017 | Gomez et al. |
| 2017/0312416 A1 | 11/2017 | Strueber |
| 2017/0312492 A1 | 11/2017 | Fantuzzi et al. |
| 2017/0319113 A1 | 11/2017 | Hurd et al. |
| 2017/0323713 A1 | 11/2017 | Moeller et al. |
| 2017/0325943 A1 | 11/2017 | Robin et al. |
| 2017/0333607 A1 | 11/2017 | Zarins |
| 2017/0333673 A1 | 11/2017 | Tuval et al. |
| 2017/0340789 A1 | 11/2017 | Bonde et al. |
| 2017/0340790 A1 | 11/2017 | Wiesener et al. |
| 2017/0360309 A1 | 12/2017 | Moore et al. |
| 2017/0361001 A1 | 12/2017 | Canatella et al. |
| 2017/0361011 A1 | 12/2017 | Muennich et al. |
| 2017/0363103 A1 | 12/2017 | Canatella et al. |
| 2017/0363210 A1 | 12/2017 | Durst et al. |
| 2017/0363620 A1 | 12/2017 | Beshiri et al. |
| 2017/0368246 A1 | 12/2017 | Criscione et al. |
| 2017/0370365 A1 | 12/2017 | Fritz et al. |
| 2018/0001003 A1 | 1/2018 | Moran et al. |
| 2018/0001007 A1 | 1/2018 | Stratton |
| 2018/0001012 A1 | 1/2018 | Ardehali |
| 2018/0001062 A1 | 1/2018 | O'Carrol et al. |
| 2018/0015214 A1 | 1/2018 | Lynch |
| 2018/0021494 A1 | 1/2018 | Muller et al. |
| 2018/0021495 A1 | 1/2018 | Muller et al. |
| 2018/0021497 A1 | 1/2018 | Nunez et al. |
| 2018/0028736 A1 | 2/2018 | Wong et al. |
| 2018/0035926 A1 | 2/2018 | Stafford |
| 2018/0040418 A1 | 2/2018 | Hansen et al. |
| 2018/0047282 A1 | 2/2018 | He et al. |
| 2018/0050139 A1 | 2/2018 | Siess et al. |
| 2018/0050140 A1 | 2/2018 | Siess et al. |
| 2018/0050142 A1 | 2/2018 | Siess et al. |
| 2018/0055383 A1 | 3/2018 | Manera |
| 2018/0055983 A1 | 3/2018 | Bourque |
| 2018/0058437 A1 | 3/2018 | Eilers et al. |
| 2018/0064862 A1 | 3/2018 | Keenan et al. |
| 2018/0071020 A1 | 3/2018 | Laufer et al. |
| 2018/0078159 A1 | 3/2018 | Edelman et al. |
| 2018/0085505 A1 | 3/2018 | Casas |
| 2018/0085507 A1 | 3/2018 | Casas et al. |
| 2018/0085509 A1 | 3/2018 | Petersen |

(56) References Cited

U.S. PATENT DOCUMENTS

| | | |
|---|---|---|
| 2018/0093026 A1 | 4/2018 | Angwin et al. |
| 2018/0097368 A1 | 4/2018 | Hansen |
| 2018/0099076 A1 | 4/2018 | Larose |
| 2018/0099078 A1 | 4/2018 | Tuseth et al. |
| 2018/0100507 A1 | 4/2018 | Wu et al. |
| 2018/0103611 A1 | 4/2018 | Mainini et al. |
| 2018/0103870 A1 | 4/2018 | Limaye et al. |
| 2018/0108275 A1 | 4/2018 | Newberry et al. |
| 2018/0110514 A1 | 4/2018 | Hoarau et al. |
| 2018/0114426 A1 | 4/2018 | Lee |
| 2018/0133380 A1 | 5/2018 | Liebing |
| 2018/0140759 A1 | 5/2018 | Kaiser et al. |
| 2018/0140801 A1 | 5/2018 | Voss et al. |
| 2018/0146968 A1 | 5/2018 | Nitzan et al. |
| 2018/0149164 A1 | 5/2018 | Siess |
| 2018/0149165 A1 | 5/2018 | Siess et al. |
| 2018/0154051 A1 | 6/2018 | Hossainy et al. |
| 2018/0154128 A1 | 6/2018 | Woo et al. |
| 2018/0161540 A1 | 6/2018 | Fantuzzi et al. |
| 2018/0161555 A1 | 6/2018 | Zhadkevich |
| 2018/0168469 A1 | 6/2018 | Granegger |
| 2018/0169313 A1 | 6/2018 | Schwammenthal et al. |
| 2018/0193543 A1 | 7/2018 | Sun |
| 2018/0193614 A1 | 7/2018 | Nitzan et al. |
| 2018/0193616 A1 | 7/2018 | Nitzan et al. |
| 2018/0200420 A1 | 7/2018 | Di Paola et al. |
| 2018/0200422 A1 | 7/2018 | Nguyen et al. |
| 2018/0202962 A1 | 7/2018 | Simmons et al. |
| 2018/0207334 A1 | 7/2018 | Siess |
| 2018/0207337 A1 | 7/2018 | Spence et al. |
| 2018/0207338 A1 | 7/2018 | Bluvshtein et al. |
| 2018/0228953 A1 | 8/2018 | Siess et al. |
| 2018/0228957 A1 | 8/2018 | Colella |
| 2018/0242891 A1 | 8/2018 | Bernstein et al. |
| 2018/0242976 A1 | 8/2018 | Kizuka |
| 2018/0243086 A1 | 8/2018 | Barbarino et al. |
| 2018/0243488 A1 | 8/2018 | Callaway et al. |
| 2018/0243489 A1 | 8/2018 | Haddadi |
| 2018/0243490 A1 | 8/2018 | Kallenbach et al. |
| 2018/0243492 A1 | 8/2018 | Salys |
| 2018/0250457 A1 | 9/2018 | Morello et al. |
| 2018/0250458 A1 | 9/2018 | Petersen et al. |
| 2018/0256242 A1 | 9/2018 | Bluvshtein et al. |
| 2018/0256794 A1 | 9/2018 | Rodefeld |
| 2018/0256795 A1 | 9/2018 | Schade et al. |
| 2018/0256797 A1 | 9/2018 | Schenck et al. |
| 2018/0256798 A1 | 9/2018 | Botterbusch et al. |
| 2018/0256859 A1 | 9/2018 | Korkuch |
| 2018/0264183 A1 | 9/2018 | Jahangir |
| 2018/0264184 A1 | 9/2018 | Jeffries et al. |
| 2018/0269692 A1 | 9/2018 | Petersen et al. |
| 2018/0280598 A1 | 10/2018 | Curran et al. |
| 2018/0280599 A1 | 10/2018 | Harjes et al. |
| 2018/0280600 A1 | 10/2018 | Harjes et al. |
| 2018/0280601 A1 | 10/2018 | Harjes et al. |
| 2018/0280604 A1 | 10/2018 | Hobro et al. |
| 2018/0289295 A1 | 10/2018 | Hoss et al. |
| 2018/0289876 A1 | 10/2018 | Nguyen et al. |
| 2018/0289877 A1 | 10/2018 | Schumacher et al. |
| 2018/0296572 A1 | 10/2018 | Deisher |
| 2019/0143018 A1 | 5/2019 | Salahieh et al. |

FOREIGN PATENT DOCUMENTS

| | | |
|---|---|---|
| CN | 1008307 B | 6/1990 |
| CN | 1053108 A | 7/1991 |
| CN | 1105103 A | 7/1995 |
| CN | 1146329 A | 4/1997 |
| CN | 1179708 A | 4/1998 |
| CN | 2326258 Y | 6/1999 |
| CN | 1222862 A | 7/1999 |
| CN | 1045058 C | 9/1999 |
| CN | 1235849 A | 11/1999 |
| CN | 2361290 Y | 2/2000 |
| CN | 1254598 A | 5/2000 |
| CN | 2386827 Y | 7/2000 |
| CN | 2412579 Y | 1/2001 |
| CN | 2417173 Y | 1/2001 |
| CN | 1310647 A | 8/2001 |
| CN | 1342497 A | 4/2002 |
| CN | 1088795 C | 8/2002 |
| CN | 2504815 Y | 8/2002 |
| CN | 1376523 A | 10/2002 |
| CN | 1097138 C | 12/2002 |
| CN | 1105581 C | 4/2003 |
| CN | 1421248 A | 6/2003 |
| CN | 2558386 Y | 7/2003 |
| CN | 1118304 C | 8/2003 |
| CN | 1436048 A | 8/2003 |
| CN | 1120729 C | 9/2003 |
| CN | 2574609 Y | 9/2003 |
| CN | 1140228 C | 3/2004 |
| CN | 1161581 C | 8/2004 |
| CN | 1167472 C | 9/2004 |
| CN | 1527906 A | 9/2004 |
| CN | 1559361 A | 1/2005 |
| CN | 1559626 A | 1/2005 |
| CN | 1572331 A | 2/2005 |
| CN | 1202871 C | 5/2005 |
| CN | 1679974 A | 10/2005 |
| CN | 1694338 A | 11/2005 |
| CN | 1705462 A | 12/2005 |
| CN | 1239133 C | 2/2006 |
| CN | 1239209 C | 2/2006 |
| CN | 2754637 Y | 2/2006 |
| CN | 1244381 C | 3/2006 |
| CN | 1249339 C | 4/2006 |
| CN | 2776418 Y | 5/2006 |
| CN | 2787222 Y | 6/2006 |
| CN | 1799652 A | 7/2006 |
| CN | 1806774 A | 7/2006 |
| CN | 1826463 A | 8/2006 |
| CN | 1833735 A | 9/2006 |
| CN | 1833736 A | 9/2006 |
| CN | 2831716 Y | 10/2006 |
| CN | 1874805 A | 12/2006 |
| CN | 1301583 C | 2/2007 |
| CN | 1921947 A | 2/2007 |
| CN | 2880096 Y | 3/2007 |
| CN | 2899800 Y | 5/2007 |
| CN | 101001765 A | 7/2007 |
| CN | 1329666 C | 8/2007 |
| CN | 101024098 A | 8/2007 |
| CN | 101031302 A | 9/2007 |
| CN | 101112628 A | 1/2008 |
| CN | 101121045 A | 2/2008 |
| CN | 101124002 A | 2/2008 |
| CN | 101132830 A | 2/2008 |
| CN | 100382855 C | 4/2008 |
| CN | 101256992 A | 9/2008 |
| CN | 100429406 C | 10/2008 |
| CN | 100439717 C | 12/2008 |
| CN | 100472042 C | 3/2009 |
| CN | 201208423 Y | 3/2009 |
| CN | 100488577 C | 5/2009 |
| CN | 201230980 Y | 5/2009 |
| CN | 201239369 Y | 5/2009 |
| CN | 201246310 Y | 5/2009 |
| CN | 101522115 A | 9/2009 |
| CN | 101534883 A | 9/2009 |
| CN | 201308666 Y | 9/2009 |
| CN | 101563605 A | 10/2009 |
| CN | 100558416 C | 11/2009 |
| CN | 100566765 C | 12/2009 |
| CN | 101595276 A | 12/2009 |
| CN | 101631578 A | 1/2010 |
| CN | 101652069 A | 2/2010 |
| CN | 101678025 A | 3/2010 |
| CN | 101687791 A | 3/2010 |
| CN | 101244296 B | 6/2010 |
| CN | 101730552 A | 6/2010 |
| CN | 101208058 B | 8/2010 |
| CN | 101808515 A | 8/2010 |
| CN | 101401981 B | 9/2010 |

(56) References Cited

FOREIGN PATENT DOCUMENTS

| | | | |
|---|---|---|---|
| CN | 101843528 A | 9/2010 |
| CN | 101232952 B2 | 11/2010 |
| CN | 101361994 B | 11/2010 |
| CN | 201618200 U | 11/2010 |
| CN | 201710717 U | 1/2011 |
| CN | 101417155 B | 2/2011 |
| CN | 101581307 B | 4/2011 |
| CN | 102065923 A | 5/2011 |
| CN | 101269245 B | 7/2011 |
| CN | 101618240 B | 8/2011 |
| CN | 102166379 A | 8/2011 |
| CN | 101484093 B | 9/2011 |
| CN | 102292053 A | 12/2011 |
| CN | 102422018 B | 4/2012 |
| CN | 102438673 A | 5/2012 |
| CN | 102475923 A | 5/2012 |
| CN | 202218993 U | 5/2012 |
| CN | 101983732 B | 7/2012 |
| CN | 102553005 A | 7/2012 |
| CN | 101590295 B | 8/2012 |
| CN | 101822854 B | 9/2012 |
| CN | 101822855 B | 9/2012 |
| CN | 101189431 B | 10/2012 |
| CN | 101810891 B | 10/2012 |
| CN | 102711894 A | 10/2012 |
| CN | 102869318 A | 1/2013 |
| CN | 102088920 B | 4/2013 |
| CN | 103026234 A | 4/2013 |
| CN | 103068417 A | 4/2013 |
| CN | 103172739 A | 6/2013 |
| CN | 101420993 B | 7/2013 |
| CN | 103206402 A | 7/2013 |
| CN | 103228300 A | 7/2013 |
| CN | 103356306 A | 10/2013 |
| CN | 103381277 A | 11/2013 |
| CN | 103432637 A | 12/2013 |
| CN | 103437951 A | 12/2013 |
| CN | 103446635 A | 12/2013 |
| CN | 103458832 A | 12/2013 |
| CN | 102319457 B | 1/2014 |
| CN | 103509116 A | 1/2014 |
| CN | 103541857 A | 1/2014 |
| CN | 103635212 A | 3/2014 |
| CN | 203507200 U | 4/2014 |
| CN | 203539803 U | 4/2014 |
| CN | 203591299 U | 5/2014 |
| CN | 102317629 B | 8/2014 |
| CN | 203756589 U | 8/2014 |
| CN | 104043153 A | 9/2014 |
| CN | 203829160 U | 9/2014 |
| CN | 104105511 A | 10/2014 |
| CN | 203935281 U | 11/2014 |
| CN | 104208763 A | 12/2014 |
| CN | 203971002 U | 12/2014 |
| CN | 204050452 U | 12/2014 |
| CN | 102271728 B | 1/2015 |
| CN | 102294057 B | 1/2015 |
| CN | 104271075 A | 1/2015 |
| CN | 102588255 B | 3/2015 |
| CN | 104470454 A | 3/2015 |
| CN | 102300501 B | 4/2015 |
| CN | 103055363 B | 4/2015 |
| CN | 104473676 A | 4/2015 |
| CN | 104524663 A | 4/2015 |
| CN | 204293210 U | 4/2015 |
| CN | 102686316 B | 5/2015 |
| CN | 104586469 A | 5/2015 |
| CN | 104602987 A | 5/2015 |
| CN | 102458275 B | 6/2015 |
| CN | 102458498 B | 6/2015 |
| CN | 104684607 A | 6/2015 |
| CN | 104721899 A | 6/2015 |
| CN | 204419151 U | 6/2015 |
| CN | 102397598 B | 7/2015 |
| CN | 103446634 B | 7/2015 |
| CN | 104758029 A | 7/2015 |
| CN | 104771797 A | 7/2015 |
| CN | 101868628 B | 8/2015 |
| CN | 102665784 B | 8/2015 |
| CN | 103706018 B | 9/2015 |
| CN | 104955420 A | 9/2015 |
| CN | 104984425 A | 10/2015 |
| CN | 104997550 A | 10/2015 |
| CN | 105007960 A | 10/2015 |
| CN | 105142719 A | 12/2015 |
| CN | 105208927 A | 12/2015 |
| CN | 102176933 B | 1/2016 |
| CN | 102947092 B | 1/2016 |
| CN | 103717837 B | 1/2016 |
| CN | 105228688 A | 1/2016 |
| CN | 105283149 A | 1/2016 |
| CN | 204972635 U | 1/2016 |
| CN | 103228232 B | 2/2016 |
| CN | 103355925 B | 2/2016 |
| CN | 105311692 A | 2/2016 |
| CN | 102257279 B | 3/2016 |
| CN | 102472719 B | 3/2016 |
| CN | 103154738 B | 3/2016 |
| CN | 105451787 A | 3/2016 |
| CN | 205083494 U | 3/2016 |
| CN | 103850979 B | 4/2016 |
| CN | 105477706 A | 4/2016 |
| CN | 105517589 A | 4/2016 |
| CN | 205163763 U | 4/2016 |
| CN | 103002833 B | 5/2016 |
| CN | 103861163 B | 5/2016 |
| CN | 105555204 A | 5/2016 |
| CN | 205215814 U | 5/2016 |
| CN | 102940911 B | 6/2016 |
| CN | 105641762 A | 6/2016 |
| CN | 105641763 A | 6/2016 |
| CN | 105662439 A | 6/2016 |
| CN | 105709287 A | 6/2016 |
| CN | 105722477 A | 6/2016 |
| CN | 205322884 U | 6/2016 |
| CN | 104069555 B | 7/2016 |
| CN | 105744915 A | 7/2016 |
| CN | 105790453 A | 7/2016 |
| CN | 105792780 A | 7/2016 |
| CN | 105792864 A | 7/2016 |
| CN | 103260666 B | 8/2016 |
| CN | 103732171 B | 8/2016 |
| CN | 103928971 B | 8/2016 |
| CN | 105833370 A | 8/2016 |
| CN | 205411785 U | 8/2016 |
| CN | 205460099 U | 8/2016 |
| CN | 205528886 U | 8/2016 |
| CN | 103889369 B | 9/2016 |
| CN | 104849482 B | 9/2016 |
| CN | 105980660 A | 9/2016 |
| CN | 106075621 A | 11/2016 |
| CN | 106102657 A | 11/2016 |
| CN | 205681272 U | 11/2016 |
| CN | 205698666 U | 11/2016 |
| CN | 205698725 U | 11/2016 |
| CN | 205753678 U | 11/2016 |
| CN | 106214288 A | 12/2016 |
| CN | 106256321 A | 12/2016 |
| CN | 205779766 U | 12/2016 |
| CN | 106334224 A | 1/2017 |
| CN | 205867186 U | 1/2017 |
| CN | 205876589 U | 1/2017 |
| CN | 103281971 B | 2/2017 |
| CN | 106390218 A | 2/2017 |
| CN | 103533970 B | 3/2017 |
| CN | 104826183 B | 3/2017 |
| CN | 106512117 A | 3/2017 |
| CN | 106581840 A | 4/2017 |
| CN | 104068947 B | 5/2017 |
| CN | 106620912 A | 5/2017 |
| CN | 106691363 A | 5/2017 |
| CN | 106716137 A | 5/2017 |
| CN | 106794293 A | 5/2017 |
| CN | 104225696 B | 6/2017 |

(56) References Cited

FOREIGN PATENT DOCUMENTS

| | | |
|---|---|---|
| CN | 104918578 B | 6/2017 |
| CN | 105915005 B | 6/2017 |
| CN | 106902404 A | 6/2017 |
| CN | 206325049 U | 7/2017 |
| CN | 206355093 U | 7/2017 |
| CN | 105377321 B | 8/2017 |
| CN | 107050543 A | 8/2017 |
| CN | 107050544 A | 8/2017 |
| CN | 107080870 A | 8/2017 |
| CN | 107080871 A | 8/2017 |
| CN | 107110875 A | 8/2017 |
| CN | 206414547 U | 8/2017 |
| CN | 206443963 U | 8/2017 |
| CN | 103930214 B | 9/2017 |
| CN | 104619361 B | 9/2017 |
| CN | 104936550 B | 9/2017 |
| CN | 105188618 B | 9/2017 |
| CN | 107115162 A | 9/2017 |
| CN | 107126588 A | 9/2017 |
| CN | 107134208 A | 9/2017 |
| CN | 107157623 A | 9/2017 |
| CN | 103857363 B | 10/2017 |
| CN | 104768500 B | 10/2017 |
| CN | 105008841 B | 10/2017 |
| CN | 105492036 B | 10/2017 |
| CN | 107252339 A | 10/2017 |
| CN | 107281567 A | 10/2017 |
| CN | 206592332 U | 10/2017 |
| CN | 107349484 A | 11/2017 |
| CN | 206660203 U | 11/2017 |
| CN | 105287050 B | 12/2017 |
| CN | 105597172 B | 12/2017 |
| CN | 105854097 B | 12/2017 |
| CN | 107412892 A | 12/2017 |
| CN | 107440681 A | 12/2017 |
| CN | 107496054 A | 12/2017 |
| CN | 104602647 B | 1/2018 |
| CN | 106061523 B | 1/2018 |
| CN | 107551341 A | 1/2018 |
| CN | 206934393 U | 1/2018 |
| CN | 107693868 A | 2/2018 |
| CN | 107693869 A | 2/2018 |
| CN | 107708765 A | 2/2018 |
| CN | 207018256 U | 2/2018 |
| CN | 106029120 B | 3/2018 |
| CN | 107753153 A | 3/2018 |
| CN | 107754071 A | 3/2018 |
| CN | 107798980 A | 3/2018 |
| CN | 107835826 A | 3/2018 |
| CN | 107837430 A | 3/2018 |
| CN | 107862963 A | 3/2018 |
| CN | 207125933 U | 3/2018 |
| CN | 207136890 U | 3/2018 |
| CN | 105120796 B | 4/2018 |
| CN | 105214153 B | 4/2018 |
| CN | 107865988 A | 4/2018 |
| CN | 107886825 A | 4/2018 |
| CN | 107913442 A | 4/2018 |
| CN | 107921195 A | 4/2018 |
| CN | 107923311 A | 4/2018 |
| CN | 108025120 A | 5/2018 |
| CN | 108025123 A | 5/2018 |
| CN | 108066834 A | 5/2018 |
| CN | 207410652 U | 5/2018 |
| CN | 104470579 B | 6/2018 |
| CN | 105188604 B | 6/2018 |
| CN | 105492909 B | 6/2018 |
| CN | 105498002 B | 6/2018 |
| CN | 106535824 B | 6/2018 |
| CN | 108136110 A | 6/2018 |
| CN | 108144146 A | 6/2018 |
| CN | 108175884 A | 6/2018 |
| CN | 106028807 B | 7/2018 |
| CN | 108273148 A | 7/2018 |
| CN | 108310486 A | 7/2018 |
| CN | 108348667 A | 7/2018 |
| CN | 207614108 U | 7/2018 |
| CN | 1063104101 B | 7/2018 |
| CN | 105640635 B | 8/2018 |
| CN | 105923112 B | 8/2018 |
| CN | 108367106 A | 8/2018 |
| CN | 108430533 A | 8/2018 |
| CN | 108457844 A | 8/2018 |
| CN | 108472138 A | 8/2018 |
| CN | 108472395 A | 8/2018 |
| CN | 108472424 A | 8/2018 |
| CN | 207708246 U | 8/2018 |
| CN | 207708250 U | 8/2018 |
| CN | 105407937 B | 9/2018 |
| CN | 105902298 B | 9/2018 |
| CN | 106420113 B | 9/2018 |
| CN | 106510902 B | 9/2018 |
| CN | 108525039 A | 9/2018 |
| CN | 108525040 A | 9/2018 |
| CN | 108601653 A | 9/2018 |
| CN | 108601872 A | 9/2018 |
| CN | 108601874 A | 9/2018 |
| CN | 108601875 A | 9/2018 |
| CN | 207924984 U | 9/2018 |
| CN | 106377810 B | 10/2018 |
| EP | 96495 B1 | 9/1986 |
| EP | 79373 B1 | 12/1986 |
| EP | 54049 B1 | 1/1988 |
| EP | 292510 A4 | 8/1989 |
| EP | 167562 B1 | 4/1990 |
| EP | 230532 B1 | 9/1990 |
| EP | 241950 B1 | 12/1990 |
| EP | 129779 B1 | 4/1991 |
| EP | 202649 B1 | 8/1991 |
| EP | 445782 A1 | 9/1991 |
| EP | 464714 A1 | 1/1992 |
| EP | 293592 B1 | 11/1992 |
| EP | 297723 B1 | 8/1993 |
| EP | 396575 B1 | 3/1994 |
| EP | 397668 B1 | 3/1994 |
| EP | 593574 A1 | 4/1994 |
| EP | 378251 B1 | 6/1994 |
| EP | 605621 A1 | 7/1994 |
| EP | 467999 B1 | 8/1994 |
| EP | 350282 B1 | 11/1994 |
| EP | 478635 B1 | 12/1994 |
| EP | 397720 B1 | 3/1995 |
| EP | 421558 B1 | 4/1995 |
| EP | 364799 B1 | 5/1995 |
| EP | 660726 A1 | 7/1995 |
| EP | 672386 A1 | 9/1995 |
| EP | 349581 B1 | 1/1996 |
| EP | 464973 B1 | 1/1996 |
| EP | 505270 B1 | 1/1996 |
| EP | 480101 B1 | 5/1996 |
| EP | 583781 B1 | 5/1996 |
| EP | 583012 B1 | 7/1996 |
| EP | 756500 A1 | 2/1997 |
| EP | 767318 A2 | 4/1997 |
| EP | 788808 A2 | 8/1997 |
| EP | 799060 A1 | 10/1997 |
| EP | 823567 A1 | 2/1998 |
| EP | 832357 A1 | 4/1998 |
| EP | 841917 A1 | 5/1998 |
| EP | 560000 B1 | 9/1998 |
| EP | 879012 A1 | 11/1998 |
| EP | 925078 A1 | 6/1999 |
| EP | 807141 B1 | 7/1999 |
| EP | 681654 B1 | 9/1999 |
| EP | 958066 A1 | 11/1999 |
| EP | 964718 B1 | 12/1999 |
| EP | 725657 B1 | 2/2000 |
| EP | 986409 A1 | 3/2000 |
| EP | 1007140 A1 | 6/2000 |
| EP | 1009466 A1 | 6/2000 |
| EP | 1027898 A1 | 8/2000 |
| EP | 1032437 A1 | 9/2000 |
| EP | 1045708 A1 | 10/2000 |
| EP | 1059885 A2 | 12/2000 |

(56) References Cited

FOREIGN PATENT DOCUMENTS

| | | |
|---|---|---|
| EP | 746712 B1 | 10/2001 |
| EP | 1139862 A1 | 10/2001 |
| EP | 1147317 A1 | 10/2001 |
| EP | 1148900 A1 | 10/2001 |
| EP | 699447 B1 | 11/2001 |
| EP | 591896 B1 | 2/2002 |
| EP | 731664 B1 | 2/2002 |
| EP | 797734 B1 | 2/2002 |
| EP | 1217954 A1 | 7/2002 |
| EP | 1231981 A1 | 8/2002 |
| EP | 950057 B1 | 11/2002 |
| EP | 751769 B1 | 1/2003 |
| EP | 1278461 A1 | 1/2003 |
| EP | 860046 B1 | 2/2003 |
| EP | 597881 B2 | 3/2003 |
| EP | 732949 B1 | 3/2003 |
| EP | 814701 B1 | 4/2003 |
| EP | 898479 B1 | 5/2003 |
| EP | 905379 B1 | 5/2003 |
| EP | 655625 B1 | 7/2003 |
| EP | 764448 B1 | 7/2003 |
| EP | 768091 B1 | 7/2003 |
| EP | 825888 B1 | 12/2003 |
| EP | 1379197 A1 | 1/2004 |
| EP | 1382366 A1 | 1/2004 |
| EP | 868145 B1 | 2/2004 |
| EP | 895480 B1 | 5/2004 |
| EP | 1441777 A2 | 8/2004 |
| EP | 916359 B1 | 9/2004 |
| EP | 1482999 A1 | 12/2004 |
| EP | 1291027 B1 | 3/2005 |
| EP | 877633 B1 | 7/2005 |
| EP | 611228 B2 | 8/2005 |
| EP | 1212516 B1 | 10/2005 |
| EP | 1597457 A2 | 11/2005 |
| EP | 1261385 B1 | 2/2006 |
| EP | 1648309 A1 | 4/2006 |
| EP | 1354606 B1 | 6/2006 |
| EP | 1663081 A1 | 6/2006 |
| EP | 1321166 B1 | 7/2006 |
| EP | 1191956 B1 | 9/2006 |
| EP | 1722767 A2 | 11/2006 |
| EP | 1070510 B1 | 1/2007 |
| EP | 1317295 B1 | 1/2007 |
| EP | 1327455 B1 | 1/2007 |
| EP | 1776095 A1 | 4/2007 |
| EP | 1807148 A2 | 7/2007 |
| EP | 11416701 B1 | 7/2007 |
| EP | 1827448 A1 | 9/2007 |
| EP | 1374928 B1 | 12/2007 |
| EP | 1877133 A2 | 1/2008 |
| EP | 1379294 B1 | 5/2008 |
| EP | 1930034 A1 | 6/2008 |
| EP | 1318848 B1 | 7/2008 |
| EP | 1356859 B1 | 8/2008 |
| EP | 1955725 A2 | 8/2008 |
| EP | 2058017 A2 | 5/2009 |
| EP | 1731957 B1 | 8/2009 |
| EP | 1173238 B1 | 10/2009 |
| EP | 2043553 B1 | 3/2010 |
| EP | 2158491 A2 | 3/2010 |
| EP | 2178580 A2 | 4/2010 |
| EP | 2182844 A1 | 5/2010 |
| EP | 2194278 A1 | 6/2010 |
| EP | 1471952 B1 | 7/2010 |
| EP | 2207578 A1 | 7/2010 |
| EP | 2216059 A1 | 8/2010 |
| EP | 2218469 A1 | 8/2010 |
| EP | 2219699 A1 | 8/2010 |
| EP | 2222635 A2 | 9/2010 |
| EP | 2222788 A1 | 9/2010 |
| EP | 2229965 A1 | 9/2010 |
| EP | 2235204 A1 | 10/2010 |
| EP | 1280581 B1 | 11/2010 |
| EP | 2246078 A1 | 11/2010 |
| EP | 2248544 A1 | 11/2010 |
| EP | 2252337 A1 | 11/2010 |
| EP | 2266640 A1 | 12/2010 |
| EP | 2269670 A1 | 1/2011 |
| EP | 2297583 A2 | 3/2011 |
| EP | 2298371 A1 | 3/2011 |
| EP | 2298372 A1 | 3/2011 |
| EP | 2298373 A1 | 3/2011 |
| EP | 2299119 A1 | 3/2011 |
| EP | 1464348 B1 | 4/2011 |
| EP | 2314330 A1 | 4/2011 |
| EP | 2314331 A1 | 4/2011 |
| EP | 2338539 A1 | 6/2011 |
| EP | 2338540 A1 | 6/2011 |
| EP | 2338541 A1 | 6/2011 |
| EP | 1654027 B1 | 7/2011 |
| EP | 2343091 A1 | 7/2011 |
| EP | 2347778 A1 | 7/2011 |
| EP | 1812094 B1 | 8/2011 |
| EP | 2349385 A1 | 8/2011 |
| EP | 2353626 A1 | 8/2011 |
| EP | 2356458 A1 | 8/2011 |
| EP | 2363157 A1 | 9/2011 |
| EP | 2366412 A2 | 9/2011 |
| EP | 1907049 B1 | 11/2011 |
| EP | 2388027 A1 | 11/2011 |
| EP | 2388029 A1 | 11/2011 |
| EP | 2399639 A1 | 12/2011 |
| EP | 1514571 B1 | 1/2012 |
| EP | 2407185 A1 | 1/2012 |
| EP | 2407186 A1 | 1/2012 |
| EP | 2407187 A1 | 1/2012 |
| EP | 2422735 A1 | 2/2012 |
| EP | 2322600 B1 | 3/2012 |
| EP | 2429603 A2 | 3/2012 |
| EP | 2459269 A1 | 6/2012 |
| EP | 2497521 A1 | 9/2012 |
| EP | 2140892 B1 | 10/2012 |
| EP | 2505228 A1 | 10/2012 |
| EP | 2150811 B1 | 1/2013 |
| EP | 1833529 B1 | 2/2013 |
| EP | 2554191 A1 | 2/2013 |
| EP | 2277463 B1 | 3/2013 |
| EP | 2564771 A1 | 3/2013 |
| EP | 2151257 B1 | 4/2013 |
| EP | 2575922 A2 | 4/2013 |
| EP | 1623730 B1 | 5/2013 |
| EP | 2606919 A1 | 6/2013 |
| EP | 2606920 A1 | 6/2013 |
| EP | 2607712 A1 | 6/2013 |
| EP | 1919550 B1 | 7/2013 |
| EP | 2620173 A1 | 7/2013 |
| EP | 1331017 B1 | 8/2013 |
| EP | 2101840 B1 | 9/2013 |
| EP | 2401003 B1 | 10/2013 |
| EP | 2654878 A2 | 10/2013 |
| EP | 2654883 A2 | 10/2013 |
| EP | 2671083 A1 | 12/2013 |
| EP | 1412001 B1 | 1/2014 |
| EP | 1942965 B1 | 1/2014 |
| EP | 2231222 B1 | 2/2014 |
| EP | 2697890 A2 | 2/2014 |
| EP | 1017433 B1 | 3/2014 |
| EP | 1629855 B1 | 4/2014 |
| EP | 2736581 A2 | 6/2014 |
| EP | 2744460 A1 | 6/2014 |
| EP | 2745869 A1 | 6/2014 |
| EP | 1485613 B1 | 7/2014 |
| EP | 1605988 B1 | 8/2014 |
| EP | 2792696 A2 | 10/2014 |
| EP | 2195043 B1 | 12/2014 |
| EP | 1962949 B1 | 2/2015 |
| EP | 2030641 B1 | 2/2015 |
| EP | 2643927 B1 | 4/2015 |
| EP | 2868331 A2 | 5/2015 |
| EP | 1460972 B1 | 6/2015 |
| EP | 2150569 B1 | 6/2015 |
| EP | 2152783 B1 | 6/2015 |
| EP | 2345439 B1 | 6/2015 |

(56) References Cited

FOREIGN PATENT DOCUMENTS

| | | |
|---|---|---|
| EP | 2895215 A2 | 7/2015 |
| EP | 1761306 B1 | 8/2015 |
| EP | 2663347 B1 | 8/2015 |
| EP | 2209508 B1 | 9/2015 |
| EP | 2915129 A1 | 9/2015 |
| EP | 2920421 A2 | 9/2015 |
| EP | 2533732 B1 | 11/2015 |
| EP | 1317305 B1 | 12/2015 |
| EP | 1339443 B1 | 1/2016 |
| EP | 2967284 A1 | 1/2016 |
| EP | 2967547 A1 | 1/2016 |
| EP | 2984731 A1 | 2/2016 |
| EP | 2167158 B1 | 3/2016 |
| EP | 2061531 B1 | 4/2016 |
| EP | 2519274 B1 | 4/2016 |
| EP | 1996252 B1 | 5/2016 |
| EP | 2464395 B1 | 5/2016 |
| EP | 3047873 A1 | 7/2016 |
| EP | 3047911 A1 | 7/2016 |
| EP | 2643053 B1 | 8/2016 |
| EP | 2734251 B1 | 8/2016 |
| EP | 3050537 A1 | 8/2016 |
| EP | 1942128 B1 | 9/2016 |
| EP | 2099509 B1 | 9/2016 |
| EP | 2719403 B1 | 9/2016 |
| EP | 3072210 A1 | 9/2016 |
| EP | 3072211 A1 | 9/2016 |
| EP | 2405140 B1 | 10/2016 |
| EP | 2197507 B1 | 11/2016 |
| EP | 2538086 B1 | 11/2016 |
| EP | 3086834 A1 | 11/2016 |
| EP | 2806911 B1 | 12/2016 |
| EP | 3110468 A1 | 1/2017 |
| EP | 3113808 A1 | 1/2017 |
| EP | 3119452 A1 | 1/2017 |
| EP | 3120811 A2 | 1/2017 |
| EP | 3131595 A1 | 2/2017 |
| EP | 3131596 A1 | 2/2017 |
| EP | 3131599 A1 | 2/2017 |
| EP | 3131600 A1 | 2/2017 |
| EP | 3131615 A1 | 2/2017 |
| EP | 2585129 B1 | 3/2017 |
| EP | 2594799 B1 | 3/2017 |
| EP | 3146987 A1 | 3/2017 |
| EP | 3157597 A1 | 4/2017 |
| EP | 3173110 A1 | 5/2017 |
| EP | 2825107 B1 | 7/2017 |
| EP | 3185924 A1 | 7/2017 |
| EP | 3185925 A1 | 7/2017 |
| EP | 3189526 A1 | 7/2017 |
| EP | 3191164 A1 | 7/2017 |
| EP | 2618001 B1 | 8/2017 |
| EP | 3197602 A1 | 8/2017 |
| EP | 3198677 A1 | 8/2017 |
| EP | 3204989 A1 | 8/2017 |
| EP | 3212250 A1 | 9/2017 |
| EP | 3219339 A1 | 9/2017 |
| EP | 3223880 A1 | 10/2017 |
| EP | 3232948 A1 | 10/2017 |
| EP | 1885409 B1 | 11/2017 |
| EP | 2292282 B1 | 11/2017 |
| EP | 2945661 B1 | 11/2017 |
| EP | 3238764 A1 | 11/2017 |
| EP | 3244814 A1 | 11/2017 |
| EP | 3247420 A1 | 11/2017 |
| EP | 3247421 A2 | 11/2017 |
| EP | 3248628 A1 | 11/2017 |
| EP | 2136861 B1 | 12/2017 |
| EP | 3256183 A1 | 12/2017 |
| EP | 3256184 A1 | 12/2017 |
| EP | 3256185 A1 | 12/2017 |
| EP | 3256186 A1 | 12/2017 |
| EP | 3007742 B1 | 1/2018 |
| EP | 3277200 A1 | 2/2018 |
| EP | 3287155 A1 | 2/2018 |
| EP | 2482916 B1 | 3/2018 |
| EP | 2948202 B1 | 3/2018 |
| EP | 3294367 A1 | 3/2018 |
| EP | 2945662 B1 | 4/2018 |
| EP | 3310409 A1 | 4/2018 |
| EP | 3222301 B1 | 5/2018 |
| EP | 3222302 B1 | 5/2018 |
| EP | 3313471 A1 | 5/2018 |
| EP | 3324840 A1 | 5/2018 |
| EP | 3325035 A1 | 5/2018 |
| EP | 3326487 A1 | 5/2018 |
| EP | 1789129 B1 | 6/2018 |
| EP | 1990358 B1 | 6/2018 |
| EP | 3329953 A1 | 6/2018 |
| EP | 3335647 A2 | 6/2018 |
| EP | 3341069 A1 | 7/2018 |
| EP | 3349839 A1 | 7/2018 |
| EP | 2219698 B1 | 8/2018 |
| EP | 2890420 B1 | 8/2018 |
| EP | 3352808 A1 | 8/2018 |
| EP | 3352835 A1 | 8/2018 |
| EP | 3360233 A1 | 8/2018 |
| EP | 3360515 A1 | 8/2018 |
| EP | 1534381 B1 | 9/2018 |
| EP | 3108909 B1 | 9/2018 |
| EP | 3377001 A1 | 9/2018 |
| EP | 3377002 A1 | 9/2018 |
| EP | 3377134 A1 | 9/2018 |
| EP | 3377135 A1 | 9/2018 |
| EP | 3377136 A1 | 9/2018 |
| EP | 2249746 B1 | 10/2018 |
| EP | 2988795 B1 | 10/2018 |
| EP | 3383300 A1 | 10/2018 |
| EP | 3383448 A1 | 10/2018 |
| EP | 3388005 A1 | 10/2018 |
| JP | 64-52472 A | 2/1989 |
| JP | 02289241 A | 11/1990 |
| JP | 04176471 A | 6/1992 |
| JP | 04224760 A | 8/1992 |
| JP | 11062856 A | 3/1999 |
| JP | H11-062856 A | 3/1999 |
| JP | 02888609 B2 | 5/1999 |
| JP | 02927460 B2 | 7/1999 |
| JP | H11-244376 A | 9/1999 |
| JP | 2000102604 A | 4/2000 |
| JP | 2000107281 A | 4/2000 |
| JP | 2000283062 A | 10/2000 |
| JP | 03131696 B2 | 2/2001 |
| JP | 2001061957 A | 3/2001 |
| JP | 2001090687 A | 4/2001 |
| JP | 03174338 B2 | 6/2001 |
| JP | 2001173402 A | 6/2001 |
| JP | 03278160 B2 | 4/2002 |
| JP | 2002191123 A | 7/2002 |
| JP | 03313061 B2 | 8/2002 |
| JP | 2003047656 A | 2/2003 |
| JP | 2003070906 A | 3/2003 |
| JP | 2003205030 A | 7/2003 |
| JP | 2004011525 A | 1/2004 |
| JP | 2004016426 A | 1/2004 |
| JP | 2004028102 A | 1/2004 |
| JP | 2004073400 A | 3/2004 |
| JP | 2004209240 A | 7/2004 |
| JP | 2004278375 A | 10/2004 |
| JP | 03612581 B2 | 1/2005 |
| JP | 2005058617 A | 3/2005 |
| JP | 2005192687 A | 7/2005 |
| JP | 2005199076 A | 7/2005 |
| JP | 2005348996 A | 12/2005 |
| JP | 2006000631 A | 1/2006 |
| JP | 03786289 B2 | 6/2006 |
| JP | 03803417 B2 | 8/2006 |
| JP | 2006280571 A | 10/2006 |
| JP | 03854972 B2 | 12/2006 |
| JP | 2007044302 A | 2/2007 |
| JP | 2007075541 A | 3/2007 |
| JP | 2007089607 A | 4/2007 |
| JP | 2007089973 A | 4/2007 |
| JP | 2007236564 A | 9/2007 |

(56) References Cited

FOREIGN PATENT DOCUMENTS

| | | |
|---|---|---|
| JP | 04016441 B2 | 12/2007 |
| JP | 04022372 B2 | 12/2007 |
| JP | 2008018242 A | 1/2008 |
| JP | 04051812 B2 | 2/2008 |
| JP | 04072721 B2 | 4/2008 |
| JP | 04077902 B2 | 4/2008 |
| JP | 04078245 B2 | 4/2008 |
| JP | 04084060 B2 | 4/2008 |
| JP | 04086185 B2 | 5/2008 |
| JP | 04108054 B2 | 6/2008 |
| JP | 04121709 B2 | 7/2008 |
| JP | 04163384 B2 | 10/2008 |
| JP | 04179634 B2 | 11/2008 |
| JP | 2008264586 A | 11/2008 |
| JP | 04198986 B2 | 12/2008 |
| JP | 04209412 B2 | 1/2009 |
| JP | 2009090882 A | 4/2009 |
| JP | 04279494 B2 | 6/2009 |
| JP | 04308723 B2 | 8/2009 |
| JP | 2009178570 A | 8/2009 |
| JP | 2009254436 A | 11/2009 |
| JP | 2009273214 A | 11/2009 |
| JP | 04387106 B2 | 12/2009 |
| JP | 04391680 B2 | 12/2009 |
| JP | 04414925 B2 | 2/2010 |
| JP | 04440499 B2 | 3/2010 |
| JP | 04467187 B2 | 5/2010 |
| JP | 04468965 B2 | 5/2010 |
| JP | 04484320 B2 | 6/2010 |
| JP | 04512150 B2 | 7/2010 |
| JP | 2010158532 A | 7/2010 |
| JP | 04523961 B2 | 8/2010 |
| JP | 04523962 B2 | 8/2010 |
| JP | 04548450 B2 | 9/2010 |
| JP | 04549407 B2 | 9/2010 |
| JP | 2010246941 A | 11/2010 |
| JP | 04611364 B2 | 1/2011 |
| JP | 04611365 B2 | 1/2011 |
| JP | 04646393 B2 | 3/2011 |
| JP | 04655231 B2 | 3/2011 |
| JP | 04656332 B2 | 3/2011 |
| JP | 04674978 B2 | 4/2011 |
| JP | 2011072533 A | 4/2011 |
| JP | 2011116765 A | 6/2011 |
| JP | 04728351 B1 | 7/2011 |
| JP | 04741242 B2 | 8/2011 |
| JP | 04741489 B2 | 8/2011 |
| JP | 2011161401 A | 8/2011 |
| JP | 04795536 B2 | 10/2011 |
| JP | 04851333 B2 | 1/2012 |
| JP | 04865825 B2 | 2/2012 |
| JP | 04881154 B2 | 2/2012 |
| JP | 04897811 B2 | 3/2012 |
| JP | 04907028 B2 | 3/2012 |
| JP | 04908737 B2 | 4/2012 |
| JP | 04964854 B2 | 7/2012 |
| JP | 04987999 B2 | 8/2012 |
| JP | 05047447 B2 | 10/2012 |
| JP | 05048749 B2 | 10/2012 |
| JP | 05093869 B2 | 12/2012 |
| JP | 05102033 B2 | 12/2012 |
| JP | 05164558 B2 | 3/2013 |
| JP | 05185629 B2 | 4/2013 |
| JP | 05193059 B2 | 5/2013 |
| JP | 05197636 B2 | 5/2013 |
| JP | 2013078564 A | 5/2013 |
| JP | 05215580 B2 | 6/2013 |
| JP | 05267227 B2 | 8/2013 |
| JP | 05286268 B2 | 9/2013 |
| JP | 2013192711 A | 9/2013 |
| JP | 2014004303 A | 1/2014 |
| JP | 05427620 B2 | 2/2014 |
| JP | 05429714 B2 | 2/2014 |
| JP | 05440528 B2 | 3/2014 |
| JP | 05440529 B2 | 3/2014 |
| JP | 05461710 B2 | 4/2014 |
| JP | 05500348 B2 | 5/2014 |
| JP | 2014114784 A | 6/2014 |
| JP | 05539484 B2 | 7/2014 |
| JP | 05557175 B2 | 7/2014 |
| JP | 05590213 B2 | 9/2014 |
| JP | 05596974 B2 | 10/2014 |
| JP | 05611948 B2 | 10/2014 |
| JP | 05633512 B2 | 12/2014 |
| JP | 05656835 B2 | 1/2015 |
| JP | 05673795 B2 | 2/2015 |
| JP | 05675786 B2 | 2/2015 |
| JP | 05676118 B2 | 2/2015 |
| JP | 05701848 B2 | 4/2015 |
| JP | 05711245 B2 | 4/2015 |
| JP | 05750492 B2 | 7/2015 |
| JP | 05781597 B2 | 9/2015 |
| JP | 2015159947 A | 9/2015 |
| JP | 05837162 B2 | 12/2015 |
| JP | 05868180 B2 | 2/2016 |
| JP | 05894116 B2 | 3/2016 |
| JP | 05894678 B2 | 3/2016 |
| JP | 2016028764 A | 3/2016 |
| JP | 2016182342 A | 10/2016 |
| JP | 06034858 B2 | 11/2016 |
| JP | 06038018 B2 | 12/2016 |
| JP | 06054106 B2 | 12/2016 |
| JP | 2016202553 A | 12/2016 |
| JP | 06083929 B2 | 2/2017 |
| JP | 2017035323 A | 2/2017 |
| JP | 2017517306 A | 6/2017 |
| JP | 2017127675 A | 7/2017 |
| JP | 06178666 B2 | 8/2017 |
| JP | 2017159083 A | 9/2017 |
| JP | 06220867 B2 | 10/2017 |
| JP | 06236451 B2 | 11/2017 |
| JP | 06267625 B2 | 1/2018 |
| JP | 2018020199 A | 2/2018 |
| JP | 06295204 B2 | 3/2018 |
| JP | 06329358 B2 | 5/2018 |
| JP | 06339371 B2 | 6/2018 |
| JP | 06345112 B2 | 6/2018 |
| JP | 06353787 B2 | 7/2018 |
| JP | 06382285 B2 | 8/2018 |
| JP | 2018122146 A | 8/2018 |
| JP | 2018523541 A | 8/2018 |
| WO | WO87/002894 A2 | 5/1987 |
| WO | WO88/009874 A1 | 12/1988 |
| WO | WO92/002263 A1 | 2/1992 |
| WO | WO92/003181 A1 | 3/1992 |
| WO | WO95/031196 A1 | 11/1995 |
| WO | WO96/016684 A1 | 6/1996 |
| WO | WO98/042984 A1 | 10/1998 |
| WO | WO00/019097 A1 | 4/2000 |
| WO | WO00/027446 A1 | 5/2000 |
| WO | WO00/035515 A1 | 6/2000 |
| WO | WO01/041070 A1 | 6/2001 |
| WO | WO01/074419 A1 | 10/2001 |
| WO | WO01/087176 A1 | 11/2001 |
| WO | WO01/095813 A1 | 12/2001 |
| WO | WO02/053226 A2 | 7/2002 |
| WO | WO02/070039 A2 | 9/2002 |
| WO | WO02/072000 A1 | 9/2002 |
| WO | WO02/081021 A1 | 10/2002 |
| WO | WO03/061727 A2 | 7/2003 |
| WO | WO03/094716 A1 | 11/2003 |
| WO | WO03/103745 A2 | 12/2003 |
| WO | WO2004/026394 A1 | 4/2004 |
| WO | WO2004/034034 A1 | 4/2004 |
| WO | WO2004/088480 A2 | 10/2004 |
| WO | WO2004/098677 A1 | 11/2004 |
| WO | WO2005/020848 A2 | 3/2005 |
| WO | WO2005/033671 A1 | 4/2005 |
| WO | WO2005/037348 A1 | 4/2005 |
| WO | WO2005/054680 A1 | 6/2005 |
| WO | WO2005/108796 A1 | 11/2005 |
| WO | WO2006/040252 A1 | 4/2006 |
| WO | WO2006/053384 A1 | 5/2006 |
| WO | WO2006/081255 A2 | 8/2006 |

(56) References Cited

FOREIGN PATENT DOCUMENTS

| | | |
|---|---|---|
| WO | WO2006/121698 A2 | 11/2006 |
| WO | WO2007/008907 A2 | 1/2007 |
| WO | WO2007/033933 A1 | 3/2007 |
| WO | WO2007/053881 A1 | 5/2007 |
| WO | WO2007/065408 A2 | 6/2007 |
| WO | WO2007/092494 A2 | 8/2007 |
| WO | WO2007/105842 A1 | 9/2007 |
| WO | WO2007/146231 A2 | 12/2007 |
| WO | WO2008/005747 A2 | 1/2008 |
| WO | WO2008/008427 A2 | 1/2008 |
| WO | WO2008/088874 A2 | 7/2008 |
| WO | WO2008/102015 A1 | 8/2008 |
| WO | WO2008/121143 A1 | 10/2008 |
| WO | WO2008/121145 A1 | 10/2008 |
| WO | WO2008/137237 A2 | 11/2008 |
| WO | WO2008/140034 A1 | 11/2008 |
| WO | WO2009/017549 A1 | 2/2009 |
| WO | WO2009035581 A1 | 3/2009 |
| WO | WO2009/046789 A1 | 4/2009 |
| WO | WO2009/075668 A2 | 6/2009 |
| WO | WO2010/025411 A2 | 3/2010 |
| WO | WO2011/003043 A1 | 1/2011 |
| WO | WO2011/024928 A1 | 3/2011 |
| WO | WO2011/035925 A1 | 3/2011 |
| WO | WO2011/039091 A1 | 4/2011 |
| WO | WO2011/081629 A1 | 7/2011 |
| WO | WO2011/082212 A1 | 7/2011 |
| WO | WO2011/085040 A1 | 7/2011 |
| WO | WO2011/117566 A1 | 9/2011 |
| WO | WO2011/119060 A2 | 9/2011 |
| WO | WO2012/051454 A2 | 4/2012 |
| WO | WO2012/064674 A1 | 5/2012 |
| WO | WO2012/075152 A1 | 6/2012 |
| WO | WO2012/075262 A1 | 6/2012 |
| WO | WO2012/087811 A2 | 6/2012 |
| WO | WO2012/094535 A2 | 7/2012 |
| WO | WO2012/094641 A2 | 7/2012 |
| WO | WO2012/112129 A1 | 8/2012 |
| WO | WO2013/034547 A1 | 3/2013 |
| WO | WO2013/093058 A1 | 6/2013 |
| WO | WO2013/127182 A1 | 9/2013 |
| WO | WO2013/134319 A1 | 9/2013 |
| WO | WO2013/148560 A1 | 10/2013 |
| WO | WO2013/148697 A1 | 10/2013 |
| WO | WO2014/070458 A1 | 5/2014 |
| WO | WO2014/096408 A1 | 6/2014 |
| WO | WO2014/106635 A1 | 7/2014 |
| WO | WO2014/116639 A1 | 7/2014 |
| WO | WO2014/142754 A1 | 9/2014 |
| WO | WO2014/143593 A1 | 9/2014 |
| WO | WO2014/164136 A1 | 10/2014 |
| WO | WO2014/164292 A1 | 10/2014 |
| WO | WO2014/166128 A1 | 10/2014 |
| WO | WO2014/169023 A2 | 10/2014 |
| WO | WO2015/119705 A1 | 8/2015 |
| WO | WO2015/160943 A1 | 10/2015 |
| WO | WO2015/160979 A1 | 10/2015 |
| WO | WO2015/171156 A1 | 11/2015 |
| WO | WO2015/175711 A1 | 11/2015 |
| WO | WO2015/175718 A1 | 11/2015 |
| WO | WO2015/187659 A2 | 12/2015 |
| WO | WO2016/100600 A2 | 6/2016 |
| WO | WO2016/113266 A1 | 7/2016 |
| WO | WO2016/116630 A2 | 7/2016 |
| WO | WO2016/185473 A1 | 11/2016 |
| WO | WO2017/001358 A1 | 1/2017 |
| WO | WO2017/011257 A1 | 1/2017 |
| WO | WO2017/032751 A1 | 3/2017 |
| WO | WO2017/048733 A1 | 3/2017 |
| WO | WO2017/060254 A1 | 4/2017 |
| WO | WO2017/060257 A1 | 4/2017 |
| WO | WO2017/075322 A1 | 5/2017 |
| WO | WO2017/087380 A1 | 5/2017 |
| WO | WO2017/120453 A1 | 7/2017 |
| WO | WO2017/133425 A1 | 8/2017 |
| WO | WO2017/134657 A1 | 8/2017 |
| WO | WO2017/139113 A1 | 8/2017 |
| WO | WO2017/139246 A1 | 8/2017 |
| WO | WO2017/147082 A1 | 8/2017 |
| WO | WO2017/147103 A1 | 8/2017 |
| WO | WO2017/147291 A1 | 8/2017 |
| WO | WO2017/151987 A1 | 9/2017 |
| WO | WO2017/156386 A1 | 9/2017 |
| WO | WO2017/159849 A1 | 9/2017 |
| WO | WO2017/165372 A1 | 9/2017 |
| WO | WO2017/178904 A1 | 10/2017 |
| WO | WO2017/183124 A1 | 10/2017 |
| WO | WO2017/190155 A2 | 11/2017 |
| WO | WO2017/192119 A1 | 11/2017 |
| WO | WO2017/196271 A1 | 11/2017 |
| WO | WO2017/205909 A1 | 12/2017 |
| WO | WO2017/210318 A2 | 12/2017 |
| WO | WO2017/214118 A1 | 12/2017 |
| WO | WO2017/214183 A1 | 12/2017 |
| WO | WO2017/217946 A1 | 12/2017 |
| WO | WO2018/007120 A1 | 1/2018 |
| WO | WO2018/007471 A1 | 1/2018 |
| WO | WO2018/017678 A1 | 1/2018 |
| WO | WO2018/017683 A1 | 1/2018 |
| WO | WO2018/017716 A1 | 1/2018 |
| WO | WO2018/026764 A1 | 2/2018 |
| WO | WO2018/026769 A1 | 2/2018 |
| WO | WO2018/031741 A1 | 2/2018 |
| WO | WO2018/035069 A1 | 2/2018 |
| WO | WO2018/039124 A1 | 3/2018 |
| WO | WO2018/039326 A1 | 3/2018 |
| WO | WO2018/041963 A1 | 3/2018 |
| WO | WO2018/045299 A1 | 3/2018 |
| WO | WO2018/051091 A1 | 3/2018 |
| WO | WO2018/052482 A1 | 3/2018 |
| WO | WO2018/057482 A1 | 3/2018 |
| WO | WO2018/057563 A1 | 3/2018 |
| WO | WO2018/061002 A1 | 4/2018 |
| WO | WO2018/064437 A1 | 4/2018 |
| WO | WO2018/067410 A1 | 4/2018 |
| WO | WO2018/073150 A1 | 4/2018 |
| WO | WO2018/078370 A1 | 5/2018 |
| WO | WO2018/078615 A1 | 5/2018 |
| WO | WO2018/082987 A1 | 5/2018 |
| WO | WO2018/088939 A1 | 5/2018 |
| WO | WO2018/089970 A1 | 5/2018 |
| WO | WO2018/093663 A1 | 5/2018 |
| WO | WO2018/096531 A1 | 5/2018 |
| WO | WO2018/118756 A1 | 6/2018 |
| WO | WO2018/132181 A1 | 7/2018 |
| WO | WO2018/132182 A1 | 7/2018 |
| WO | WO2018/135477 A1 | 7/2018 |
| WO | WO2018/135478 A1 | 7/2018 |
| WO | WO2018/136592 A2 | 7/2018 |
| WO | WO2018/139508 A1 | 8/2018 |
| WO | WO2018/145434 A1 | 8/2018 |
| WO | WO2018/146045 A1 | 8/2018 |
| WO | WO2018/146170 A1 | 8/2018 |
| WO | WO2018/146173 A1 | 8/2018 |
| WO | WO2018/146177 A1 | 8/2018 |
| WO | WO2018/148456 A1 | 8/2018 |
| WO | WO2018/156524 A1 | 8/2018 |
| WO | WO2018/158636 A1 | 9/2018 |
| WO | WO2018/177344 A1 | 10/2018 |
| WO | WO2018/178939 A1 | 10/2018 |
| WO | WO2018/183128 A1 | 10/2018 |
| WO | WO2018/187576 A2 | 10/2018 |
| WO | WO2018/226991 A1 | 12/2018 |
| WO | WO2019/094963 A1 | 5/2019 |

OTHER PUBLICATIONS

Hildebrand et al.; U.S. Appl. No. 16/595,280 entitled "Intravascular blood pumps and methods of use," filed Oct. 7, 2019.

Jagani et al.; Dual-propeller cavopulmonary pump for assisting patients with hypoplastic right ventricle; ASAIO Journal (American Society for Artificial Internal Organs); 10 pages; DOI: 10.1097/MAT.0000000000000907; Jan. 2019.

(56) References Cited

OTHER PUBLICATIONS

Reitan et al.; First human use of the reitan catheter pump; Asaio Journal; 47 (2); p. 124; Mar.-Apr. 2001.

Salahieh et al., U.S. Appl. No. 16/189,876; entitled "Intravascular fluid movement devices, systems, and methods of use," filed Nov. 13, 2018.

Salahieh et al.; U.S. Appl. No. 16/523,949 entitled "Intravascular fluid movement devices, systems, and methods of use," filed Jul. 26, 2019.

INTRAVASCULAR BLOOD PUMPS AND METHODS OF USE AND MANUFACTURE

CROSS REFERENCE TO RELATED APPLICATIONS

This application claims priority to the following U.S. Provisional Patent Application, the disclosure of which is fully incorporated by reference herein for all purposes: App. No. 62/625,312, filed Feb. 1, 2018.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Patients with heart disease can have severely compromised ability to drive blood flow through the heart and vasculature, presenting for example substantial risks during corrective procedures such as balloon angioplasty and stent delivery. There is a need for ways to improve the volume or stability of cardiac outflow for these patients, especially during corrective procedures.

Intra-aortic balloon pumps (IABP) are commonly used to support circulatory function, such as treating heart failure patients. Use of IABPs is common for treatment of heart failure patients, such as supporting a patient during high-risk percutaneous coronary intervention (HRPCI), stabilizing patient blood flow after cardiogenic shock, treating a patient associated with acute myocardial infarction (AMI) or treating decompensated heart failure. Such circulatory support may be used alone or in with pharmacological treatment.

An IABP commonly works by being placed within the aorta and being inflated and deflated in counterpulsation fashion with the heart contractions, and one of the functions is to attempt to provide additive support to the circulatory system.

More recently, minimally-invasive rotary blood pumps have been developed that can be inserted into the body in connection with the cardiovascular system, such as pumping arterial blood from the left ventricle into the aorta to add to the native blood pumping ability of the left side of the patient's heart. Another known method is to pump venous blood from the right ventricle to the pulmonary artery to add to the native blood pumping ability of the right side of the patient's heart. An overall goal is to reduce the workload on the patient's heart muscle to stabilize the patient, such as during a medical procedure that may put additional stress on the heart, to stabilize the patient prior to heart transplant, or for continuing support of the patient.

The smallest rotary blood pumps currently available can be percutaneously inserted into the vasculature of a patient through an access sheath, thereby not requiring surgical intervention, or through a vascular access graft. A description of this type of device is a percutaneously-inserted ventricular support device.

There is a need to provide additional improvements to the field of ventricular support devices and similar blood pumps for treating compromised cardiac blood flow.

SUMMARY OF THE DISCLOSURE

This disclosure relates generally to intravascular fluid movement devices such as blood pump, and their methods of use and manufacture.

One aspect of the disclosure is an intravascular blood pump, comprising: a collapsible housing comprising a fluid lumen, the fluid lumen having a distal end, a proximal end, and a substantially constant diameter portion having a proximal end, wherein the fluid lumen proximal end is proximal to the proximal end of the substantially constant diameter portion; a collapsible distal impeller axially spaced from a collapsible proximal impeller, the distal impeller having an expanded configuration and the proximal impeller having an expanded configuration, wherein the proximal impeller has an axial length in the expanded configuration, and at least a portion of the proximal impeller is disposed in the substantially constant diameter portion and at least a portion of the of the proximal impeller, measured along the axial length, is disposed proximal to the proximal end of the substantially constant diameter portion.

In some embodiments, at least 20% and up to 90% of the proximal impeller (axial length) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, optionally up to 35% of the impeller, optionally up to 30% of the impeller, optionally up to 25% of the impeller, is disposed proximal to a proximal end of the constant diameter portion.

In some embodiments, at least 25% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 30% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 35% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 40% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller is disposed proximal to a proximal end of the constant diameter portion.

In some embodiments, at least 45% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller is disposed proximal to a proximal end of the constant diameter portion.

In some embodiments, at least 50% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller is disposed proximal to a proximal end of the constant diameter portion.

In some embodiments, at least 55% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller is disposed proximal to a proximal end of the constant diameter portion.

In some embodiments, at least 60% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller is disposed proximal to a proximal end of the constant diameter portion.

In some embodiments, at least 65% and up to 90% of the proximal impeller (measured axially) is disposed proximal to a proximal end of the constant diameter portion, optionally up to 85% of the impeller, optionally up to 80% of the impeller, optionally up to 75% of the impeller, optionally up to 70% of the impeller is disposed proximal to a proximal end of the constant diameter portion.

In some embodiments, at least 70% and up to 90% of the proximal impeller (measured axially) is disposed proximal to a proximal end of the constant diameter portion, optionally up to 85% of the impeller, optionally up to 80% of the impeller, optionally up to 75% of the impeller, is disposed proximal to a proximal end of the constant diameter portion.

In some embodiments, at least 75% and up to 90% of the proximal impeller (measured axially) is disposed proximal to a proximal end of the constant diameter portion, optionally up to 85% of the impeller, optionally up to 80% of the impeller is disposed proximal to a proximal end of the constant diameter portion.

In some embodiments, at least 80% and up to 90% of the proximal impeller (measured axially) is disposed proximal to a proximal end of the constant diameter portion, optionally up to 85% of the impeller is disposed proximal to a proximal end of the constant diameter portion.

A portion of the proximal impeller can extend further proximally that the fluid lumen proximal end when the proximal impeller is in the expanded configuration.

The fluid lumen can further comprise a proximal portion disposed proximal to the substantially constant diameter portion, the proximal portion including at least one surface adapted and configured to behave as a fluid diffuser. The proximal portion can comprise a flared configuration. The proximal portion can have a continuous and gradual flare from the proximal end of the substantially constant diameter portion to the fluid lumen proximal end. The proximal portion can have any other proximal portion configuration disclosed herein.

The collapsible housing can comprise a collapsible support structure coupled to a collapsible membrane.

One aspect of the disclosure is an intravascular blood pump, comprising: a collapsible housing comprising a fluid lumen, the fluid lumen having a distal end and a flared proximal region that has a distal end that is proximal to the fluid lumen distal end, the flared proximal region comprising at least one surface adapted and configured to behave as a fluid diffuser, a collapsible distal impeller axially spaced from a collapsible proximal impeller, the distal impeller having an expanded configuration and the proximal impeller having an expanded configuration, at least a portion of the proximal impeller disposed distal to the distal end of the flared proximal region, wherein the proximal impeller has an axial length in the expanded configuration, and at least a portion of the proximal impeller, measured along the axial length, is disposed proximal to the distal end of the flared proximal region.

In some embodiments, at least 20% and up to 90% of the proximal impeller (axial length) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, optionally up to 35% of the impeller, optionally up to 30% of the impeller, optionally up to 25% of the impeller, is disposed proximal to the distal end of the flared proximal region.

In some embodiments, at least 25% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to the distal end of the flared proximal region.

In some embodiments, at least 30% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to the distal end of the flared proximal region.

In some embodiments, at least 35% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to the distal end of the flared proximal region.

In some embodiments, at least 40% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller is disposed proximal to the distal end of the flared proximal region.

In some embodiments, at least 45% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller is disposed proximal to the distal end of the flared proximal region.

In some embodiments, at least 50% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller is disposed proximal to the distal end of the flared proximal region.

In some embodiments, at least 55% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller, optionally up to 60% of the impeller is disposed proximal to the distal end of the flared proximal region.

In some embodiments, at least 60% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller, optionally up to 65% of the impeller is disposed proximal to the distal end of the flared proximal region.

In some embodiments, at least 65% and up to 90% of the proximal impeller (measured axially) is disposed proximal to the distal end of the flared proximal region, optionally up to 85% of the impeller, optionally up to 80% of the impeller, optionally up to 75% of the impeller, optionally up to 70% of the impeller is disposed proximal to the distal end of the flared proximal region.

In some embodiments, at least 70% and up to 90% of the proximal impeller (measured axially) is disposed proximal to the distal end of the flared proximal region, optionally up to 85% of the impeller, optionally up to 80% of the impeller, optionally up to 75% of the impeller, is disposed proximal to the distal end of the flared proximal region.

In some embodiments, at least 75% and up to 90% of the proximal impeller (measured axially) is disposed proximal to the distal end of the flared proximal region, optionally up to 85% of the impeller, optionally up to 80% of the impeller is disposed proximal to the distal end of the flared proximal region.

In some embodiments, at least 80% and up to 90% of the proximal impeller (measured axially) is disposed proximal to the distal end of the flared proximal region, optionally up to 85% of the impeller is disposed proximal to the distal end of the flared proximal region.

A portion of the proximal impeller can extend further proximally that the fluid lumen proximal end when the proximal impeller is in the expanded configuration.

The fluid lumen can further comprise a substantially constant diameter portion distal to the flared proximal region.

The flared proximal region can have a continuous and gradual flare from the distal end of the flared region to the fluid lumen proximal end.

One aspect of the disclosure is an intravascular blood pump, comprising: a collapsible housing comprising a fluid lumen, the fluid lumen having a distal end, a proximal end, and a substantially constant diameter portion having a proximal end; a collapsible distal impeller axially spaced from a collapsible proximal impeller, the distal impeller having an expanded configuration and the proximal impeller having an expanded configuration, at least a portion of the proximal impeller is disposed in the substantially constant diameter portion, wherein the proximal impeller has an axial length in the expanded configuration, and a midpoint halfway along the axial length, wherein the midpoint is proximal to the proximal end of the substantially constant diameter portion.

One aspect of the disclosure is an intravascular blood pump, comprising: a collapsible housing comprising a fluid lumen, the fluid lumen having a distal end and a proximal end; a collapsible distal impeller axially spaced from a collapsible proximal impeller, the distal impeller having an expanded configuration and the proximal impeller having an expanded configuration, and at least a portion of each of the distal and proximal impellers disposed between the distal and proximal ends of the fluid lumen, wherein the proximal impeller and the distal impeller are each, when in their expanded configurations and when rotated, positioned relative to the fluid lumen such that the proximal impeller is performing more than 50% of the work of the blood pump and the distal impeller is performing less than 50% of the work of the blood pump.

The blood pump can include any other blood pump feature included herein, such as the relative axial positions of the proximal impeller relative to the fluid lumen.

The blood pump may not include a vane disposed axially between the proximal and distal impellers.

The blood pump may not include a stator blade disposed axially between the proximal and distal impellers.

At least half of the proximal impeller, measured along an axial length, can be disposed proximal to a proximal end of a substantially constant diameter portion of the fluid lumen.

At least half of the proximal impeller, measured along an axial length, can be disposed in a flared proximal region of the fluid lumen.

A proximal impeller and a distal impeller can each, when in their expanded configurations, be positioned relative to the fluid lumen such that the proximal impeller is performing more than 55% of the work of the blood pump and the distal impeller is performing less than 45% of the work of the blood pump.

A proximal impeller and a distal impeller can each, when in their expanded configurations, be positioned relative to the fluid lumen such that the proximal impeller is performing more than 60% of the work of the blood pump and the distal impeller is performing less than 40% of the work of the blood pump.

A proximal impeller and a distal impeller can each, when in their expanded configurations, be positioned relative to the fluid lumen such that the proximal impeller is performing more than 70% of the work of the blood pump and the distal impeller is performing less than 30% of the work of the blood pump.

A proximal impeller and a distal impeller can each, when in their expanded configurations, be positioned relative to the fluid lumen such that the proximal impeller is performing more than 80% of the work of the blood pump and the distal impeller is performing less than 20% of the work of the blood pump.

One aspect of the disclosure is method of intravascularly pumping blood in a subject, comprising: positioning a pump housing fluid lumen first end in a first anatomical location (e.g., a left ventricle); positioning a distal impeller of the blood pump in the first anatomical location; positioning a proximal impeller of the blood pump in a second anatomical location (e.g., an ascending aorta); positioning a pump housing fluid lumen second end in the second anatomical location; positioning at least a portion of a central region of the fluid lumen across tissue (e.g., an aortic valve), creating a flow path between the fluid lumen first end positioned in the first anatomical region and the fluid lumen second end positioned in the second anatomical location such that the distal impeller and the proximal impeller can pump blood through the fluid lumen.

The method can include rotating the distal impeller and proximal impeller and thereby causing the proximal impeller to perform more than 50% of the work of the blood pump and the distal impeller to perform less than 50% of the work of the blood pump.

The rotating step can comprise rotating the distal impeller and proximal impeller and thereby causing the proximal impeller to perform more than 60% of the work of the blood pump and the distal impeller to perform less than 40% of the work of the blood pump.

The rotating step can comprise rotating the distal impeller and proximal impeller and thereby causing the proximal impeller to perform more than 70% of the work of the blood pump and the distal impeller to perform less than 30% of the work of the blood pump.

The rotating step can comprise rotating the distal impeller and proximal impeller and thereby causing the proximal impeller to perform more than 75% of the work of the blood pump and the distal impeller to perform less than 25% of the work of the blood pump.

The rotating step can comprise rotating the distal impeller and proximal impeller and thereby causing the proximal impeller to perform about 80% of the work of the blood pump and the distal impeller to perform about 20% of the work of the blood pump.

One aspect of the disclosure is an intravascular blood pump, comprising: a collapsible housing comprising a fluid lumen, the fluid lumen having a distal end and a proximal end; a collapsible distal impeller axially spaced from a collapsible proximal impeller, the distal impeller having an expanded configuration and the proximal impeller having an expanded configuration, and at least a portion of each of the distal and proximal impellers disposed between the distal and proximal ends of the fluid lumen, wherein the proximal impeller and the distal impeller are each, when in their expanded configurations and when rotated, positioned relative to the fluid lumen such that the proximal impeller is generating more than 50% of the pressure generated by the blood pump and the distal impeller is generating less than 50% of the pressure generated by the blood pump of the blood pump.

The blood pump may not include a vane disposed axially between the proximal and distal impellers.

The blood pump may not include a stator blade disposed axially between the proximal and distal impellers.

The proximal impeller and the distal impeller can each be, when in their expanded configurations, positioned relative to the fluid lumen such that the proximal impeller is generating more than 55% of the pressure generated by the blood pump and the distal impeller is generating less than 45% of the pressure generated by the blood pump.

The proximal impeller and the distal impeller can are each be, when in their expanded configurations, positioned relative to the fluid lumen such that the proximal impeller is generating more than 60% of the pressure generated by the blood pump and the distal impeller is generating less than 40% of the pressure generated by the blood pump.

The proximal impeller and the distal impeller can each be, when in their expanded configurations, positioned relative to the fluid lumen such that the proximal impeller is generating more than 70% of the pressure generated by the blood pump and the distal impeller is generating less than 30% of the pressure generated by the blood pump.

The proximal impeller and the distal impeller can each be, when in their expanded configurations, positioned relative to the fluid lumen such that the proximal impeller is generating about 80% of the pressure generated by the blood pump and the distal impeller is generating about 20% of the pressure generated by the blood pump.

One aspect of the disclosure is an intravascular blood pump, comprising: a collapsible housing comprising a fluid lumen, the fluid lumen having a distal end, a proximal end, and a substantially constant diameter portion having a proximal end, wherein the fluid lumen proximal end is proximal to the proximal end of the substantially constant diameter portion; a collapsible distal impeller axially spaced from a collapsible proximal impeller, the distal impeller having an expanded configuration and the proximal impeller having an expanded configuration, at least a portion of the proximal impeller is disposed in the substantially constant diameter portion, wherein the proximal impeller has an axial length in the expanded configuration.

Any other features of a blood pump herein can be incorporated into this aspect.

One aspect of the disclosure is an intravascular blood pump, comprising: a collapsible housing comprising a fluid lumen, the fluid lumen having a distal end, a proximal end, and a proximal region with a lumen wall configuration, the proximal region including the proximal end; a collapsible distal impeller axially spaced from a collapsible proximal impeller, the distal impeller having an expanded configuration and the proximal impeller having an expanded, at least a portion of the proximal impeller disposed distal to the proximal region of the fluid lumen; wherein the proximal impeller has at least one blade with a surface, the at least one blade surface and the lumen wall configured such that if the proximal impeller is moved at least 2 mm proximally relative to an initial position such that less of the proximal impeller is disposed distal to the proximal region of fluid lumen, the change in axial position of the proximal impeller results in at least a 10% in flow.

This disclosure includes methods of manufacturing any and all of the blood pumps herein.

This disclosure includes methods of using any and all of the blood pumps herein, examples of which are provided herein in some exemplary anatomical locations.

Any of the axial spacing between proximal and distal impellers described herein can be applied to any of the embodiments herein, including any embodiments in the Claims, Description, or Summary sections.

DETAILED DESCRIPTION

The present disclosure is related to medical devices, systems, and methods of use and manufacture. Medical devices herein may include a distal working portion adapted to be disposed within a physiologic vessel, wherein the distal working portion includes one or more components that act upon fluid. For example, distal working portions herein may include one or more rotating members that when rotated, can facilitate the movement of a fluid such as blood.

Any of the disclosure herein relating to an aspect of a system, device, or method of use can be incorporated with any other suitable disclosure herein. For example, a figure describing only one aspect of a device or method can be included with other embodiments even if that is not specifically stated in a description of one or both parts of the disclosure. It is thus understood that combinations of different portions of this disclosure are included herein unless specifically indicated otherwise.

Figure 1:
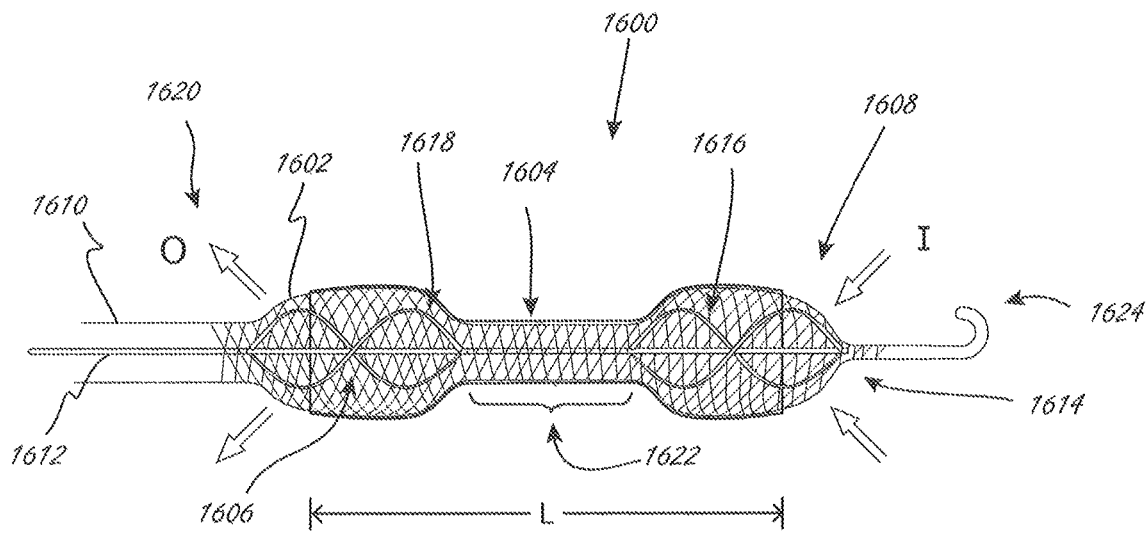
FIG. 1 is a side view of an exemplary working portion that includes a conduit, a plurality of impellers, an expandable member.

FIG. 1 is a side view illustrating a distal portion of an exemplary intravascular fluid pump, including pump portion 1600, wherein pump portion 1600 includes proximal impeller 1606 and distal impeller 1616, both of which are in operable communication with drive cable 1612. Pump portion 1600 is in an expanded configuration in FIG. 1, but is adapted to be collapsed to a delivery configuration so that it can be delivered with a lower profile. The impellers can be attached to drive cable 1612. Drive cable 1612 is in operable communication with an external motor, not shown, and extends through elongate shaft 1610. The phrases "pump portion" and "working portion" (or derivatives thereof) may be used herein interchangeably unless indicated to the contrary. For example without limitation, "pump portion" 1600 can also be referred to herein as a "working portion."

Pump portion 1600 also includes expandable member 1602, which in this embodiment has a proximal end 1620 that extends further proximally than a proximal end of proximal impeller 1606, and a distal end 1608 that extends further distally than a distal end 1614 of distal impeller 1616. Expandable member 1602 is disposed radially outside of the impellers along the axial length of the impellers. Expandable member 1602 can be constructed in a manner and made from materials similar to many types of expandable structures that are known in the medical arts to be able to collapsed and expanded, examples of which are provided herein. Examples of suitable materials include, but are not limited to, polyurethane and polyurethane elastomers.

Pump portion 1600 also includes conduit 1604, which is coupled to expandable member 1602, has a length L, and extends axially between the impellers. Conduit 1604 creates and provides a fluid lumen between the two impellers. When in use, fluid move through the lumen provided by conduit 1604. The conduits herein are non-permeable, or they can be semi-permeable, or even porous as long as they can still define a lumen. The conduits herein are also flexible, unless it is otherwise indicated. The conduits herein extend completely around (i.e., 360 degrees) at least a portion of the pump portion. In pump portion 1600, conduit extends completely around expandable member 1602, but does not extend all the way to the proximal end 1602 or distal end 1608 of expandable member 1602. The structure of the expandable member creates at least one inlet aperture to allow for inflow "I," and at least one outflow aperture to allow for outflow "O." Conduit 1604 improves impeller pumping dynamics, compared to those that working portion 1600 would have without the conduit.

Expandable member 1602 can have a variety of constructions, and made from a variety of materials. For example, expandable member 1602 may be formed similar to expandable stents or stent-like devices, or any other example provided herein. For example without limitation, expandable member 1602 could have an open-braided construction, such as a 24-end braid, although more or fewer braid wires could be used. Exemplary materials for the expandable member include nitinol, cobalt alloys, and polymers, although other materials could be used. Expandable member 1602 has an expanded configuration, as shown, in which the outer dimension (measured orthogonally relative a longitudinal axis of the working portion) of the expandable member is greater in at least a region where it is disposed radially outside of the impellers than in a central region 1622 of the expandable member that extends axially between the impeller. Drive cable 1612 is co-axial with the longitudinal axis in this embodiment. In use, the central region can be placed across a valve, such as an aortic valve. In some embodiments, expandable member 1602 is adapted and constructed to expand to an outermost dimension of 12-24 F (4.0-8.0 mm) where the impellers are axially within the expandable member, and to an outermost dimension of 10-20 F (3.3-6.7 mm) in central region 1622 between the impellers. The smaller central region outer dimension can reduce forces acting on the valve, which can reduce or minimize damage to the valve. The larger dimensions of the expandable member in the regions of the impellers can help stabilize the working portion axially when in use. Expandable member 1602 has a general dumbbell configuration. Expandable member 1602 has an outer configuration that tapers as it transitions from the impeller regions to central region 1622, and again tapers at the distal and proximal ends of expandable member 1602.

Expandable member 1602 has a proximal end 1620 that is coupled to shaft 1610, and a distal end 1608 that is coupled to distal tip 1624. The impellers and drive cable 1612 rotate within the expandable member and conduit assembly. Drive cable 1612 is axially stabilized with respect to distal tip 1624, but is free to rotate with respect to tip 1624.

In some embodiments, expandable member 1602 can be collapsed by pulling tension from end-to-end on the expandable member. This may include linear motion (such as, for example without limitation, 5-20 mm of travel) to axially extend expandable member 1602 to a collapsed configuration with collapsed outer dimension(s). Expandable member 1602 can also be collapsed by pushing an outer shaft such as a sheath over the expandable member/conduit assembly, causing the expandable member and conduit to collapse towards their collapsed delivery configuration.

Impellers 1606 and 1616 are also adapted and constructed such that one or more blades will stretch or radially compress to a reduced outermost dimension (measured orthogonally to the longitudinal axis of the working portion). For example without limitation, any of the impellers herein can include one or more blades made from a plastic formulation with spring characteristics, such as any of the impellers described in U.S. Pat. No. 7,393,181, the disclosure of which is incorporated by reference herein for all purposes and can be incorporated into embodiments herein unless this disclosure indicates to the contrary. Alternatively, for example, one or more collapsible impellers can comprise a superelastic wire frame, with polymer or other material that acts as a webbing across the wire frame, such as those described in U.S. Pat. No. 6,533,716, the disclosure of which is incorporated by reference herein for all purposes.

The inflow and/or outflow configurations of working portion 1600 can be mostly axial in nature.

Exemplary sheathing and unsheathing techniques and concepts to collapse and expand medical devices are known, such as, for example, those described and shown in U.S. Pat. No. 7,841,976 or 8,052,749, the disclosures of which are incorporated by reference herein.

Figure 2:
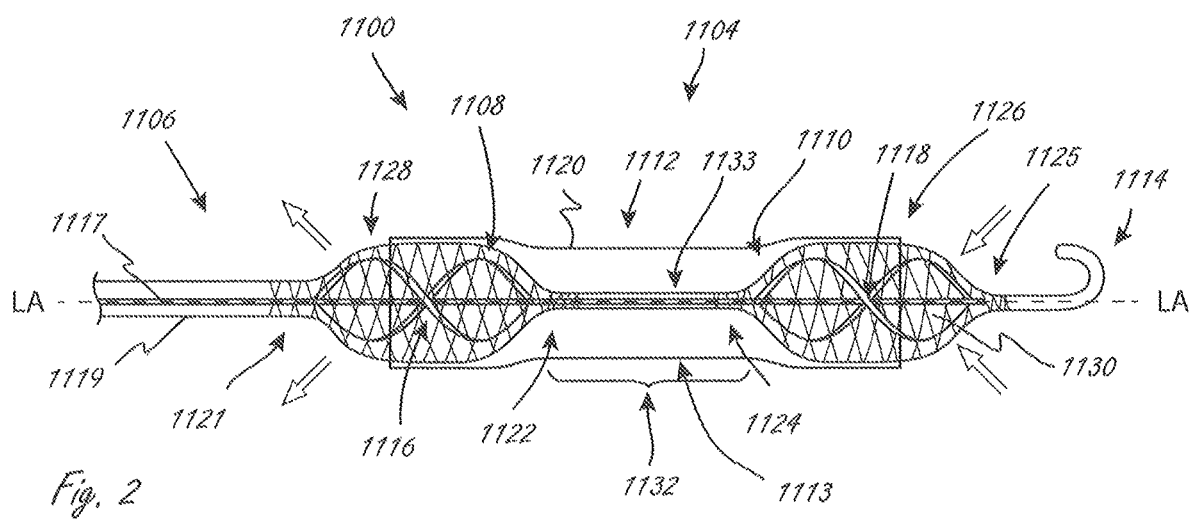
FIG. 2 is a side view of an exemplary working portion that includes a conduit, a plurality of impellers, and a plurality of expandable members.

FIG. 2 is a side view illustrating a deployed configuration (shown extracorporally) of a distal portion of an exemplary embodiment of a fluid movement system. Exemplary system 1100 includes working portion 1104 (which as set forth herein may also be referred to herein as a pump portion) and an elongate portion 1106 extending from working portion 1104. Elongate portion 1106 can extend to a more proximal region of the system, not shown for clarity, and that can include, for example, a motor. Working portion 1104 includes first expandable member 1108 and second expandable member 1110, axially spaced apart along a longitudinal axis LA of working portion 1104. Spaced axially in this context refers to the entire first expandable member being axially spaced from the entire second expandable member along a longitudinal axis LA of working portion 1104. A first end 1122 of first expandable member 1108 is axially spaced from a first end 1124 of second expandable member 1110.

First and second expandable members 1108 and 1110 generally each include a plurality of elongate segments disposed relative to one another to define a plurality of apertures 1130, only one of which is labeled in the second expandable member 1110. The expandable members can have a wide variety of configurations and can be constructed in a wide variety of ways, such as any of the configurations or constructions in, for example without limitation, U.S. Pat. No. 7,841,976, or the tube in U.S. Pat. No. 6,533,716, which is described as a self-expanding metal endoprosthetic material. For example, without limitation, one or both of the expandable members can have a braided construction or can be at least partially formed by laser cutting a tubular element.

Working portion 1104 also includes conduit 1112 that is coupled to first expandable member 1108 and to second expandable member 1110, and extends axially in between first expandable member 1108 and second expandable member 1110 in the deployed configuration. A central region 1113 of conduit 1112 spans an axial distance 1132 where the working portion is void of first and second expandable members 1108 and 1110. Central region 1113 can be considered to be axially in between the expandable members. Distal end 1126 of conduit 1112 does not extend as far distally as a distal end 1125 of second expandable member 1110, and proximal end of conduit 1128 does not extend as far proximally as proximal end 1121 of first expandable member 1108.

When the disclosure herein refers to a conduit being coupled to an expandable member, the term coupled in this context does not require that the conduit be directly attached to the expandable member so that conduit physically contacts the expandable member. Even if not directly attached, however, the term coupled in this context refers to the conduit and the expandable member being joined together such that as the expandable member expands or collapses, the conduit also begins to transition to a different configuration and/or size. Coupled in this context therefore refers to conduits that will move when the expandable member to which it is coupled transitions between expanded and collapsed configurations.

Any of the conduits herein can be deformable to some extent. For example, conduit 1112 includes elongate member 1120 that can be made of one or more materials that allow the central region 1113 of conduit to deform to some extent radially inward (towards LA) in response to, for example and when in use, forces from valve tissue (e.g., leaflets) or a replacement valve as working portion 1104 is deployed towards the configuration shown in FIG. 2. The conduit may be stretched tightly between the expandable members in some embodiments. The conduit may alternatively be designed with a looseness that causes a greater degree of compliance. This can be desirable when the working portion is disposed across fragile structures such as an aortic valve, which may allow the valve to compress the conduit in a way that minimizes point stresses in the valve. In some embodiments, the conduit may include a membrane attached to the proximal and distal expandable members. Exemplary materials that can be used for any conduits herein include, without limitations, polyurethane rubber, silicone rubber, acrylic rubber, expanded polytetrafluoroethylene, polyethylene, polyethylene terephthalate, including any combination thereof.

Any of the conduits herein can have a thickness of, for example, 0.5-20 thousandths of an inch (thou), such as 1-15 thou, or 1.5 to 15 thou, 1.5 to 10 thou, or 2 to 10 thou.

Any of the conduits herein, or at least a portion of the conduit, can be impermeable to blood. In FIG. 2, working portion 1104 includes a lumen that extends from distal end 1126 of conduit 1112 and extends to proximal end 1128 of conduit 1112. The lumen is defined by conduit 1112 in central region 1113, but can be thought of being defined by both the conduit and portions of the expandable members in regions axially adjacent to central region 1113. In this embodiment, however, it is the conduit material that causes the lumen to exist and prevents blood from passing through the conduit.

Any of the conduits herein that are secured to one or more expandable members can be, unless indicated to the contrary, secured so that the conduit is disposed radially outside of one or more expandable members, radially inside of one or more expandable members, or both, and the expandable member can be impregnated with the conduit material.

The proximal and distal expandable members help maintain the conduit in an open configuration to create the lumen, while each also creates a working environment for an impeller, described below. Each of the expandable members, when in the deployed configuration, is maintained in a spaced relationship relative to a respective impeller, which allows the impeller to rotate within the expandable member without contacting the expandable member. Working portion 1104 includes first impeller 1116 and second impeller 1118, with first impeller 1116 disposed radially within first expandable member 1108 and second impeller 1118 disposed radially within second expandable member 1110. In this embodiment, the two impellers even though they are distinct and separate impellers, are in operable communication with a common drive mechanism (e.g., drive cable 1117), such that when the drive mechanism is activated the two impellers rotate together. In this deployed configuration, impellers 1116 and 1118 are axially spaced apart along longitudinal axis LA, just as are the expandable members 1108 and 1110 are axially spaced apart.

Impellers 1116 and 1118 are also axially within the ends of expandable members 1108 and 1110, respectively (in addition to being radially within expandable members 1108 and 1110). The impellers herein can be considered to be axially within an expandable member even if the expandable member includes struts extending from a central region of the expandable member towards a longitudinal axis of the working portion (e.g., tapering struts in a side view). In FIG. 2, second expandable member 1110 extends from first end 1124 (proximal end) to second end 1125 (distal end).

In FIG. 2, a distal portion of impeller 1118 extends distally beyond distal end 1126 of conduit 1112, and a proximal portion of impeller 1116 extends proximally beyond proximal end 1128 of conduit 1112. In this figure, portions of each impeller are axially within the conduit in this deployed configuration.

In the exemplary embodiment shown in FIG. 2, impellers 1116 and 1118 are in operable communication with a common drive mechanism 1117, and in this embodiment, the impellers are each coupled to drive mechanism 1117, which extends through shaft 1119 and working portion 1104. Drive mechanism 1117 can be, for example, an elongate drive cable, which when rotated causes the impellers to rotate. In this example, as shown, drive mechanism 1117 extends to and is axially fixed relative to distal tip 1114, although it is adapted to rotate relative to distal tip 1114 when actuated. Thus, in this embodiment, the impellers and drive mechanism 1117 rotate together when the drive mechanism is rotated. Any number of known mechanisms can be used to rotate drive mechanism, such as with a motor (e.g., an external motor).

The expandable members and the conduit are not in rotational operable communication with the impellers and the drive mechanism. In this embodiment, proximal end 1121 of proximal expandable member 1108 is coupled to shaft 1119, which may be a shaft of elongate portion 1106 (e.g., an outer catheter shaft). Distal end 1122 of proximal expandable member 1108 is coupled to central tubular member 1133, through which drive mechanism 1117 extends. Central tubular member 1133 extends distally from proximal expandable member 1108 within conduit 1112 and is also coupled to proximal end 1124 of distal expandable member 1110. Drive mechanism 1117 thus rotates within and relative to central tubular member 1133. Central tubular member 1133 extends axially from proximal expandable member 1108 to distal expandable member 1110. Distal end 1125 of distal expandable member 1110 is coupled to distal tip 1114, as shown. Drive mechanism 1117 is adapted to rotate relative to tip 1114, but is axially fixed relative to tip 1114.

Working portion 1104 is adapted and configured to be collapsed to a smaller profile than its deployed configuration (which is shown in FIG. 2). This allows it to be delivered using a lower profile delivery device (smaller French size) than would be required if none of working portion 1104 was collapsible. Even if not specifically stated herein, any of the expandable members and impellers may be adapted and configured to be collapsible to some extent to a smaller delivery configuration.

The working portions herein can be collapsed to a collapsed delivery configuration using conventional techniques, such as with an outer sheath that is movable relative to the working portion (e.g., by axially moving one or both of the sheath and working portion). For example without limitation, any of the systems, devices, or methods shown in the following references may be used to facilitate the collapse of a working portions herein: U.S. Pat. No. 7,841, 976 or 8,052,749, the disclosures of which are incorporated by reference herein for all purposes.

Figure 3A:
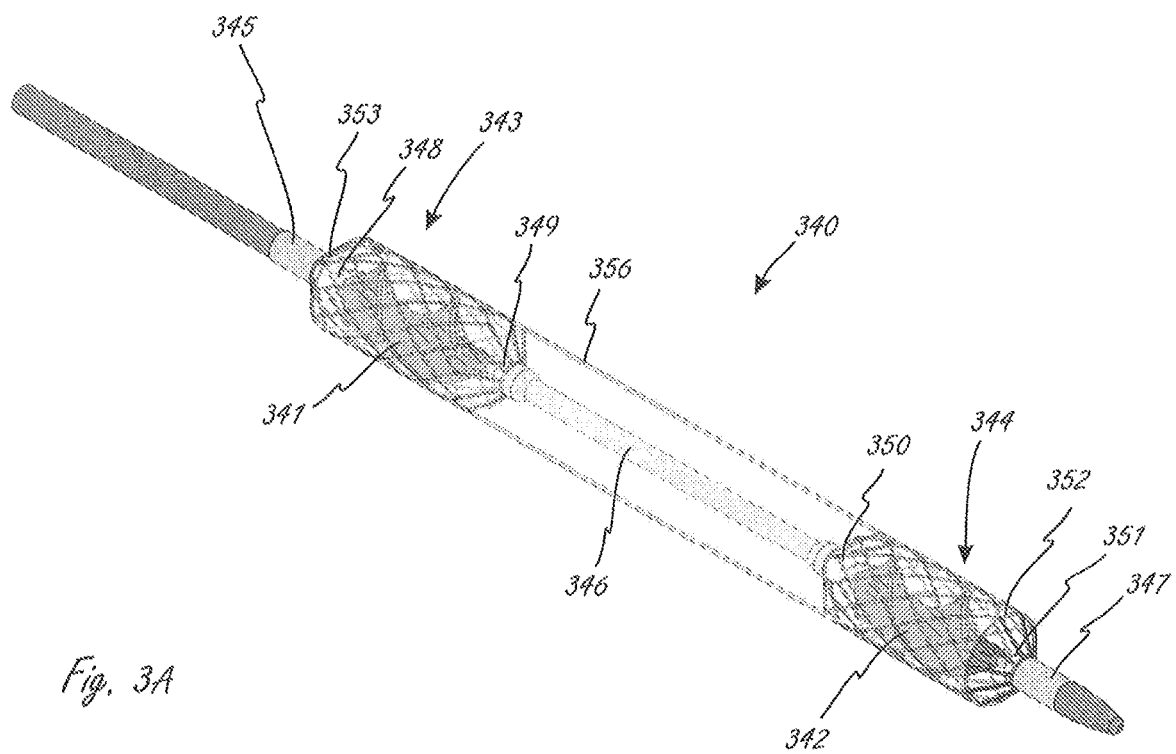
FIGS. 3A, 3B, 3C and 3D illustrate an exemplary working portion that includes a conduit, a plurality of impellers, and a plurality of expandable members.
Figure 3B:
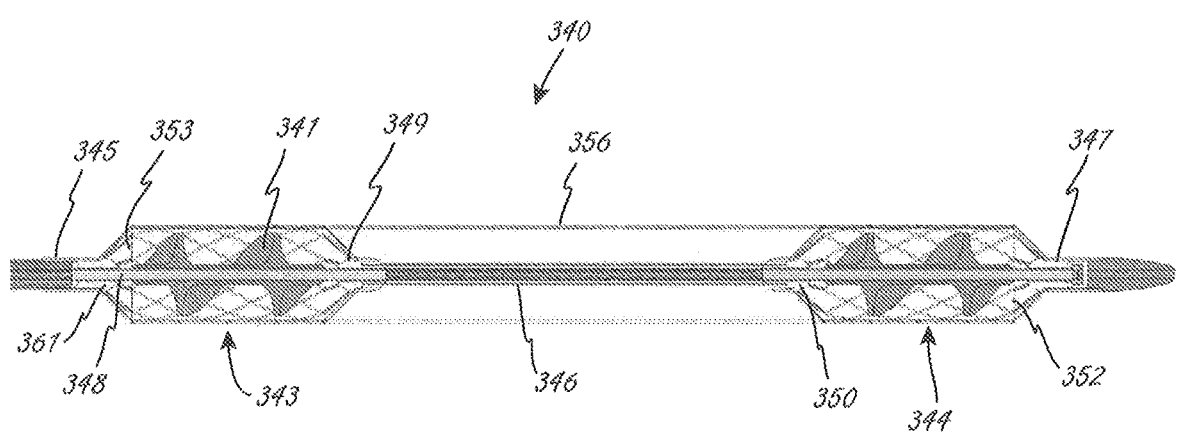
Figure 3C:
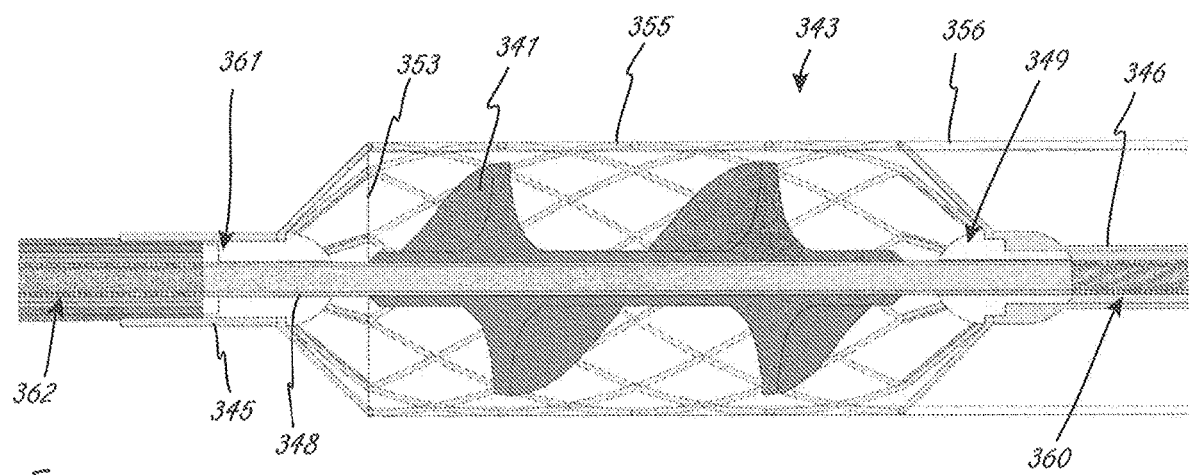
Figure 3D:
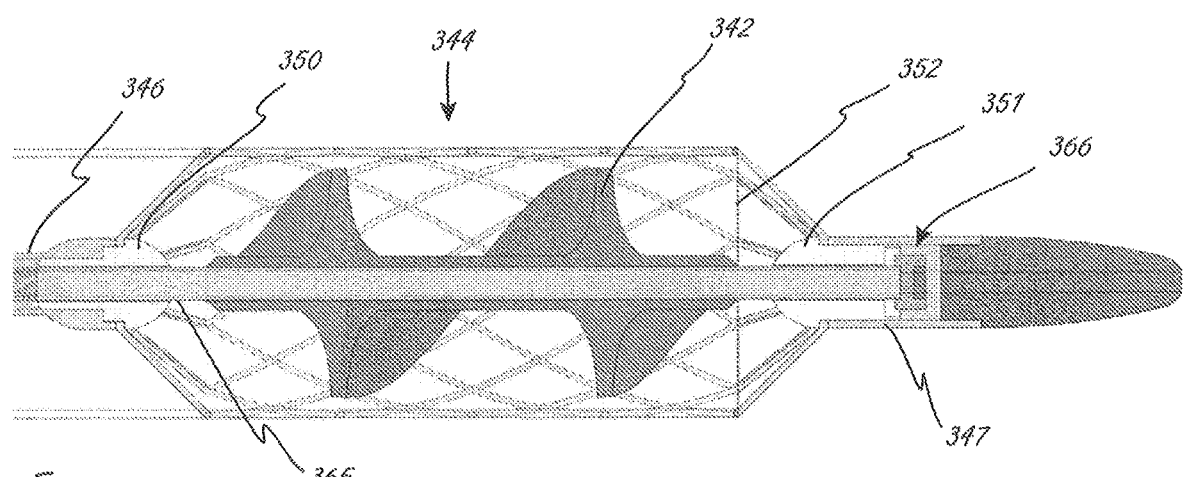

FIGS. 3A-3E show an exemplary working portion that is similar in some ways to the working portion shown in FIG. 2. Working portion 340 is similar to working portion 1104 in that in includes two expandable members axially spaced from one another when the working portion is expanded, and a conduit extending between the two expandable members. FIG. 3A is a perspective view, FIG. 3B is a side sectional view, and FIGS. 3C and 3D are close-up side sectional views of sections of the view in FIG. 3B.

Working portion 340 includes proximal impeller 341 and distal impeller 342, which are coupled to and in operational communication with a drive cable, which defines therein a lumen. The lumen can be sized to accommodate a guidewire, which can be used for delivery of the working portion to the desired location. The drive cable, in this embodiment, includes first section 362 (e.g., wound material), second section 348 (e.g., tubular member) to which proximal impeller 341 is coupled, third section 360 (e.g., wound material), and fourth section 365 (e.g., tubular material) to which distal impeller 342 is coupled. The drive cable sections all have the same inner diameter, so that lumen has a constant inner diameter. The drive cable sections can be secured to each other using known attachment techniques. A distal end of fourth section 365 extends to a distal region of the working portion, allowing the working portion to be, for example, advanced over a guidewire for positioning the working portion. In this embodiment the second and fourth sections can be stiffer than first and third sections. For example, second and fourth can be tubular and first and third sections can be wound material to impart less stiffness.

Working portion 340 includes proximal expandable member 343 and distal expandable member 344, each of which extends radially outside of one of the impellers. The expandable members have distal and proximal ends that also extend axially beyond distal and proximal ends of the impellers, which can be seen in FIGS. 3B-3D. Coupled to the two expandable members is conduit 356, which has a proximal end 353 and a distal end 352. The two expandable members each include a plurality of proximal struts and a plurality of distal struts. The proximal struts in proximal expandable member 343 extend to and are secured to shaft section 345, which is coupled to bearing 361, through which the drive cable extends and is configured and sized to rotate. The distal struts of proximal expandable member 343 extend to and are secured to a proximal region (to a proximal end in this case) of central tubular member 346, which is disposed axially in between the expandable members. The proximal end of central tubular member 346 is coupled to bearing 349, as shown in FIG. 3C, through which the drive cable extends and rotates. The proximal struts of distal expandable member 344 extend to and secured to a distal region (to a distal end in this case) of central tubular member 346. Bearing 350 is also coupled to the distal region of central tubular member 346, as is shown in FIG. 3D. The drive cable extends through and rotates relative to bearing 350. Distal struts of distal expandable member extend to and are secured to shaft section 347 (see FIG. 3A), which can be considered part of the distal tip. Shaft section 347 is coupled to bearing 351 (see FIG. 3D), through which the drive cable extends and rotates relative to. The distal tip also includes bearing 366 (see FIG. 3D), which can be a thrust bearing. Working portion 340 can be similar to or the same in some aspects to working portion 1104, even if not explicitly included in the description. In this embodiment, conduit 356 extends at least as far as ends of the impeller, unlike in working portion 1104. Either embodiment can be modified so that the conduit extends to a position as set forth in the other embodiment. In some embodiments, section 360 can be a tubular section instead of wound.

In alternative embodiments, at least a portion of any of the impellers herein may extend outside of the fluid lumen. For example, only a portion of an impeller may extend beyond an end of the fluid lumen in either the proximal or distal direction. In some embodiments, a portion of an impeller that extends outside of the fluid lumen is a proximal portion of the impeller, and includes a proximal end (e.g., see the proximal impeller in FIG. 2). In some embodiments, the portion of the impeller that extends outside of the fluid lumen is a distal portion of the impeller, and includes a distal end (e.g., see the distal impeller in FIG. 2). When the disclosure herein refers to impellers that extend outside of the fluid lumen (or beyond an end), it is meant to refer to relative axial positions of the components, which can be most easily seen in side views or top views, such as in FIG. 2.

A second impeller at another end of the fluid lumen may not, however, extend beyond the fluid lumen. For example, an illustrative alternative design can include a proximal impeller that extends proximally beyond a proximal end of the fluid lumen (like the proximal impeller in FIG. 2), and the fluid lumen does not extend distally beyond a distal end of a distal impeller (like in FIG. 3B). Alternatively, a distal end of a distal impeller can extend distally beyond a distal end of the fluid lumen, but a proximal end of a proximal impeller does not extend proximally beyond a proximal end of the fluid lumen. In any of the pump portions herein, none of the impellers may extend beyond ends of the fluid lumen.

While specific exemplary locations may be shown herein, the fluid pumps may be able to be used in a variety of locations within a body. Some exemplary locations for placement include placement in the vicinity of an aortic valve or pulmonary valve, such as spanning the valve and positioned on one or both sides of the valve, and in the case of an aortic valve, optionally including a portion positioned in the ascending aorta. In some other embodiments, for example, the pumps may be, in use, positioned further downstream, such as being disposed in a descending aorta.

Figure 4:
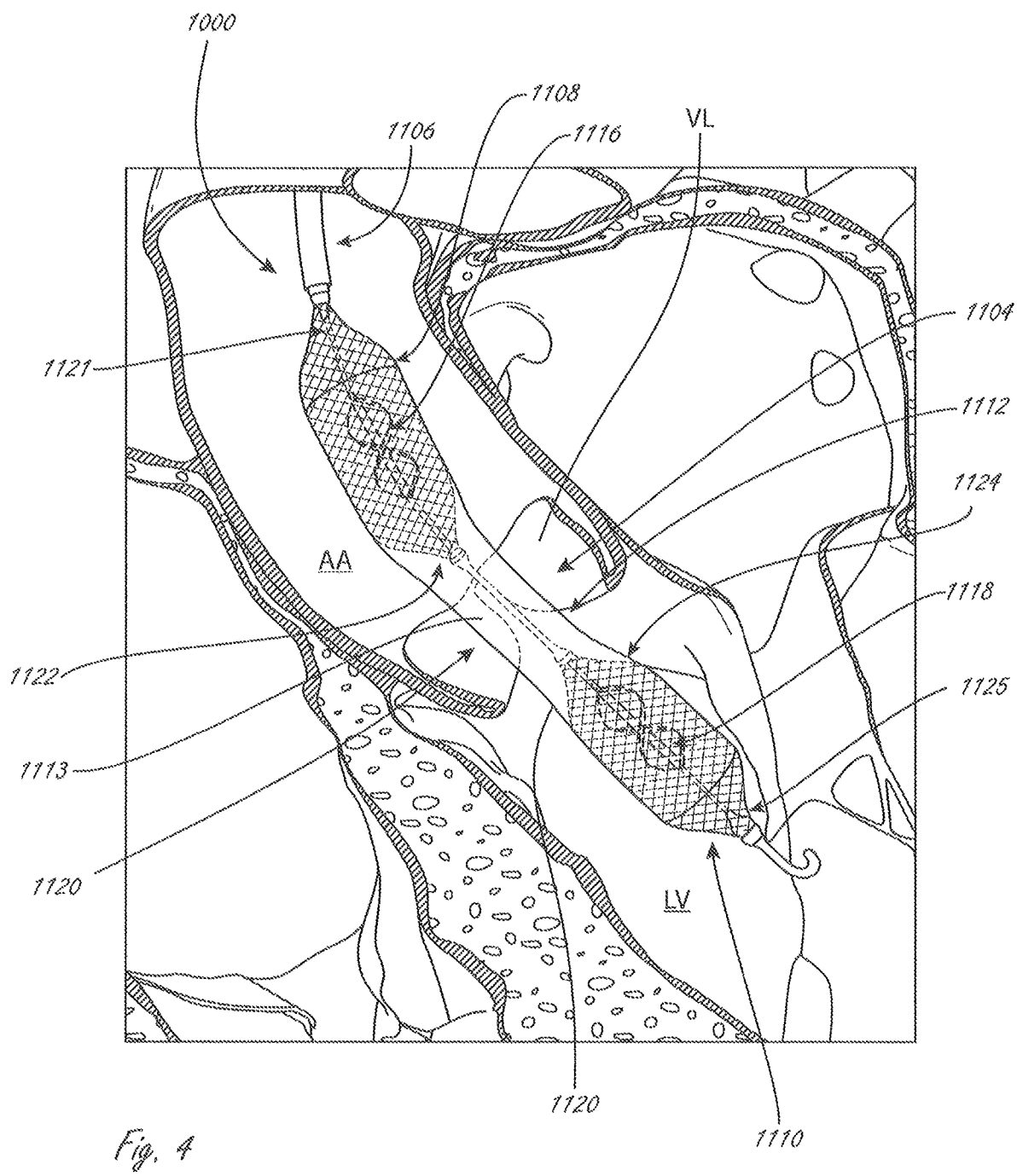
FIG. 4 illustrates an exemplary placement of a working portion, the working portion including a conduit, a plurality of expandable members, and a plurality of impellers.

FIG. 4 illustrates an exemplary placement of working portion 1104 from system 1000 from FIG. 2. One difference shown in FIG. 4 is that the conduit extends at least as far as the ends of the impellers, like in FIGS. 3A-3D. FIG. 4 shows working portion 1104 in a deployed configuration, positioned in place across an aortic valve. Working portion 1104 can be delivered as shown via, for example without limitation, femoral artery access (a known access procedure). While not shown for clarity, system 1000 can also include an outer sheath or shaft in which working portion 1104 is disposed during delivery to a location near an aortic valve. The sheath or shaft can be moved proximally (towards the ascending aorta "AA" and away from left ventricle "LV") to allow for deployment and expansion of working portion 1104. For example, the sheath can be withdrawn to allow for expansion of second expandable member 1110, with continued proximal movement allowing first expandable member 1108 to expand.

In this embodiment, second expandable member 1110 has been expanded and positioned in a deployed configuration such that distal end 1125 is in the left ventricle "LV," and distal to aortic valve leaflets "VL," as well as distal to the annulus. Proximal end 1124 has also been positioned distal to leaflets VL, but in some methods proximal end 1124 may extend slightly axially within the leaflets VL. This embodiment is an example of a method in which at least half of the second expandable member 1110 is within the left ventricle, as measured along its length (measured along the longitudinal axis). And as shown, this is also an example of a method in which the entire second expandable member 1110 is within the left ventricle. This is also an example of a method in which at least half of second impeller 1118 is positioned within the left ventricle, and also an embodiment in which the entire second impeller 1118 is positioned within the left ventricle.

Continued retraction of an outer shaft or sheath (and/or distal movement of working end 1104 relative to an outer sheath or shaft) continues to release conduit 1112, until central region 1113 is released and deployed. The expansion of expandable members 1108 and 1110 causes conduit 1112 to assume a more open configuration, as shown in FIG. 4. Thus, while in this embodiment conduit 1112 does not have the same self-expanding properties as the expandable members, the conduit will assume a deployed, more open configuration when the working end is deployed. At least a portion of central region 1113 of conduit 1112 is positioned at an aortic valve coaptation region. In FIG. 3, there is a short length of central region 1113 that extends distally beyond the leaflets VL, but at least some portion of central region 1113 is axially within the leaflets.

Continued retraction of an outer shaft or sheath (and/or distal movement of working end 1104 relative to an outer sheath or shaft) deploys first expandable member 1108. In this embodiment, first expandable member 1108 has been expanded and positioned (as shown) in a deployed configuration such that proximal end 1121 is in the ascending aorta AA, and proximal to leaflets "VL." Distal end 1122 has also been positioned proximal to leaflets VL, but in some methods distal end 1122 may extend slightly axially within the leaflets VL. This embodiment is an example of a method in which at least half of first expandable member 1110 is within the ascending aorta, as measured along its length (measured along the longitudinal axis). And as shown, this is also an example of a method in which the entire first expandable member 1110 is within the AA. This is also an example of a method in which at least half of first impeller 1116 is positioned within the AA, and also an embodiment in which the entire first impeller 1116 is positioned within the AA.

At any time during or after deployment of working portion 1104, the position of the working portion can be assessed in any way, such as under fluoroscopy. The position of the working portion can be adjusted at any time during or after deployment. For example, after second expandable member 1110 is released but before first expandable member 1108 is released, working portion 1104 can be moved axially (distally or proximally) to reposition the working portion. Additionally, for example, the working portion can be repositioned after the entire working portion has been released from a sheath to a desired final position.

It is understood that the positions of the components (relative to the anatomy) shown in FIG. 4 are considered exemplary final positions for the different components of working portion 1104, even if there was repositioning that occurred after initial deployment.

The one or more expandable members herein can be configured to be, and can be expanded in a variety of ways, such as via self-expansion, mechanical actuation (e.g., one or more axially directed forces on the expandable member, expanded with a separate balloon positioned radially within the expandable member and inflated to push radially outward on the expandable member), or a combination thereof.

Expansion as used herein refers generally to reconfiguration to a larger profile with a larger radially outermost dimension (relative to the longitudinal axis), regardless of the specific manner in which the one or more components are expanded. For example, a stent that self-expands and/or is subject to a radially outward force can "expand" as that term is used herein. A device that unfurls or unrolls can also assume a larger profile, and can be considered to expand as that term is used herein.

The impellers can similarly be adapted and configured to be, and can be expanded in a variety of ways depending on their construction. For examples, one or more impellers can, upon release from a sheath, automatically revert to or towards a different larger profile configuration due to the material(s) and/or construction of the impeller design (see, for example, U.S. Pat. No. 6,533,716, or U.S. Pat. No. 7,393,181, both of which are incorporated by reference herein for all purposes). Retraction of an outer restraint can thus, in some embodiments, allow both the expandable member and the impeller to revert naturally to a larger profile, deployed configuration without any further actuation.

As shown in the example in FIG. 4, the working portion includes first and second impellers that are spaced on either side of an aortic valve, each disposed within a separate expandable member. This is in contrast to some designs in which a working portion includes a single elongate expandable member. Rather than a single generally tubular expandable member extending all the way across the valve, working end 1104 includes a conduit 1112 extending between expandable members 1108 and 1110. The conduit is more flexible and deformable than the expandable baskets, which can allow for more deformation of the working portion at the location of the leaflets than would occur if an expandable member spanned the aortic valve leaflets. This can cause less damage to the leaflets after the working portion has been deployed in the subject.

Additionally, forces on a central region of a single expandable member from the leaflets might translate axially to other regions of the expandable member, perhaps causing undesired deformation of the expandable member at the locations of the one or more impellers. This may cause the outer expandable member to contact the impeller, undesirably interfering with the rotation of the impeller. Designs that include separate expandable members around each impeller, particularly where each expandable member and each impeller are supported at both ends (i.e., distal and proximal), result in a high level of precision in locating the impeller relative to the expandable member. Two separate expandable members may be able to more reliably retain their deployed configurations compared with a single expandable member.

As described herein above, it may be desirable to be able to reconfigure the working portion so that it can be delivered within a 9 F sheath and still obtain high enough flow rates when in use, which is not possible with some products currently in development and/or testing. For example, some products are too large to be able to reconfigured to a small enough delivery profile, while some smaller designs may not be able to achieve the desired high flow rates. An exemplary advantage of the examples in FIGS. 1, 2, 3A-3D and 4 is that, for example, the first and second impellers can work together to achieve the desired flow rates, and by having two axially spaced impellers, the overall working portion can be reconfigured to a smaller delivery profile than designs in which a single impeller is used to achieved the desired flow rates. These embodiments thus use a plurality of smaller, reconfigurable impellers that are axially spaced to achieve both the desired smaller delivery profile as well as to achieve the desired high flow rates.

The embodiment herein can thus achieve a smaller delivery profile while maintaining sufficiently high flow rates, while creating a more deformable and flexible central region of the working portion, the exemplary benefits of which are described above (e.g., interfacing with delicate valve leaflets).

Figure 5:
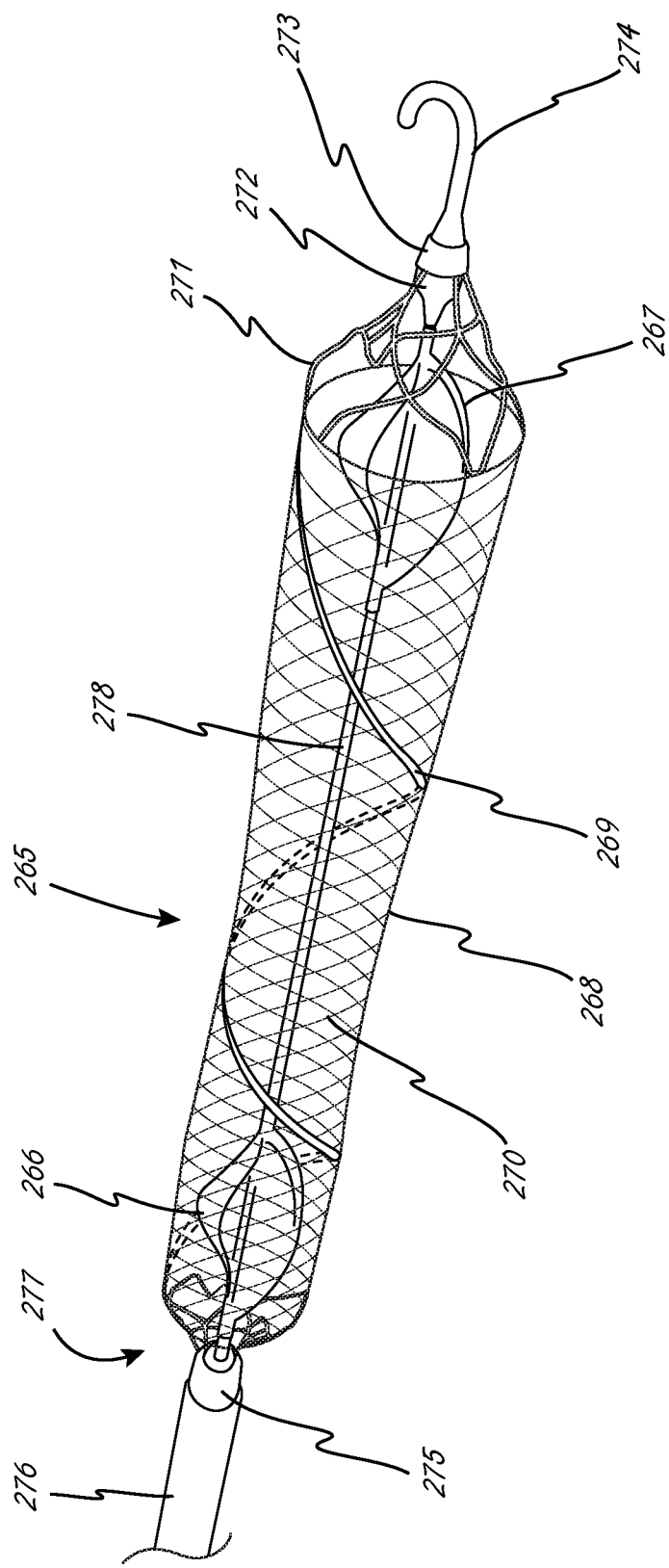
FIG. 5 illustrates an exemplary working portion.

FIG. 5 illustrates a working portion that is similar to the working portion shown in FIG. 1. Working portion 265 includes proximal impeller 266, distal impeller 267, both of which are coupled to drive shaft 278, which extends into distal bearing housing 272. There is a similar proximal bearing housing at the proximal end of the working portion. Working portion also includes expandable member, referred to 270 generally, and conduit 268 that is secured to the expandable member and extends almost the entire length of expandable member. Expandable member 270 includes distal struts 271 that extend to and are secured to strut support 273, which is secured to distal tip 273. Expandable member 270 also includes proximal struts there are secured to a proximal strut support. All features similar to that shown in FIG. 1 are incorporated by reference for all purposes into this embodiment even if not explicitly stated. Expandable member 265 also includes helical tension member 269 that is disposed along the periphery of the expandable member, and has a helical configuration when the expandable member is in the expanded configuration as shown. The helical tension member 269 is disposed and adapted to induce rotation wrap upon collapse. Working portion 265 can be collapsed from the shown expanded configuration while simultaneously rotating one or both impellers at a relatively slow speed to facilitate curled collapse of the impellers due to interaction with the expandable member. Helical tension member 269 (or a helical arrangement of expandable member cells) will act as a collective tension member and is configured so that when the expandable basket is pulled in tension along its length to collapse (such as by stretching to a much greater length, such as approximately doubling in length) tension member 269 is pulled into a straighter alignment, which causes rotation/twisting of the desired segment(s) of the expandable member during collapse, which causes the impeller blades to wrap radially inward as the expandable member and blades collapse. An exemplary configuration of such a tension member would have a curvilinear configuration when in helical form that is approximately equal to the maximum length of the expandable member when collapsed. In alternative embodiments, only the portion(s) of the expandable member that encloses a collapsible impeller is caused to rotate upon collapse.

There are alternative ways to construct the working portion to cause rotation of the expandable member upon collapse by elongation (and thus cause wrapping and collapse of the impeller blades). Any expandable member can be constructed with this feature, even in dual-impeller designs. For example, with an expandable member that includes a plurality of "cells," as that term is commonly known (e.g., a laser cut elongate member), the expandable member may have a plurality of particular cells that together define a particular configuration such as a helical configuration, wherein the cells that define the configuration have different physical characteristics than other cells in the expandable member. In some embodiments the expandable member can have a braided construction, and the twist region may constitute the entire group of wires, or a significant portion (e.g., more than half), of the braided wires. Such a twisted braid construction may be accomplished, for example, during the braiding process, such as by twisting the mandrel that the wires are braided onto as the mandrel is pulled along, especially along the length of the largest-diameter portion of the braided structure. The construction could also be accomplished during a second operation of the construction process, such as mechanically twisting a braided structure prior to heat-setting the wound profile over a shaped mandrel.

Any of the conduits herein act to, are configured to, and are made of material(s) that create a fluid lumen therein between a first end (e.g., distal end) and a second end (e.g., proximal end). Fluid flows into the inflow region, through the fluid lumen, and then out of an outflow region. Flow into the inflow region may be labeled herein as "I," and flow out at the outflow region may be labeled "O." Any of the conduits herein can be impermeable Any of the conduits herein can alternatively be semipermeable. Any of the conduits herein may also be porous, but will still define a fluid lumen therethrough. In some embodiments the conduit is a membrane, or other relatively thin layered member. Any of the conduits herein, unless indicated to the contrary, can be secured to an expandable member such that the conduit, where is it secured, can be radially inside and/or outside of the expandable member. For example, a conduit can extend radially within the expandable member so that inner surface of the conduit is radially within the expandable member where it is secured to the expandable member.

Any of the expandable member(s) herein can be constructed of a variety of materials and in a variety of ways. For example, the expandable member may have a braided construction, or it can be formed by laser machining. The material can be deformable, such as nitinol. The expandable member can be self-expanding or can be adapted to be at least partially actively expanded.

In some embodiments, the expandable member is adapted to self-expand when released from within a containing tubular member such as a delivery catheter, a guide catheter or an access sheath. In some alternative embodiments, the expandable member is adapted to expand by active expansion, such as action of a pull-rod that moves at least one of the distal end and the proximal end of the expandable member toward each other. In alternative embodiments, the deployed configuration can be influenced by the configuration of one or more expandable structures. In some embodiments, the one or more expandable members can deployed, at least in part, through the influence of blood flowing through the conduit. Any combination of the above mechanisms of expansion may be used.

The blood pumps and fluid movement devices, system and methods herein can be used and positioned in a variety of locations within a body. While specific examples may be provided herein, it is understood that that the working portions can be positioned in different regions of a body than those specifically described herein.

Figure 6A:
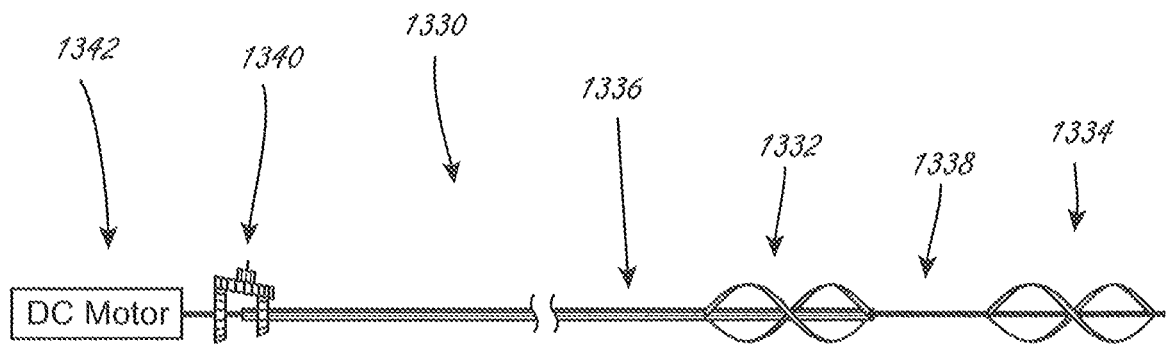
FIG. 6A illustrates at least a portion of an exemplary medical device that has a pump portion, where at least two different impellers can be rotated at different speeds.

In any of the embodiments herein in which the medical device includes a plurality of impellers, the device can be adapted such that the impellers rotate at different speeds. FIG. 6A illustrates a medical device that includes gearset 1340 coupled to both inner drive member 1338 and outer drive member 1336, which are in operable communication with distal impeller 1334 and proximal impeller 1332, respectively. The device also includes motor 1342, which drives the rotation of inner drive member 1338. Inner drive member 1338 extends through outer drive member 1336. Activation of the motor 1332 causes the two impellers to rotate at different speeds due to an underdrive or overdrive ratio. Gearset 1340 can be adapted to drive either the proximal or distal impeller faster than the other. Any of the devices herein can include any of the gearsets herein to drive the impellers at different speeds.

Figure 6B:
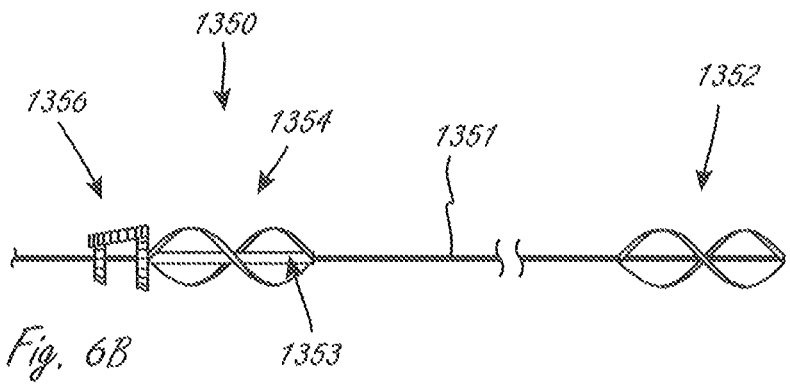
FIG. 6B illustrates at least a portion of an exemplary medical device that has a pump portion, where at least two different impellers can be rotated at different speeds.

FIG. 6B illustrates a portion of an alternative embodiment of a dual impeller device (1350) that is also adapted such that the different impellers rotate at different speeds. Gearset 1356 is coupled to both inner drive member 1351 and outer drive member 1353, which are coupled to distal impeller 1352 and proximal impeller 1354, respectively. The device also includes a motor like in FIG. 6A. FIGS. 6A and 6B illustrate how a gearset can be adapted to drive the proximal impeller slower or faster than the distal impeller.

Figure 7:
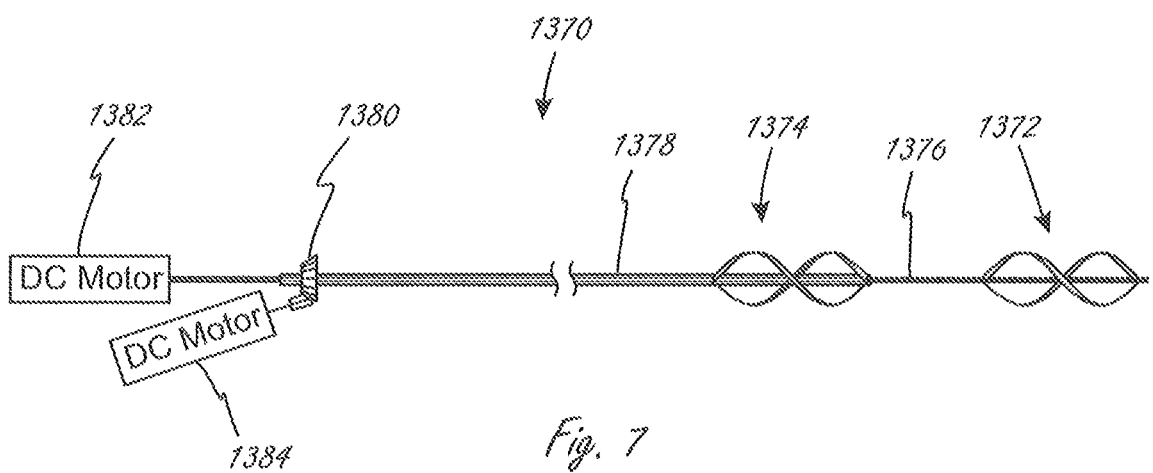
FIG. 7 illustrates at least a portion of an exemplary medical device that has a pump portion.

FIG. 7 shows an exemplary alternative embodiment of fluid pump 1370 that can rotate first and second impellers at different speeds. First motor 1382 drives cable 1376, which is coupled to distal impeller 1372, while second motor 1384 drives outer drive member 1378 (via gearset 1380), which is coupled to proximal impeller 1374. Drive cable 1376 extends through outer drive member 1378. The motors can be individually controlled and operated, and thus the speeds of the two impellers can be controlled separately. This system setup can be used with any system herein that includes a plurality of impellers.

Figure 6C:
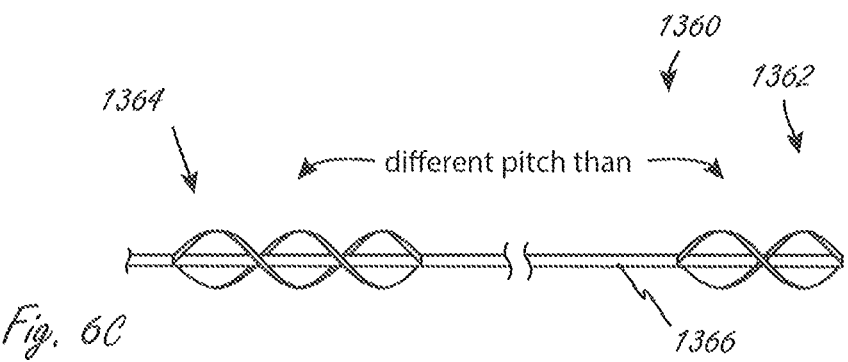
FIG. 6C illustrates at least a portion of an exemplary medical device that has a pump portion with at least two impellers with different pitches.

In some embodiments, a common drive cable or shaft can drive the rotation of two (or more) impellers, but the blade pitch of the two impellers (angle of rotational curvature) can be different, with the distal or proximal impeller having a steeper or more gradual angle than the other impeller. This can produce a similar effect to having a gearset. FIG. 6C shows a portion of a medical device (1360) that includes common drive cable 1366 coupled to proximal impeller 1364 and distal impeller 1362, and to a motor not shown. The proximal impellers herein can have a greater or less pitch than the distal impellers herein. Any of the working portions (or distal portions) herein with a plurality of impellers can be modified to include first and second impellers with different pitches.

In any of the embodiments herein, the pump portion can have a compliant or semi-compliant (referred to generally together as "compliant") exterior structure. In various embodiments, the compliant portion is pliable. In various embodiments, the compliant portion deforms only partially under pressure. For example, the central portion of the pump may be formed of a compliant exterior structure such that it deforms in response to forces of the valve. In this manner the exterior forces of the pump on the valve leaflets are reduced. This can help prevent damage to the valve at the location where it spans the valve.

Figure 8:
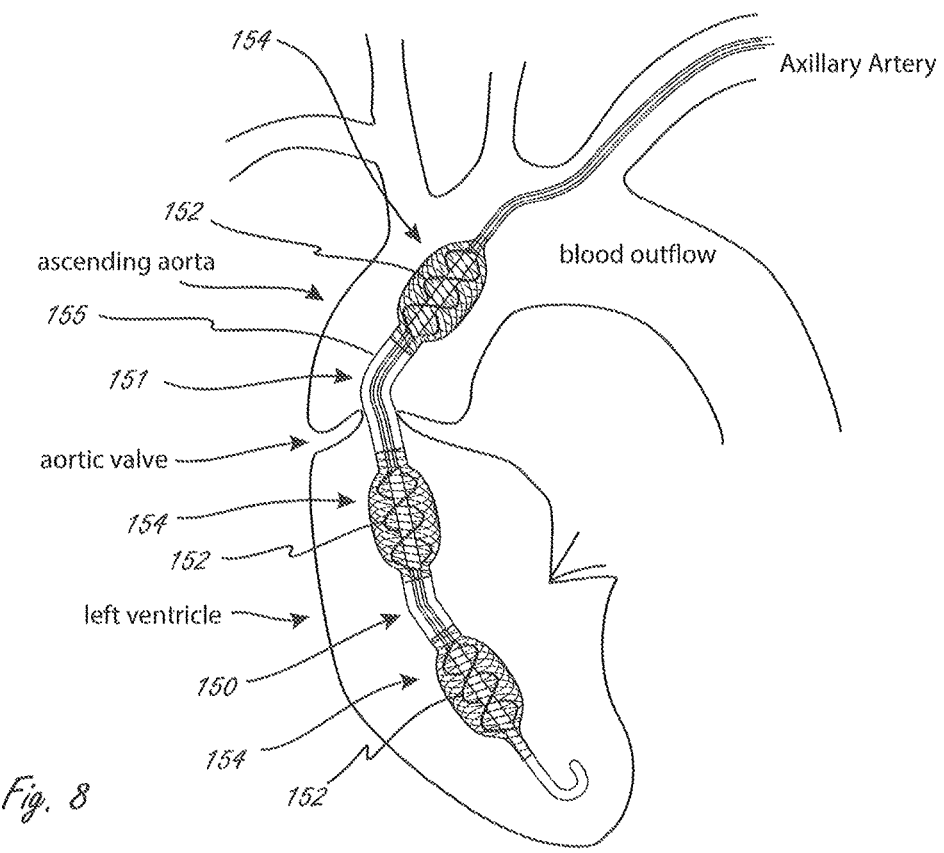
FIG. 8 illustrates a pump portion with multiple impellers, with a bend formed therein between adjacent impellers.

FIG. 8 illustrates an exemplary embodiment of a pump portion that includes first, second and third axially spaced impellers 152, each of which is disposed within an expandable member 154. Conduit 155 can extend along the length of the pump portion, as in described in various embodiments herein, which can help create and define the fluid lumen. In alternative embodiments, however, the first, second, and third impellers may be disposed within a single expandable member, similar to that shown in FIG. 1. In FIG. 8, a fluid lumen extends from a distal end to a proximal end, features of which are described elsewhere herein. The embodiment in FIG. 8 can include any other suitable feature, including methods of use, described herein.

The embodiment in FIG. 8 is also an example of an outer housing having at least one bend formed therein between a proximal impeller distal end and a distal impeller proximal end, such that a distal region of the housing distal to the bend is not axially aligned with a proximal region of the housing proximal to the bend along an axis. In this embodiment there are two bends 150 and 151 formed in the housing, each one between two adjacent impellers.

In a method of use, a bend formed in a housing can be positioned to span a valve, such as the aortic valve shown in FIG. 8. In this method of placement, a central impeller and distal-most impeller are positioned in the left ventricle, and a proximal-most impeller is positioned in the ascending aorta. Bend 151 is positioned just downstream to the aortic valve.

A bend such as bend 151 or 152 can be incorporated into any of the embodiments or designs herein. The bend may be a preformed angle or may be adjustable in situ.

In any of the embodiments herein, unless indicated to the contrary, the outer housing can have a substantially uniform diameter along its length.

In FIG. 8, the pump is positioned via the axillary artery, which is an exemplary method of accessing the aortic valve, and which allows the patient to walk and be active with less interruption. Any of the devices herein can be positioned via the axillary artery. One will appreciate from the description herein, however, that the pump may be introduced and tracked into position in various manner including a femoral approach over the aortic arch.

One aspect of the disclosure is an intravascular blood pump that includes a distal impeller axially spaced from a proximal impeller. In one embodiment, the distal and proximal impellers are separated from each other. For example, the distal and proximal impellers may be connected solely by their individual attachment to a common driveshaft. This is distinct from an impeller having multiple blade rows. A distal impeller as that phrase is used herein does not necessarily mean a distal-most impeller of the pump, but can refer generally to an impeller that is positioned further distally than a proximal impeller, even if there is an additional impeller than is disposed further distally than the distal impeller. Similarly, a proximal impeller as that phrase is used herein does not necessarily mean a proximal-most impeller of the pump, but can refer generally to an impeller that is positioned further proximally than a proximal impeller, even if there is an additional impeller than is disposed further proximally than the proximal impeller. Axial spacing (or some derivative thereof) refers to spacing along the length of a pump portion, such as along a longitudinal axis of the pump portion, even if there is a bend in the pump portion. In various embodiments, each of the proximal and distal impellers are positioned within respective housings and configured to maintain a precise, consistent tip gap, and the span between the impellers has a relatively more flexible (or completely flexible) fluid lumen. For example, each of the impellers may be positioned within a respective housing having relatively rigid outer wall to resist radial collapse. The sections between the impellers may be relatively rigid, in some embodiments the section is held open primarily by the fluid pressure within.

Although not required for the embodiments therein, there may be advantages to having a minimum axial spacing between a proximal impeller and a distal impeller. For example, a pump portion may be delivered to a target location through parts of the anatomy that have relatively tight bends, such as, for example, an aorta, and down into the aortic valve. For example, a pump portion may be delivered through a femoral artery access and to an aortic valve. It can be advantageous to have a system that is easier to bend so that it is easier to deliver the system through the bend(s) in the anatomy. Some designs where multiple impellers are quite close to each other may make the system, along the length that spans the multiple impellers, relatively stiff along that entire length that spans the multiple impellers. Spacing the impellers apart axially, and optionally providing a relatively flexible region in between the impellers, can create a part of the system that is more flexible, is easier to bend, and can be advanced through the bends more easily and more safely. An additional exemplary advantage is that the axial spacing can allow for a relatively more compliant region between the impellers, which can be positioned at, for example, the location of a valve (e.g., an aortic valve). Furthermore, there are other potential advantages and functional differences between the various embodiments herein and typical multistage pumps. A typical multistage pump includes rows of blades (sometimes referred to as impellers) in close functional spacing such that the rows of blades act together as a synchronized stage. One will appreciate that the flow may separate as it passes through the distal impeller. In various embodiments as described herein, distal and proximal impellers can be spaced sufficiently apart such that the flow separation from the distal impeller is substantially reduced (i.e., increased flow reattachment) and the localized turbulent flow is dissipated before the flow enters the proximal impeller.

Figure 9:
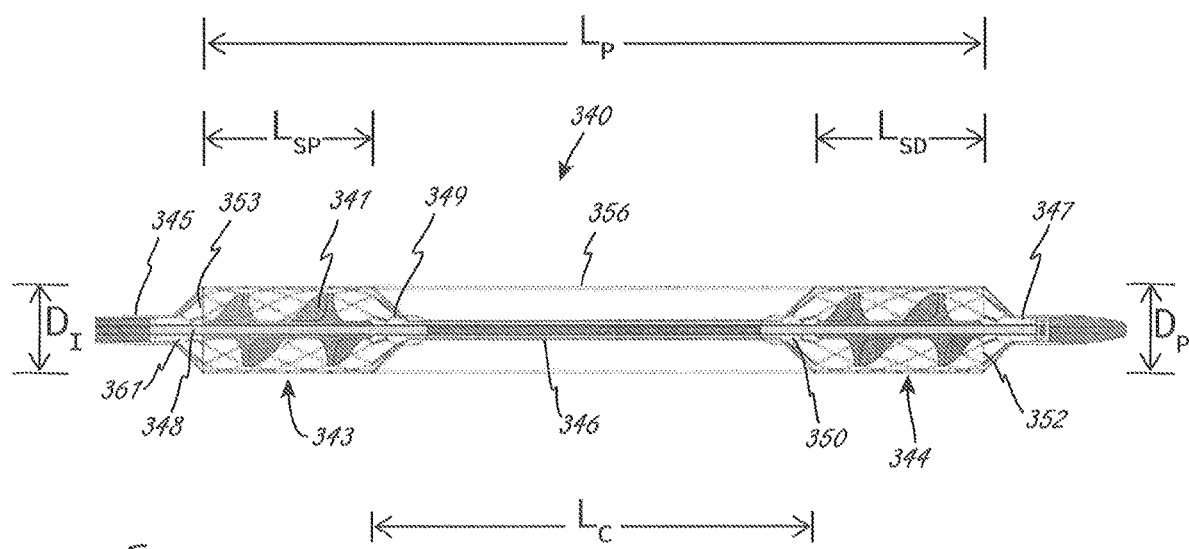
FIG. 9 illustrates a pump portion with a plurality of impellers.

In any of the embodiments or in any part of the description herein that include a distal impeller and a proximal impeller, the axial spacing between a distal end of the proximal impeller and a proximal end of the distal impeller can be from 1.5 cm to 25 cm (inclusive) along a longitudinal axis of the pump portion, or along a longitudinal axis of a housing portion that includes a fluid lumen. The distance may be measured when the pump portion, including any impellers, is in an expanded configuration. This exemplary range can provide the exemplary flexibility benefits described herein as the pump portion is delivered through curved portions of the anatomy, such as, for example, an aortic valve via an aorta. FIG. 9 (shown outside a patient in an expanded configuration) illustrates length Lc, which illustrates an axial spacing between impellers, and in some embodiments may be from 1.5 cm to 25 cm as set forth herein. In embodiments in which there may be more than two impellers, any two adjacent impellers (i.e., impellers that do not have any other rotating impeller in between them) may be spaced axially by any of the axial spacing distances described herein.

While some embodiments include a proximal impeller distal end that is axially spaced 1.5 cm to 25 cm from a distal impeller proximal end along an axis, the disclosure herein also includes any axial spacings that are subranges within that general range of 1.5 cm to 25 cm. That is, the disclosure includes all ranges that have any lower limit from 1.5 and above in that range, and all subranges that have any upper limit from 25 cm and below. The examples below provide exemplary subranges. In some embodiments, a proximal impeller distal end is axially spaced 1.5 cm to 20 cm from a distal impeller proximal end along an axis, 1.5 cm to 15 cm, 1.5 cm to 10 cm, 1.5 cm to 7.5 cm, 1.5 cm to 6 cm, 1.5 cm to 4.5 cm, 1.5 cm to 3 cm. In some embodiments the axial spacing is 2 cm to 20 cm, 2 cm to 15 cm, 2 cm to 12 cm, 2 cm to 10 cm, 2 cm to 7.5 cm, 2 cm to 6 cm, 2 cm to 4.5 cm, 2 cm to 3 cm. In some embodiments the axial spacing is 2.5 cm to 15 cm, 2.5 cm to 12.5 cm, 2.5 cm to 10 cm, 2.5 cm to 7.5 cm, or 2.5 cm to 5 cm (e.g., 3 cm). In some embodiments the axial spacing is 3 cm to 20 cm, 3 cm to 15 cm, 3 cm to 10 cm, 3 cm to 7.5 cm, 3 cm to 6 cm, or 3 cm to 4.5 cm. In some embodiments the axial spacing is 4 cm to 20 cm, 4 cm to 15 cm, 4 cm to 10 cm, 4 cm to 7.5 cm, 4 cm to 6 cm, or 4 cm to 4.5 cm. In some embodiments the axial spacing is 5 cm to 20 cm, 5 cm to 15 cm, 5 cm to 10 cm, 5 cm to 7.5 cm, or 5 cm to 6 cm. In some embodiments the axial spacing is 6 cm to 20 cm, 6 cm to 15 cm, 6 cm to 10 cm, or 6 cm to 7.5 cm. In some embodiments the axial spacing is 7 cm to 20 cm, 7 cm to 15 cm, or 7 cm to 10 cm. In some embodiments the axial spacing is 8 cm to 20 cm, 8 cm to 15 cm, or 8 cm to 10 cm. In some embodiments the axial spacing is 9 cm to 20 cm, 9 cm to 15 cm, or 9 cm to 10 cm. In various embodiments, the fluid lumen between the impellers is relatively unsupported.

In any of the embodiments herein the one or more impellers may have a length, as measured axially between an impeller distal end and an impeller proximal end (shown as "$L_{SD}$" and "$L_{SP}$", respectively, in FIG. 9), from 0.5 cm to 10 cm, or any subrange thereof. The examples below provide exemplary subranges. In some embodiments the impeller axial length is from 0.5 cm to 7.5 cm, from 0.5 cm to 5 cm, from 0.5 cm to 4 cm, from 0.5 cm to 3 cm, from 0.5 cm to 2, or from 0.5 cm to 1.5 cm. In some embodiments the impeller axial length is from 0.8 cm to 7.5 cm, from 0.8 cm to 5 cm, from 0.8 cm to 4 cm, from 0.8 cm to 3 cm, from 0.8 cm to 2 cm, or from 0.8 cm to 1.5 cm. In some embodiments the impeller axial length is from 1 cm to 7.5 cm, from 1 cm to 5 cm, from 1 cm to 4 cm, from 1 cm to 3 cm, from 1 cm to 2 cm, or from 1 cm to 1.5 cm. In some embodiments the impeller axial length is from 1.2 cm to 7.5 cm, from 1.2 cm to 5 cm, from 1.2 cm to 4 cm, from 1.2 cm to 3 cm, from 1.2 to 2 cm, or from 1.2 cm to 1.5 cm. In some embodiments the impeller axial length is from 1.5 cm to 7.5 cm, from 1.5 cm to 5 cm, from 1.5 cm to 4 cm, from 1.5 cm to 3 cm, or from 1.5 cm to 2 cm. In some embodiments the impeller axial length is from 2 cm to 7.5 cm, from 2 cm to 5 cm, from 2 cm to 4 cm, or from 2 cm to 3 cm. In some embodiments the impeller axial length is from 3 cm to 7.5 cm, from 3 cm to 5 cm, or from 3 cm to 4 cm. In some embodiments the impeller axial length is from 4 cm to 7.5 cm, or from 4 cm to 5 cm.

In any of the embodiments herein the fluid lumen can have a length from a distal end to a proximal end, shown as length Lp in FIG. 9. In some embodiments the fluid lumen length Lp is from 4 cm to 40 cm, or any subrange therein. For example, in some embodiments the length Lp can be from 4 cm to 30 cm, from 4 cm to 20 cm, from 4 cm to 18 cm, from 4 cm to 16 cm, from 4 cm to 14 cm, from 4 cm to 12 cm, from 4 cm to 10 cm, from 4 cm to 8 cm, from 4 cm to 6 cm.

In any of the embodiments herein the housing can have a deployed diameter, at least the location of an impeller (and optionally at a location between impellers), shown as dimension Dp in FIG. 9. In some embodiments Dp can be from 0.3 cm to 1.5 cm, or any subrange therein. For example, Dp may be from 0.4 cm to 1.4 cm, from 0.4 cm to 1.2 cm, from 0.4 cm to 1.0 cm, from 0.4 cm to 0.8 cm, or from 0.4 cm to 0.6 cm. In some embodiments, Dp may be from 0.5 cm to 1.4 cm, from 0.5 cm to 1.2 cm, from 0.5 cm to 1.0 cm, from 0.5 cm to 0.8 cm, or from 0.5 cm to 0.6 cm. In some embodiments Dp may be from 0.6 cm to 1.4 cm, from 0.6 cm to 1.2 cm, from 0.6 cm to 1.0 cm, or from 0.6 cm to 0.8 cm. In some embodiments Dp may be from 0.7 cm to 1.4 cm, from 0.7 cm to 1.2 cm, from 0.7 cm to 1.0 cm, or from 0.7 cm to 0.8 cm.

In any of the embodiments herein an impeller can have a deployed diameter, shown as dimension Di in FIG. 9. In some embodiments Di can be from 1 mm-30 mm, or any subrange therein. For example, in some embodiments Di may be from 1 mm-15 mm, from 2 mm-12 mm, from 2.5 mm-10 mm, or 3 mm-8 mm.

In any of the embodiments herein, a tip gap exists between an impeller outer diameter and a fluid lumen inner diameter. In some embodiments the tip gap can be from 0.01 mm-1 mm, such as 0.05 mm to 0.8 mm, or such as 0.1 mm-0.5 mm.

In any of the embodiments herein, at least one of a flow diffuser or diffusers and a stator or stators is/are located between two or more impellers along the catheter shaft. Such a flow diffuser may help to reduce swirl of the fluid and overall increase the efficiency of the multiple impellers as a group.

In any of the embodiments herein, features at the fluid exit of an expandable shroud basket or expandable member are shaped to act as a flow diffuser, such as stent-like struts at the attachments between the catheter shaft outer dimension and the expandable member outer dimension, which can be blade-shaped with a twist directed to change the flow direction of blood. In any of the embodiments herein, one or more portions of the catheter shaft downstream of an impeller may flare to a larger diameter to change the angle of blood flow and cause deceleration of the blood flow to a speed closer to native aortic blood flow. Exemplary locations for a larger diameter downstream of an impeller would be at or near the area where an expandable shroud basket attaches to the catheter shaft, and/or at a bearing housing adjacent the impeller, or on or adjacent an internal motor.

Figure 10:
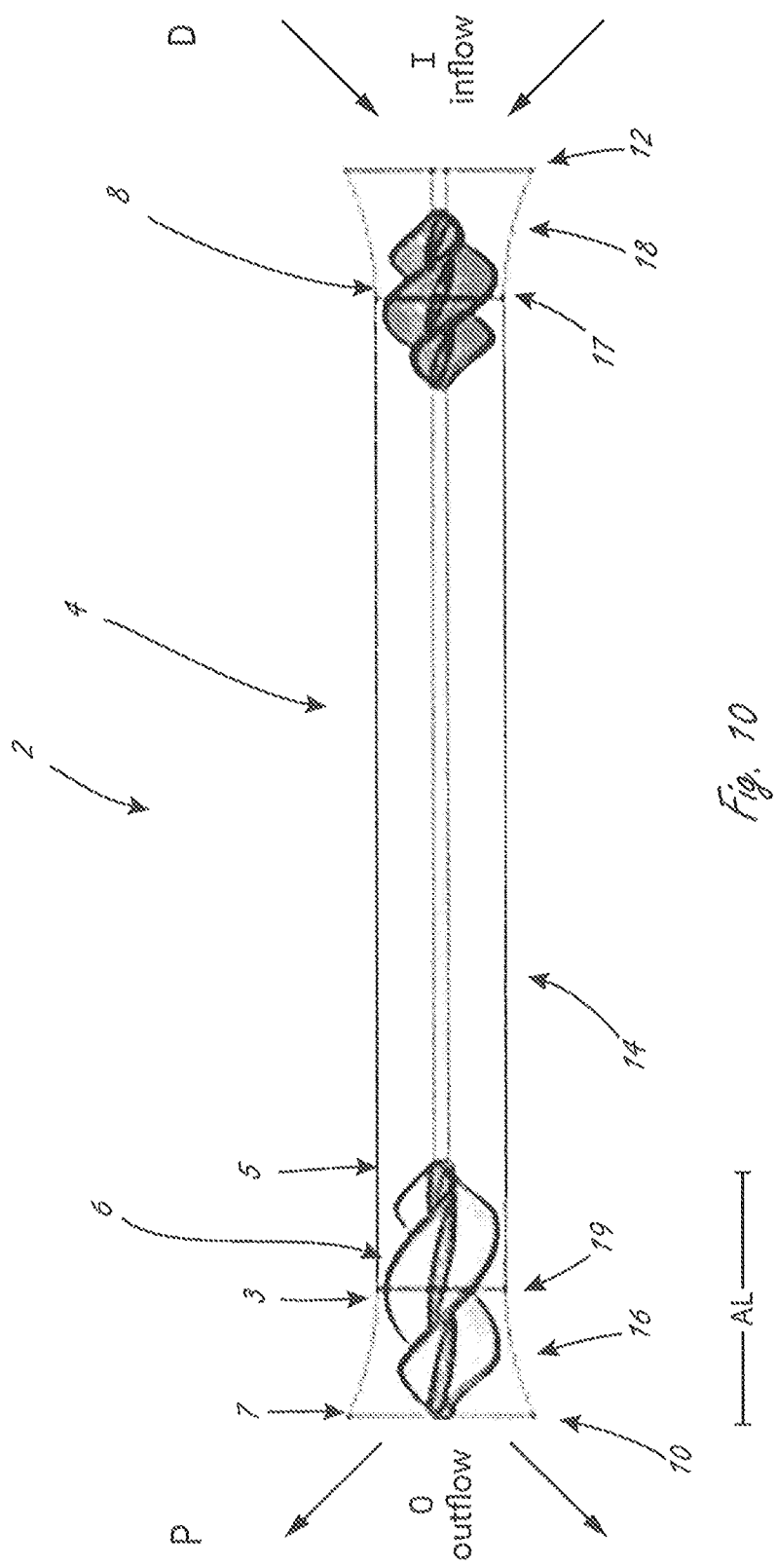
FIG. 10 is a side view of a portion of an exemplary pump portion.

FIG. 10 is a side view of an exemplary embodiment, and will be used as an exemplary embodiment based on experimental findings made by Applicant. FIG. 10 illustrates an exemplary configuration of a fluid lumen in an expanded configuration, as well as exemplary proximal and distal impellers, in expanded configurations. Other aspects of the pump portion are not shown for clarity, but it is understood that other aspects and features may be included in the pump portion as well as the overall system in general (such as other features described herein). FIG. 10 shows a portion of pump portion 2, which includes an expandable housing 4, proximal impeller 6 and distal impeller 8. Expandable housing 4 defines a fluid lumen (aspects of which are described in more detail herein), which in FIG. 10 includes a distal end 12 and proximal end 10. Inflow I and outflow O are illustrated at the distal and proximal ends respectively, which are described in more detail herein. While the general profile of the fluid lumen is shown in FIG. 10, expandable housing 4 may comprise one or more components, such as one or more expandable members (such as those described herein) and/or one or more conduits (such as those described herein). In some embodiments expandable housing 4 includes an expandable structure such as an expandable scaffolding and a deformable material (e.g., a membrane) secured to one another (see, e.g., FIG. 5). In some embodiments an expandable housing is formed from an expandable structure covered with an elastomeric polymer (e.g. polycarbonate urethane or polyurethane). The expandable structure may be a scaffold formed from NiTi, a mesh, and more. The expandable housing defines a fluid lumen therethrough when in the expanded configuration.

The configuration shown in FIG. 10 illustrates the fluid lumen configuration of the expandable housing when the expandable housing is in an expanded configuration. In this example, the fluid lumen includes a substantially constant diameter portion 14, a proximal region 16 with a flared configuration, and a distal region 18 with a flared configuration. In this context, the substantially constant diameter portion can be referred to herein simply as a constant diameter portion, and unless indicated to the contrary, this is meant to imply a substantially constant diameter portion, which is described in more detail herein. The constant diameter portion 14 has a proximal end 19 and a distal end 17. Distal end 17 of the constant diameter region is, in this example, also the proximal end of the distal flared region 18. Proximal end 19 of the constant diameter region is, in this example, also the distal end of the proximal flared region 16.

Part of this disclosure describes unexpected experimental results related to the performance of a pump portion when changing the position of a proximal impeller relative to one more aspects of the fluid lumen. This may be described as, for example, a position of a feature of the proximal impeller (e.g., proximal end, distal end, midpoint, percentage of length, etc.) relative to a position of one more features of the fluid lumen (e.g., proximal end of constant diameter portion, distal end of flared region, proximal end of fluid lumen, etc.).

Results included in this disclosure are based on experiments that altered the axial position of an impeller relative to the fluid lumen of a testing apparatus, while maintaining the configuration of the fluid lumen and the position of a distal impeller. The configuration of the testing apparatus can be used as a basis for the configuration of a portion of the pump portion, an example of which is shown in FIG. 10. FIGS. 11A-11E illustrate exemplary different positions of proximal impeller 6 relative to a fluid lumen of an experimental apparatus, a part of which can be used to mimic an expandable housing that includes a fluid lumen. A central region of the apparatus in FIGS. 11A-11E includes the embodiment in FIG. 10, and all aspects of FIG. 10 and the description thereof apply to FIGS. 11A-11E. The experiments were performed to, for example, characterize and understand how changes in axial position of the impeller can change flow and pressure. Hemolysis was also monitored when changing the axial position.

Figure 11A:
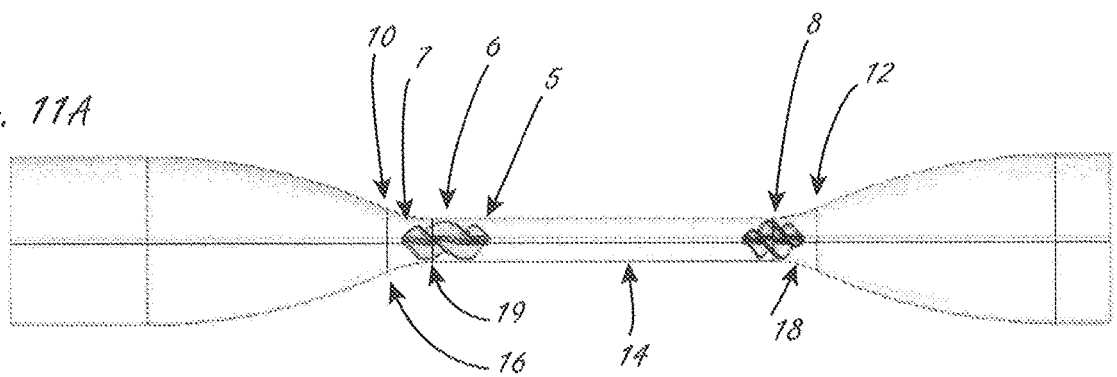
FIGS. 11A, 11B, 11C, 11D, and 11E illustrate exemplary testing, described in more detail herein.
Figure 11B:
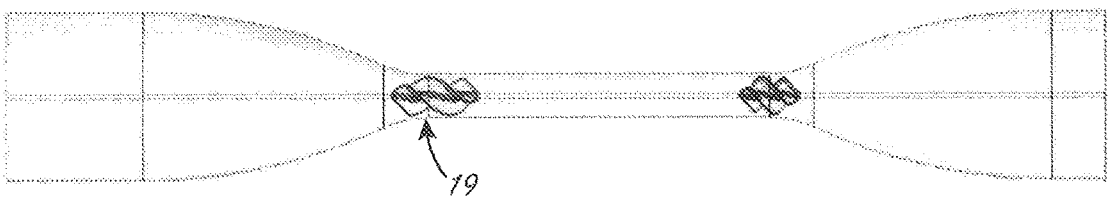
Figure 11C:
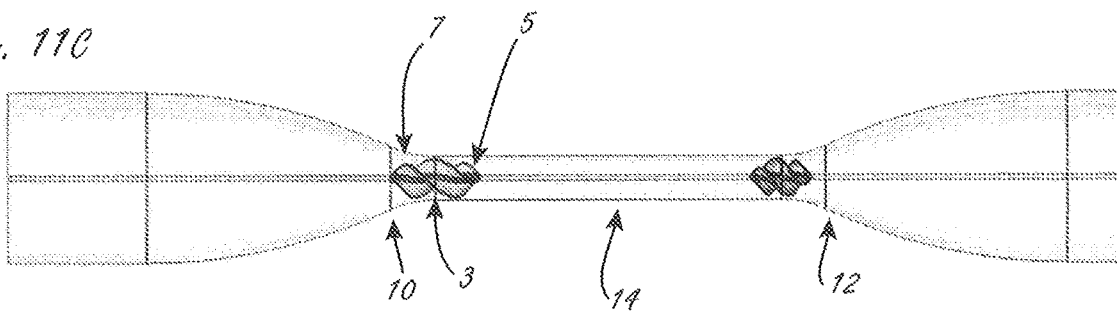
Figure 11D:
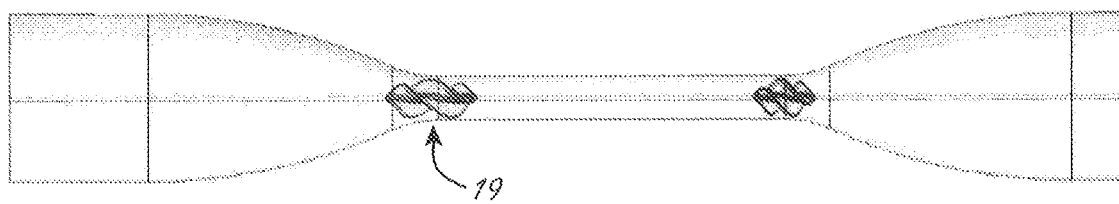
Figure 11E:
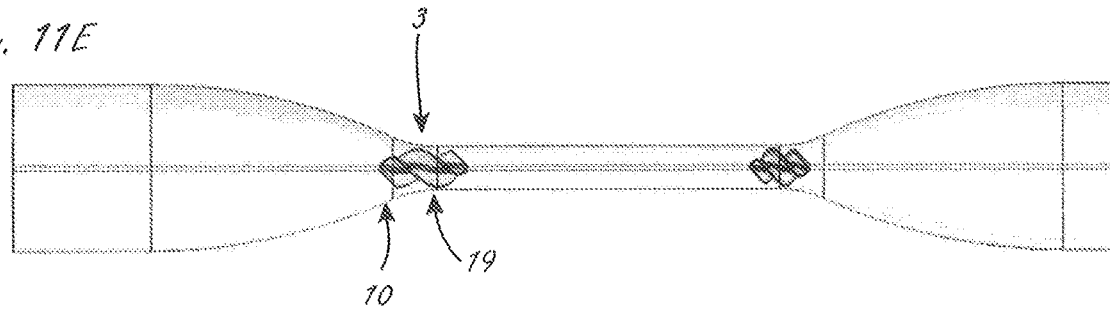

FIG. 11C illustrates what was treated as a baseline axial position for the proximal impeller. FIGS. 11B and 11A illustrate progressive distal movement of the impeller relative to the fluid lumen and relative to the baseline impeller position shown in FIG. 11C. FIGS. 11D and 11E illustrate progressive proximal movement of the impeller relative to the fluid lumen and relative to the baseline impeller position shown in FIG. 11C. The impeller is positioned furthest distally in FIG. 11A and furthest proximally in FIG. 11E.

In this exemplary embodiment and exemplary experiments, the impeller was moved axially in 1 mm increments. For example, the impeller is 1 mm further proximally in FIG. 11D relative to FIG. 11C. In the baseline position shown in FIG. 1C, a midpoint 3 of proximal impeller is axially aligned with a proximal end 19 of the substantially constant diameter portion 14 of the fluid lumen. In this position, a distal half of the impeller is thus disposed in the constant diameter portion 14, and a proximal half of the impeller is disposed in flared region 16.

In some embodiments, the proximal impeller can have an axial length "AL" (measured in the proximal-distal direction; see FIG. 10) of 9 mm, and 4.5 mm of the impeller is disposed in constant diameter portion 14 and 4.5 mm of the impeller is disposed in proximal flared region 16 in the baseline position in FIG. 11C. In FIG. 11A, 6.5 mm of the impeller is disposed in the constant diameter portion 14 and 2.5 mm of the impeller is disposed in flared proximal region 16. In FIG. 11B, 5.5 mm of the impeller is disposed in the constant diameter portion 14 and 3.5 mm of the impeller is disposed in flared proximal region 16. In FIG. 11D, 5.5 mm of the impeller is disposed in the constant diameter portion 14 and 3.5 mm of the impeller is disposed in flared proximal region 16. In FIG. 11E, 2.5 mm of the impeller is disposed in the constant diameter portion 14 and 6.5 mm of the impeller is disposed in flared proximal region 16.

In some embodiments, the proximal impeller can have an axial length "AL" (measured in the proximal-distal direction; see FIG. 10) of 10 mm, and 5 mm of the impeller is disposed in constant diameter portion 14 and 5 mm of the impeller is disposed in proximal flared region 16 in the baseline position in FIG. 11C. In FIG. 11A, 7 mm of the impeller is disposed in the constant diameter portion 14 and 3 mm of the impeller is disposed in flared proximal region 16. In FIG. 11B, 6 mm of the impeller is disposed in the constant diameter portion 14 and 4 mm of the impeller is disposed in flared proximal region 16. In FIG. 11D, 4 mm of the impeller is disposed in the constant diameter portion 14 and 6 mm of the impeller is disposed in flared proximal region 16. In FIG. 11E, 3 mm of the impeller is disposed in the constant diameter portion 14 and 7 mm of the impeller is disposed in flared proximal region 16.

In some embodiments, the proximal impeller can have an axial length "AL" (measured in the proximal-distal direction; see FIG. 10) of 11 mm, and 5.5 mm of the impeller is disposed in constant diameter portion 14 and 5.5 mm of the impeller is disposed in proximal flared region 16 in the baseline position in FIG. 11C. In FIG. 11A, 7.5 mm of the impeller is disposed in the constant diameter portion 14 and 3.5 mm of the impeller is disposed in flared proximal region 16. In FIG. 11B, 6.5 mm of the impeller is disposed in the constant diameter portion 14 and 4.5 mm of the impeller is disposed in flared proximal region 16. In FIG. 11D, 4.5 mm of the impeller is disposed in the constant diameter portion 14 and 6.5 mm of the impeller is disposed in flared proximal region 16. In FIG. 11E, 3.5 mm of the impeller is disposed in the constant diameter portion 14 and 7.5 mm of the impeller is disposed in flared proximal region 16.

In some embodiments, the proximal impeller can have an axial length "AL" (measured in the proximal-distal direction; see FIG. 10) of 12 mm, and 6 mm of the impeller is disposed in constant diameter portion 14 and 6 mm of the impeller is disposed in proximal flared region 16 in the baseline position in FIG. 11C. In FIG. 11A, 8 mm of the impeller is disposed in the constant diameter portion 14 and 4 mm of the impeller is disposed in flared proximal region 16. In FIG. 11B, 7 mm of the impeller is disposed in the constant diameter portion 14 and 5 mm of the impeller is disposed in flared proximal region 16. In FIG. 11D, 5 mm of the impeller is disposed in the constant diameter portion 14 and 7 mm of the impeller is disposed in flared proximal region 16. In FIG. 11E, 4 mm of the impeller is disposed in the constant diameter portion 14 and 8 mm of the impeller is disposed in flared proximal region 16.

In some embodiments, the proximal impeller can have an axial length "AL" (measured in the proximal-distal direction; see FIG. 10) of 13 mm, and 6.5 mm of the impeller is disposed in constant diameter portion 14 and 6.5 mm of the impeller is disposed in proximal flared region 16 in the baseline position in FIG. 11C. In FIG. 11A, 8.5 mm of the impeller is disposed in the constant diameter portion 14 and 4.5 mm of the impeller is disposed in flared proximal region 16. In FIG. 11B, 7.5 mm of the impeller is disposed in the constant diameter portion 14 and 5.5 mm of the impeller is disposed in flared proximal region 16. In FIG. 11D, 5.5 mm of the impeller is disposed in the constant diameter portion 14 and 7.5 mm of the impeller is disposed in flared proximal region 16. In FIG. 11E, 4.5 mm of the impeller is disposed in the constant diameter portion 14 and 8.5 mm of the impeller is disposed in flared proximal region 16.

In some embodiments, the proximal impeller can have an axial length "AL" (measured in the proximal-distal direction; see FIG. 10) of 14 mm, and 7 mm of the impeller is disposed in constant diameter portion 14 and 7 mm of the impeller is disposed in proximal flared region 16 in the baseline position in FIG. 11C. In FIG. 11A, 9 mm of the impeller is disposed in the constant diameter portion 14 and 5 mm of the impeller is disposed in flared proximal region 16. In FIG. 11B, 8 mm of the impeller is disposed in the constant diameter portion 14 and 6 mm of the impeller is disposed in flared proximal region 16. In FIG. 11D, 6 mm of the impeller is disposed in the constant diameter portion 14 and 8 mm of the impeller is disposed in flared proximal region 16. In FIG. 11E, 5 mm of the impeller is disposed in the constant diameter portion 14 and 9 mm of the impeller is disposed in flared proximal region 16.

In some embodiments, the proximal impeller can have an axial length "AL" (measured in the proximal-distal direction; see FIG. 10) of 15 mm, and 7.5 mm of the impeller is disposed in constant diameter portion 14 and 7.5 mm of the impeller is disposed in proximal flared region 16 in the baseline position in FIG. 11C. In FIG. 11A, 9.5 mm of the impeller is disposed in the constant diameter portion 14 and 5.5 mm of the impeller is disposed in flared proximal region 16. In FIG. 11B, 8.5 mm of the impeller is disposed in the constant diameter portion 14 and 6.5 mm of the impeller is disposed in flared proximal region 16. In FIG. 11D, 6.5 mm of the impeller is disposed in the constant diameter portion 14 and 8.5 mm of the impeller is disposed in flared proximal region 16. In FIG. 11E, 5.5 mm of the impeller is disposed in the constant diameter portion 14 and 9.5 mm of the impeller is disposed in flared proximal region 16.

In some embodiments, the proximal impeller can have an axial length "AL" (measured in the proximal-distal direction; see FIG. 10) of 16 mm, and 8 mm of the impeller is disposed in constant diameter portion 14 and 8 mm of the impeller is disposed in proximal flared region 16 in the baseline position in FIG. 11C. In FIG. 11A, 10 mm of the impeller is disposed in the constant diameter portion 14 and 6 mm of the impeller is disposed in flared proximal region 16. In FIG. 11B, 9 mm of the impeller is disposed in the constant diameter portion 14 and 7 mm of the impeller is disposed in flared proximal region 16. In FIG. 11D, 7 mm of the impeller is disposed in the constant diameter portion 14 and 9 mm of the impeller is disposed in flared proximal region 16. In FIG. 11E, 6 mm of the impeller is disposed in the constant diameter portion 14 and 10 mm of the impeller is disposed in flared proximal region 16.

In some embodiments, the proximal impeller can have an axial length "AL" (measured in the proximal-distal direction; see FIG. 10) of 17 mm, and 8.5 mm of the impeller is disposed in constant diameter portion 14 and 8.5 mm of the impeller is disposed in proximal flared region 16 in the baseline position in FIG. 11C. In FIG. 11A, 10.5 mm of the impeller is disposed in the constant diameter portion 14 and 6.5 mm of the impeller is disposed in flared proximal region 16. In FIG. 11B, 9.5 mm of the impeller is disposed in the constant diameter portion 14 and 7.5 mm of the impeller is disposed in flared proximal region 16. In FIG. 11D, 7.5 mm of the impeller is disposed in the constant diameter portion 14 and 9.5 mm of the impeller is disposed in flared proximal region 16. In FIG. 11E, 6.5 mm of the impeller is disposed in the constant diameter portion 14 and 10.5 mm of the impeller is disposed in flared proximal region 16.

The relative positions of the proximal impeller portions can also be described as percentages of impeller length rather than length dimensions. In FIG. 11A, 35% of the length of the proximal impeller is disposed proximal to the constant diameter portion 14 and 65% of the length of the impeller is disposed in the constant diameter portion 14. In FIG. 11B, 42% of the length of the proximal impeller is disposed proximal to the constant diameter portion 14 and 58% of the length of the impeller is disposed in the constant diameter portion 14. In FIG. 11C, 50% of the length of the proximal impeller is disposed proximal to the constant diameter portion 14 and 50% of the length of the impeller is disposed in the constant diameter portion 14. In FIG. 11D, 58% of the length of the proximal impeller is disposed proximal to the constant diameter portion 14 and 42% of the length of the impeller is disposed in the constant diameter portion 14. In FIG. 11E, 65% of the length of the proximal impeller is disposed proximal to the constant diameter portion 14 and 35% of the length of the impeller is disposed in the constant diameter portion 14.

In the experiment, the pump portion of the testing apparatus was operated at a constant rotation rate of 30,500 RPM, and flow rates were measured for the different axial positions of the proximal impeller based a constant rotation rate. Estimated flow rates are provided herein, that were extrapolated to 60 mm Hg relative to the baseline position shown in FIG. 11C. The flow rate of the pump portion when the impeller was in the position in FIG. 11D was about 5% more than the flow rate of the baseline position in FIG. 11C (e.g., 4.9% more). The flow rate of the pump portion when the impeller was in the position in FIG. 11E was about 11% more than the flow rate of the baseline position in FIG. 11C (e.g., 10.7% more). The flow rate of the pump portion when the impeller was in the position in FIG. 11B was about 18% less than the flow rate of the baseline position in FIG. 11C (e.g., 18.2% less). The flow rate of the pump portion when the impeller was in the position in FIG. 11A was about 41% less than the flow rate of the baseline position in FIG. 11C (e.g., 41.2% less). This information is also presented in the table below.

TABLE 1

|  | Midpoint of impeller relative to proximal end of constant diameter portion (mm) | % of the proximal impeller axial length that is proximal to constant diameter portion | Impact on flow (relative to FIG. C) |
| --- | --- | --- | --- |
| FIG. 11A | −2 mm | 35% | 41% decrease |
| FIG. 11B | −1 mm | 42% | 18% decrease |
| FIG. 11C | 0 | 50% | Baseline |
| FIG. 11D | 1 mm | 58% | 5% increase |
| FIG. 11E | 2 mm | 65% | 11% increase |

The magnitude of the differences in the measured flows rate due to relatively small changes in axial positioning were unexpected and surprising. These unexpected results indicated that relatively small changes in axial position can dramatically change the flow rate. The experimental results also indicated that for pump portion designs in which a distal region of a proximal impeller is positioned in a substantially constant diameter region of a fluid lumen and a proximal region is disposed proximal to the substantially constant diameter region, there are positions or locations where the impeller can be placed that will result in more favorable flow rates relative to other positions. Alternatively stated, there are positions or locations where the impeller can be positioned, relative to the constant diameter portion, that may result in suboptimal flow rates, and even flow rates that could prevent the pump portion from achieving desired operating parameters.

One aspect of the disclosure is an intravascular blood pump that includes an impeller, optionally a proximal impeller, wherein a portion of the proximal impeller is disposed in a substantially constant diameter portion of a fluid lumen and a portion is disposed outside of the substantially constant diameter portion. The embodiment in FIG. 10 is an example of this aspect. As shown by the experimental results herein, there can be significant changes in flow by moving a proximal impeller relative to the fluid lumen, such as by changing the length of the impeller that extends proximally beyond a proximal end of a substantially constant diameter region of a fluid lumen. The data presented herein illustrates observed changes in pump portion performance based on exemplary tests and modeling. While some exemplary relative positions herein illustrate some noticed improvements in pump performance, it is contemplated that additional relative positions not specifically tested herein may provide benefits to pump performance, even if not specifically tested herein, and even if the improvements are not as dramatic as some other improvements herein. The disclosure and ranges below may thus provide pump portion performance that is improved relative to other impeller positions, and are considered part of the disclosure herein. Even if claims presented herein include one or more aspects of the disclosure more closely related to the experimental results, it is intended that the disclosure include other quantitative or qualitative aspects that may not be specifically described in the experimental results. For example, for some impellers designs, flow may be optimized or desired if 20% to 40% of a proximal impeller extends proximally beyond a proximal end of a constant diameter portion.

In some embodiments, at least 20% and up to 90% of the impeller (axial length) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, optionally up to 35% of the impeller, optionally up to 30% of the impeller, optionally up to 25% of the impeller, is disposed proximal to a proximal end of the constant diameter portion.

In some embodiments, at least 25% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 30% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 35% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller, optionally up to 40% of the impeller, is disposed proximal to a proximal end of the constant diameter portion.

In some embodiments, at least 40% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller, optionally up to 45% of the impeller is disposed proximal to a proximal end of the constant diameter portion.

In some embodiments, at least 45% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller, optionally up to 50% of the impeller is disposed proximal to a proximal end of the constant diameter portion.

In some embodiments, at least 50% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller, optionally up to 55% of the impeller is disposed proximal to a proximal end of the constant diameter portion.

In some embodiments, at least 55% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller, optionally up to 60% of the impeller is disposed proximal to a proximal end of the constant diameter portion.

In some embodiments, at least 60% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller, optionally up to 65% of the impeller is disposed proximal to a proximal end of the constant diameter portion.

In some embodiments, at least 65% and up to 90% of the impeller (measured axially) is disposed proximal to a proximal end of the constant diameter portion, optionally up to 85% of the impeller, optionally up to 80% of the impeller, optionally up to 75% of the impeller, optionally up to 70% of the impeller is disposed proximal to a proximal end of the constant diameter portion.

In some embodiments, at least 70% and up to 90% of the impeller (measured axially) is disposed proximal to a proximal end of the constant diameter portion, optionally up to 85% of the impeller, optionally up to 80% of the impeller, optionally up to 75% of the impeller, is disposed proximal to a proximal end of the constant diameter portion.

In some embodiments, at least 75% and up to 90% of the impeller (measured axially) is disposed proximal to a proximal end of the constant diameter portion, optionally up to 85% of the impeller, optionally up to 80% of the impeller is disposed proximal to a proximal end of the constant diameter portion.

In some embodiments, at least 80% and up to 90% of the impeller (measured axially) is disposed proximal to a proximal end of the constant diameter portion, optionally up to 85% of the impeller is disposed proximal to a proximal end of the constant diameter portion.

While FIG. 10 illustrates a portion of an exemplary portion that is taken from the testing apparatus in FIG. 11C, it is understood that the disclosure also includes pump portions that are generally shown in FIG. 10, but include proximal impellers that are have relative positions shown in FIGS. 11D and 11E. This disclosure thus implicitly and inherently includes pump portions that include all of the features of FIG. 10, but are as modified as shown in FIGS. 11A, 11B, 11D, and 11E, even though those figures are not expressly provided herein.

Some pump portions herein may have a proximal impeller that extends proximally beyond a proximal end of a fluid lumen. For example, the proximal impellers shown in FIGS. 11D and 11E, when incorporated into a pump portion such as that shown in FIG. 10, extend proximally beyond a proximal end of a fluid lumen.

Some of the fluid lumens herein have one or more end regions that have one or more surface that behave as a fluid diffuser. For example, flared proximal region 16 in FIG. 10 is an example of a proximal end region that has one or more surfaces that function as a fluid diffuser for turbulent flow. Any of the disclosure herein related to axial impeller position relative to a fluid lumen can apply to fluid lumens herein that have one or more end regions that have one or more surfaces that behave as a fluid diffuser.

Some of the fluid lumens herein have one or more end regions that have a flared configuration. For example, proximal region 16 in FIG. 10 is an example of a proximal fluid lumen region that has a flared configuration. Any of the disclosure herein related to axial impeller position relative to a fluid lumen can apply to fluid lumens herein that have a proximal region with a flared configuration. As used herein, a flared configuration refers generally to configurations that progressively extend further radially outward. A flared configuration might, but does not necessarily require, a configuration that continuously extends further radially outward along the entire axial length of the flared region. FIG. 10 is an example of a continuous flared configuration. Other configurations are possible in which only a portion of the proximal region has a continuous flare while other portions of the proximal region do not include a continuous flare. For example, a proximal region could include a step wise configuration with one or more continuous flared regions.

In some embodiments the flared configuration can be described in terms of a change in radial dimension (compared to the radial dimension of a substantially constant diameter region) per change in axial length. In any of the embodiments herein the flared configuration can have a mean (or average) change in radius per change in axial length that is from 5-100%, such as 10-75%, such as 15-50%, or such as 20-30%.

In any of the embodiments herein, the outlet may have an asymmetrical shape, e.g., a torus shape to promote centrifugal flow. The flared outlet does not need to have a smooth surface. For example, the outlet walls may have edges or sharp curves. The outlet walls may be non-planar (e.g., dimpled surfaces).

One aspect of the exemplary embodiment shown in FIG. 10 (including any pump portions that are modified versions of FIG. 10 and include relative impeller positions shown in FIGS. 11A, 11B, 11D, and 11E) is that the impeller and fluid lumen configurations shown (including the proximal end configuration of the fluid lumen) described provide for change in flow rates as the position of the impeller is changed. One exemplary aspect of incorporating the impeller and fluid lumen configurations shown in FIGS. 10 and 11A-11E is that when the proximal impeller is moved at least 2 mm proximally relative to an initial position, and moved so that less of the proximal impeller is (but not all of it) disposed in a substantially constant diameter portion of the fluid lumen, the flow rate of the pump portion, at 60 mm Hg, increases at least 10%. The initial position may be a position where the midpoint of the impeller is axially aligned with a proximal end of the substantially constant diameter portion. Another exemplary aspect of incorporating the impeller and fluid lumen configurations shown in FIGS. 10 and 11A-11E is that when the proximal impeller is moved at least 2 mm distally relative to an initial position, and moved so that more of the proximal impeller is (but not all of it) disposed in a substantially constant diameter portion of the fluid lumen, the flow rate of the pump portion, at 60 mm Hg, decreases at least 40%. Again, the initial position may be a position where the midpoint of the impeller is axially aligned with a proximal end of the substantially constant diameter portion.

One aspect of this disclosure is an intravascular blood pump with a collapsible housing comprising a fluid lumen, the fluid lumen having a distal end and a proximal end. The blood pump also includes a collapsible distal impeller axially spaced from a collapsible proximal impeller, the distal impeller having an expanded configuration and the proximal impeller having an expanded configuration. At least a portion of the distal and proximal impellers is disposed between the distal and proximal ends of the fluid lumen. The embodiments in FIGS. 10 and 11A-11E are examples of this aspect. In the exemplary embodiments of FIGS. 11D and 11E, the proximal impeller is configured to generate more 50% of the pressure generated by the blood pump, and the distal impeller is configured to generate less than 50% of the pressure generated by the blood pump. This can alternatively be stated as the proximal impeller is configured to do more than 50% of the work of the blood pump, with the distal impeller configured to do less than 50% of the work of the blood pump. In this context, work is a function of pressure and volume. Since the flow rate (volume of fluid per unit time) through the pump is generally the same for both impellers, each impeller can be configured to have a different contribution to the pressure generated by the pump, which can be different by design.

In the embodiment in FIG. 10, the blood pump does not include a vane assembly, stator blade, or any other flow modifying structures axially between the proximal and distal impellers.

In some embodiments, the proximal impeller generates more than 55% of the pressure generated by the blood pump, and the distal impeller generates less than 45% of the pressure generated by the blood pump. In some embodiments, the proximal impeller generates more than 60% of the pressure of the blood pump, and the distal impeller generates less than 40% of the pressure of the blood pump. In some embodiments, the proximal impeller generates more than 70% of the pressure of the blood pump, and the distal impeller generates less than 30% of the pressure of the blood pump. In some embodiments, the proximal impeller generates about 80% of the pressure of the blood pump, and the distal impeller generates about 20% of the pressure of the blood pump.

For any of the disclosure herein referring to the distal and proximal impellers generating a certain percentage of the pressure generated the pump, pressure measurements can be taken at a location distal to the distal impeller, at a location axially in between the impellers, and a location proximal to the proximal impeller, so that pressure differentials for each impeller can be calculated.

One aspect of this disclosure is a method of intravascularly pumping blood in a subject. The method can include positioning a pump housing fluid lumen first end in a first anatomical region (such as a left ventricle), positioning a distal impeller of the blood pump in the first anatomical region (such as a left ventricle), positioning a proximal impeller of the blood pump in a second anatomical location (such as an ascending aorta), positioning a pump housing fluid lumen second end in the second anatomical location (such as an ascending aorta), positioning at least a portion of a central region of the fluid lumen across an anatomical location (such as an aortic valve), and creating a flow path between the fluid lumen first end positioned in the first anatomical location (e.g., left ventricle) and the fluid lumen second end positioned in the second anatomical location (e.g., ascending aorta) such that the distal impeller and the proximal impeller can pump blood through the fluid lumen. The method can include rotating the distal impeller and proximal impeller, thereby pumping blood, which results in the proximal impeller generating more than 50% of the pressure generated by the blood pump and the distal impeller generating less than 50% of the pressure generated by the blood pump. The method can include the distal and proximal impellers generating any amount of pressure as is described herein. Any other suitable method step can be included in this method aspect unless specifically indicated to the contrary. The method can alternatively be stated as, instead of the individual impellers generating more or less than a particular percentage of pressure generated by the pump, the individual impellers can be performing more than or less than a percentage of work of the blood pump.

It has been found that distributing loads over two impellers (as is described herein), compared to single impeller designs, can lead to higher pump efficiency, lower pump speeds, and thus a decrease in hemolysis.

In FIGS. 10A and 11A-E, the proximal region of the impeller that is disposed outside of the substantially constant diameter region of the fluid lumen may be referred to as a proximal impeller region that is disposed proximal to a proximal end of the substantially constant diameter region, regardless of the specific configuration of the fluid lumen proximal to the constant diameter region. In FIGS. 10 and 11A-11E, a portion of the proximal impeller is disposed in the substantially constant diameter portion.

The test apparatus shown in FIGS. 11A-11E includes proximal and distal region that are not included in the exemplary fluid lumen in the embodiment in FIG. 10. While those enlarged portions are not included in the exemplary fluid lumen in FIG. 10, those regions may in some circumstances approximate one or more anatomical regions in which the pump portion is positioned. The term approximate in this context refers to having some characteristics of an anatomical location even if the actual anatomical features are different in one or more, and perhaps many, regards. For example, the enlarged proximal region in FIGS. 11A-E may in some ways be similar to one or more aspects of an ascending aorta, even if an ascending aorta is different in some regards.

The disclosure herein includes some embodiments of a pump portion that are described as having a fluid lumen with a substantially constant diameter portion. For example, the embodiment in FIG. 10 includes a substantially constant diameter portion 14. The phrase substantially constant can include some degree of variation in diameter. For example, some expandable housings herein include a reinforcing structure (which may be referred to as an expandable member) and a conduit such a membrane secured to the reinforcing structure. The manner in which these two components may be secured or assembled together can cause some minor variation in diameter. For example, if a membrane is applied to inner and/or outer surfaces of a reinforcing member (e.g., one or more stent-like devices), there may be slight variations in diameter between the locations where the membrane is positioned on an external or internal surface of the reinforcing and locations directly adjacent to those secured locations where a reinforcing member is not present. Those differences may be of small order (e.g. millimeters or microns), but even if they are larger, the intent is that those types of variations fall within the umbrella phrase of substantially constant. An alternative way of interpreting the phrase substantially constant is that the design of the fluid lumen in that region is intended to have as near as possible a constant diameter, even if particular designs or manufacturing constraints cause it to have some variation. A further alternative way of interpreting substantially constant is to inquire if the region of the fluid lumen is intended, from a design and functionality perspective, to have a variable diameter in that region. If the intent is to have a variable diameter and for the variable diameter to impart particular functionality, it may fall outside the scope of a substantially constant diameter portion. One of skill will appreciate from the description herein that the substantially constant diameter portion does not need to be formed as a tube and may take a variety of forms and shapes. As used herein, substantially constant diameter portion may refer to the main section of the fluid lumen. In certain embodiments, this section has a substantially constant diameter to reduce flow disturbances along the inner walls of the lumen and/or reduce the risk of trauma to the outer anatomy (e.g., the aortic valve leaflets). However, this section may take other forms depending on the application. For example, this portion may have dimples, curves, and the like to modify the flow therethrough as desired. In certain embodiments, substantially constant diameter portion may merely refer to the main portion of the fluid lumen as differentiated from the inlet and outlet portions.

Any of the other disclosure herein may be incorporated into the FIG. 10 embodiment unless specifically indicated to the contrary. For example, any of the suitable expandable structures can be incorporated into the embodiment in FIG. 10.

What is claimed is:

1. An intravascular blood pump, comprising:
   a collapsible housing comprising a fluid lumen, the fluid lumen having a distal end and a proximal end;
   a collapsible distal impeller axially spaced from a collapsible proximal impeller, the distal impeller having an expanded configuration and the proximal impeller having an expanded configuration, and at least a portion of each of the distal and proximal impellers disposed between the distal and proximal ends of the fluid lumen,
   wherein the proximal impeller and the distal impeller are each, when in their expanded configurations and when rotated, positioned relative to the fluid lumen such that the proximal impeller is performing more than 50% of the work of the blood pump and the distal impeller is performing less than 50% of the work of the blood pump.

2. The blood pump of claim 1, wherein the blood pump does not include a vane disposed axially between the proximal and distal impellers.

3. The blood pump of claim 1, wherein the blood pump does not include a stator blade disposed axially between the proximal and distal impellers.

4. The blood pump of claim 1, wherein at least half of the proximal impeller, measured along an axial length, is disposed proximal to a proximal end of a substantially constant diameter portion of the fluid lumen.

5. The blood pump of claim 4, wherein at least 50% of the proximal impeller, measured along an axial length, is disposed proximal to a proximal end of a substantially constant diameter portion of the fluid lumen.

6. The blood pump of claim 4, wherein at least 55% of the proximal impeller, measured along an axial length, is disposed proximal to a proximal end of a substantially constant diameter portion of the fluid lumen.

7. The blood pump of claim 4, wherein at least 60% of the proximal impeller, measured along an axial length, is disposed proximal to a proximal end of a substantially constant diameter portion of the fluid lumen.

8. The blood pump of claim 4, wherein at least 65% of the proximal impeller, measured along an axial length, is disposed proximal to a proximal end of a substantially constant diameter portion of the fluid lumen.

9. The blood pump of claim 4, wherein at most 90% of the proximal impeller, measured along an axial length, is disposed proximal to a proximal end of a substantially constant diameter portion of the fluid lumen.

10. The blood pump of claim 9, wherein at most 80% of the proximal impeller, measured along an axial length, is disposed proximal to a proximal end of a substantially constant diameter portion of the fluid lumen.

11. The blood pump of claim 10, wherein at most 75% of the proximal impeller, measured along an axial length, is disposed proximal to a proximal end of a substantially constant diameter portion of the fluid lumen.

12. The blood pump of claim 11, wherein at most 70% of the proximal impeller, measured along an axial length, is disposed proximal to a proximal end of a substantially constant diameter portion of the fluid lumen.

13. The blood pump of claim 11, wherein at most 65% of the proximal impeller, measured along an axial length, is disposed proximal to a proximal end of a substantially constant diameter portion of the fluid lumen.

14. The blood pump of claim 11, wherein at most 60% of the proximal impeller, measured along an axial length, is disposed proximal to a proximal end of a substantially constant diameter portion of the fluid lumen.

15. The blood pump of claim 11, wherein at most 55% of the proximal impeller, measured along an axial length, is disposed proximal to a proximal end of a substantially constant diameter portion of the fluid lumen.

16. The blood pump of claim 1, wherein at least half of the proximal impeller, measured along an axial length, is disposed in a flared proximal region of the fluid lumen.

17. The blood pump of claim 1, wherein the proximal impeller and the distal impeller are each, when in their expanded configurations, positioned relative to the fluid lumen such that the proximal impeller is performing more than 55% of the work of the blood pump and the distal impeller is performing less than 45% of the work of the blood pump.

18. The blood pump of claim 17, wherein the proximal impeller and the distal impeller are each, when in their expanded configurations, positioned relative to the fluid lumen such that the proximal impeller is performing more than 60% of the work of the blood pump and the distal impeller is performing less than 40% of the work of the blood pump.

19. The blood pump of claim 18, wherein the proximal impeller and the distal impeller are each, when in their expanded configurations, positioned relative to the fluid lumen such that the proximal impeller is performing more than 70% of the work of the blood pump and the distal impeller is performing less than 30% of the work of the blood pump.

20. The blood pump of claim 19, wherein the proximal impeller and the distal impeller are each, when in their expanded configurations, positioned relative to the fluid lumen such that the proximal impeller is performing about 80% of the work of the blood pump and the distal impeller is performing about 20% of the work of the blood pump.

21. A method of intravascularly pumping blood in a subject, comprising:
   positioning a pump housing fluid lumen first end in a left ventricle;
   positioning a distal impeller of the blood pump in the left ventricle;
   positioning a proximal impeller of the blood pump in an ascending aorta;
   positioning a pump housing fluid lumen second end in the ascending aorta;
   positioning at least a portion of a central region of the fluid lumen across an aortic valve,
   creating a flow path between the fluid lumen first end positioned in the left ventricle and the fluid lumen second end positioned in the ascending aorta such that the distal impeller and the proximal impeller can pump blood through the fluid lumen;
   rotating the distal impeller and proximal impeller and thereby causing the proximal impeller to perform more than 50% of the work of the blood pump and the distal impeller to perform less than 50% of the work of the blood pump.

22. The method of claim 21, wherein the rotating step comprises rotating the distal impeller and proximal impeller and thereby causing the proximal impeller to perform more than 60% of the work of the blood pump and the distal impeller to perform less than 40% of the work of the blood pump.

23. The method of claim 21, wherein the rotating step comprises rotating the distal impeller and proximal impeller and thereby causing the proximal impeller to perform more than 70% of the work of the blood pump and the distal impeller to perform less than 30% of the work of the blood pump.

24. The method of claim 21, wherein the rotating step comprises rotating the distal impeller and proximal impeller and thereby causing the proximal impeller to perform more than 75% of the work of the blood pump and the distal impeller to perform less than 25% of the work of the blood pump.

25. The method of claim 21, wherein the rotating step comprises rotating the distal impeller and proximal impeller and thereby causing the proximal impeller to perform about 80% of the work of the blood pump and the distal impeller to perform about 20% of the work of the blood pump.

26. An intravascular blood pump, comprising:
   a collapsible housing comprising a fluid lumen, the fluid lumen having a distal end and a proximal end;
   a collapsible distal impeller axially spaced from a collapsible proximal impeller, the distal impeller having an expanded configuration and the proximal impeller having an expanded configuration, and at least a portion of each of the distal and proximal impellers disposed between the distal and proximal ends of the fluid lumen,
   wherein the proximal impeller and the distal impeller are each, when in their expanded configurations and when rotated, positioned relative to the fluid lumen such that the proximal impeller is generating more than 50% of the pressure generated by the blood pump and the distal impeller is generating less than 50% of the pressure generated by the blood pump of the blood pump.

27. The blood pump of claim 26, wherein the blood pump does not include a vane disposed axially between the proximal and distal impellers.

28. The blood pump of claim 26, wherein the blood pump does not include a stator blade disposed axially between the proximal and distal impellers.

29. The blood pump of claim 26, wherein at least half of the proximal impeller, measured along an axial length, is disposed proximal to a proximal end of a substantially constant diameter portion of the fluid lumen.

30. The blood pump of claim 29, wherein at least 50% of the proximal impeller, measured along an axial length, is disposed proximal to a proximal end of a substantially constant diameter portion of the fluid lumen.

31. The blood pump of claim 29, wherein at least 55% of the proximal impeller, measured along an axial length, is disposed proximal to a proximal end of a substantially constant diameter portion of the fluid lumen.

32. The blood pump of claim 29, wherein at least 60% of the proximal impeller, measured along an axial length, is disposed proximal to a proximal end of a substantially constant diameter portion of the fluid lumen.

33. The blood pump of claim 29, wherein at least 65% of the proximal impeller, measured along an axial length, is disposed proximal to a proximal end of a substantially constant diameter portion of the fluid lumen.

34. The blood pump of claim 29, wherein at most 90% of the proximal impeller, measured along an axial length, is disposed proximal to a proximal end of a substantially constant diameter portion of the fluid lumen.

35. The blood pump of claim 34, wherein at most 80% of the proximal impeller, measured along an axial length, is disposed proximal to a proximal end of a substantially constant diameter portion of the fluid lumen.

36. The blood pump of claim 35, wherein at most 75% of the proximal impeller, measured along an axial length, is disposed proximal to a proximal end of a substantially constant diameter portion of the fluid lumen.

37. The blood pump of claim 36, wherein at most 70% of the proximal impeller, measured along an axial length, is disposed proximal to a proximal end of a substantially constant diameter portion of the fluid lumen.

38. The blood pump of claim 36, wherein at most 65% of the proximal impeller, measured along an axial length, is disposed proximal to a proximal end of a substantially constant diameter portion of the fluid lumen.

39. The blood pump of claim 37, wherein at most 60% of the proximal impeller, measured along an axial length, is disposed proximal to a proximal end of a substantially constant diameter portion of the fluid lumen.

40. The blood pump of claim 37, wherein at most 55% of the proximal impeller, measured along an axial length, is disposed proximal to a proximal end of a substantially constant diameter portion of the fluid lumen.

41. The blood pump of claim 26, wherein at least half of the proximal impeller, measured along an axial length, is disposed in a flared proximal region of the fluid lumen.

42. The blood pump of claim 26, wherein the proximal impeller and the distal impeller are each, when in their expanded configurations, positioned relative to the fluid lumen such that the proximal impeller is generating more than 55% of the pressure of the blood pump and the distal impeller is generating less than 45% of the pressure of the blood pump.

43. The blood pump of claim 42, wherein the proximal impeller and the distal impeller are each, when in their expanded configurations, positioned relative to the fluid lumen such that the proximal impeller is generating more than 60% of the pressure of the blood pump and the distal impeller is generating less than 40% of the pressure of the blood pump.

44. The blood pump of claim 43, wherein the proximal impeller and the distal impeller are each, when in their expanded configurations, positioned relative to the fluid lumen such that the proximal impeller is generating more than 70% of the pressure of the blood pump and the distal impeller is generating less than 30% of the pressure of the blood pump.

45. The blood pump of claim 44, wherein the proximal impeller and the distal impeller are each, when in their expanded configurations, positioned relative to the fluid lumen such that the proximal impeller is generating about 80% of the pressure of the blood pump and the distal impeller is generating about 20% of the pressure of the blood pump.

46. A method of intravascularly pumping blood in a subject, comprising:
- positioning a pump housing fluid lumen first end in a left ventricle;
- positioning a distal impeller of the blood pump in the left ventricle;
- positioning a proximal impeller of the blood pump in an ascending aorta;
- positioning a pump housing fluid lumen second end in the ascending aorta;
- positioning at least a portion of a central region of the fluid lumen across an aortic valve,
- creating a flow path between the fluid lumen first end positioned in the left ventricle and the fluid lumen second end positioned in the ascending aorta such that the distal impeller and the proximal impeller can pump blood through the fluid lumen;
- rotating the distal impeller and proximal impeller and thereby causing the proximal impeller to generate more than 50% of the pressure of the blood pump and the distal impeller to generate less than 50% of the pressure of the blood pump.

\* \* \* \* \*